US012697481B2

(12) United States Patent
Zipory et al.

(10) Patent No.: US 12,697,481 B2
(45) Date of Patent: Aug. 4, 2026

(54) CENTRIFUGAL AND MIXED-FLOW IMPELLERS FOR USE WITH A BLOOD PUMP

(71) Applicant: MAGENTA MEDICAL LTD, Kadima (IL)

(72) Inventors: Yuval Zipory, Modiin (IL); Ori Friedland, Tel Aviv (IL); Yonatan Levi, Tel Aviv (IL); Yosi Tuval, Even Yehuda (IL)

(73) Assignee: MAGENTA MEDICAL LTD, Kadima (IL)

( * ) Notice: Subject to any disclaimer, the term of this patent is extended or adjusted under 35 U.S.C. 154(b) by 708 days.

(21) Appl. No.: 17/907,618

(22) PCT Filed: Mar. 29, 2021

(86) PCT No.: PCT/IB2021/052590
§ 371 (c)(1),
(2) Date: Sep. 28, 2022

(87) PCT Pub. No.: WO2021/198881
PCT Pub. Date: Oct. 7, 2021

(65) Prior Publication Data
US 2023/0137473 A1      May 4, 2023

Related U.S. Application Data

(60) Provisional application No. 63/003,955, filed on Apr. 2, 2020.

(51) Int. Cl.
*A61M 60/808* (2021.01)
*A61M 60/13* (2021.01)
(Continued)

(52) U.S. Cl.
CPC .......... *A61M 60/13* (2021.01); *A61M 60/232* (2021.01); *A61M 60/812* (2021.01); *A61M 60/808* (2021.01)

(58) Field of Classification Search
CPC . A61M 60/808; A61M 60/178; A61M 60/232
See application file for complete search history.

(56) References Cited

U.S. PATENT DOCUMENTS 3,592,183 A    7/1971  Watkins et al.
3,932,068 A    1/1976  Zimmermann
(Continued)

FOREIGN PATENT DOCUMENTS

AU        2008219653 A1    9/2008
AU        2013205145 A1    5/2013
(Continued)

OTHER PUBLICATIONS

Corrected Notice of Allowability for U.S. Appl. No. 16/810,116 mailed Apr. 7, 2023.
(Continued)

*Primary Examiner* — George R Evanisko
(74) *Attorney, Agent, or Firm* — Ballard Spahr LLP

(57) ABSTRACT

Apparatus and methods are described including a left-ventricular assist device (20) that includes a pump-outlet tube (28). A mixed-flow impeller (100) is configured to pump blood from a subjects left ventricle to the subjects aorta, by pumping the blood into the pump-outlet tube (28) via one or more blood inlet openings (108) disposed within the left ventricle, and by pumping blood out of the pump-outlet tube (28) via one or more blood outlet openings (30) disposed within the aorta. The mixed-flow impeller (100) includes an expandable portion (116) disposed along its axis and shaped such that a diameter of the expandable portion increases from a distal end of the expandable portion to its (Continued)

proximal end. The mixed-flow impeller (100) is configured to impart radial flow components to blood as the blood flows from its distal end to its proximal end. Other applications are also described.

11 Claims, 33 Drawing Sheets

(51) Int. Cl.
A61M 60/232 (2021.01)
A61M 60/812 (2021.01)

(56) References Cited

U.S. PATENT DOCUMENTS

| | | | |
|---|---|---|---|
| 4,407,271 A | 10/1983 | Schiff | |
| 4,625,712 A | 12/1986 | Wampler | |
| 4,753,221 A | 6/1988 | Kensey et al. | |
| 4,771,765 A | 9/1988 | Choy | |
| 4,919,647 A | 4/1990 | Nash | |
| 4,944,722 A | 7/1990 | Carriker et al. | |
| 4,954,055 A | 9/1990 | Raible et al. | |
| 4,957,504 A | 9/1990 | Chardack | |
| 4,964,864 A | 10/1990 | Summers et al. | |
| 4,969,865 A | 11/1990 | Hwang et al. | |
| 4,985,014 A | 1/1991 | Orejola | |
| 5,011,469 A | 4/1991 | Buckberg et al. | |
| 5,037,403 A | 8/1991 | Garcia | |
| 5,061,256 A | 10/1991 | Wampler | |
| 5,169,378 A | 12/1992 | Figuera | |
| 5,275,580 A | 1/1994 | Yamazaki | |
| 5,330,484 A | 7/1994 | Guenther et al. | |
| 5,348,545 A | 9/1994 | Shani et al. | |
| 5,453,076 A | 9/1995 | Kiyota et al. | |
| 5,507,629 A | 4/1996 | Jarvik | |
| 5,531,789 A | 7/1996 | Yamazaki et al. | |
| 5,569,275 A | 10/1996 | Kotula et al. | |
| 5,613,935 A | 3/1997 | Jarvik | |
| 5,692,882 A | 12/1997 | Bozeman et al. | |
| 5,713,730 A | 2/1998 | Nose et al. | |
| 5,749,855 A | 5/1998 | Reitan | |
| 5,772,693 A | 6/1998 | Brownlee | |
| 5,843,158 A | 12/1998 | Lenker et al. | |
| 5,863,179 A | 1/1999 | Westphal et al. | |
| 5,876,385 A | 3/1999 | Ikari et al. | |
| 5,879,499 A | 3/1999 | Corvi | |
| 5,911,685 A | 6/1999 | Siess et al. | |
| 5,928,132 A | 7/1999 | Leschinsky | |
| 5,947,892 A | 9/1999 | Benkowski et al. | |
| 5,957,672 A | 9/1999 | Aber | |
| 5,964,694 A | 10/1999 | Siess et al. | |
| 6,007,478 A | 12/1999 | Siess et al. | |
| 6,059,760 A | 5/2000 | Sandmore et al. | |
| 6,086,527 A | 7/2000 | Talpade | |
| 6,116,862 A | 9/2000 | Rau et al. | |
| 6,135,729 A | 10/2000 | Aber | |
| 6,136,025 A | 10/2000 | Barbut et al. | |
| 6,162,017 A | 12/2000 | Raible | |
| 6,176,848 B1 | 1/2001 | Rau et al. | |
| 6,183,220 B1 | 2/2001 | Ohara et al. | |
| 6,217,541 B1 | 4/2001 | Yu | |
| 6,247,892 B1 | 6/2001 | Kazatchkov et al. | |
| 6,355,001 B1 | 3/2002 | Quinn et al. | |
| 6,413,222 B1 | 7/2002 | Pantages et al. | |
| 6,482,228 B1 | 11/2002 | Norred | |
| 6,506,146 B1 | 1/2003 | Mohl | |
| 6,533,716 B1 | 3/2003 | Schmutz-Rode et al. | |
| 6,533,770 B1 | 3/2003 | Lepulu et al. | |
| 6,537,315 B2 | 3/2003 | Yamazaki et al. | |
| 6,544,216 B1 | 4/2003 | Sammler et al. | |
| 6,592,567 B1 | 7/2003 | Levin et al. | |
| 6,616,624 B1 | 9/2003 | Kieval | |
| 6,884,210 B2 | 4/2005 | Nose et al. | |
| 6,949,066 B2 | 9/2005 | Bearnson et al. | |
| 6,974,436 B1 | 12/2005 | Aboul-Hosn et al. | |
| 7,004,925 B2 | 2/2006 | Navia et al. | |
| 7,010,954 B2 | 3/2006 | Siess et al. | |
| 7,011,620 B1 | 3/2006 | Siess | |
| 7,022,100 B1 * | 4/2006 | Aboul-Hosn | A61M 60/865 |
| | | | 604/6.11 |
| 7,027,875 B2 | 4/2006 | Siess et al. | |
| 7,070,555 B2 | 7/2006 | Siess | |
| 7,144,364 B2 | 12/2006 | Barbut et al. | |
| 7,159,593 B2 | 1/2007 | McCarthy et al. | |
| 7,201,772 B2 | 4/2007 | Schwammenthal et al. | |
| 7,258,679 B2 | 8/2007 | Moore et al. | |
| 7,335,192 B2 | 2/2008 | Keren et al. | |
| 7,338,521 B2 | 3/2008 | Antaki et al. | |
| 7,341,570 B2 | 3/2008 | Keren et al. | |
| 7,393,181 B2 | 7/2008 | McBride et al. | |
| 7,485,104 B2 | 2/2009 | Kieval | |
| 7,717,952 B2 | 5/2010 | Case et al. | |
| 7,744,642 B2 | 6/2010 | Rittgers et al. | |
| 7,762,941 B2 | 7/2010 | Jarvik | |
| 7,766,853 B2 | 8/2010 | Lane | |
| 7,766,892 B2 | 8/2010 | Keren et al. | |
| 7,766,961 B2 | 8/2010 | Patel et al. | |
| 7,780,628 B1 | 8/2010 | Keren et al. | |
| 7,811,221 B2 | 10/2010 | Gross | |
| 7,841,976 B2 | 11/2010 | McBride et al. | |
| 7,878,967 B1 | 2/2011 | Khanal | |
| 7,914,436 B1 | 3/2011 | Kung | |
| 7,914,503 B2 | 3/2011 | Goodson et al. | |
| 7,927,068 B2 | 4/2011 | Mcbride et al. | |
| 8,012,121 B2 | 9/2011 | Goodson et al. | |
| 8,079,948 B2 | 12/2011 | Shifflette | |
| 8,118,723 B2 | 2/2012 | Richardson et al. | |
| 8,123,669 B2 | 2/2012 | Siess et al. | |
| 8,157,758 B2 | 4/2012 | Pecor et al. | |
| 8,192,451 B2 | 6/2012 | Cambronne et al. | |
| 8,216,122 B2 | 7/2012 | Kung | |
| 8,221,492 B2 | 7/2012 | Case et al. | |
| 8,235,933 B2 | 8/2012 | Keren et al. | |
| 8,277,470 B2 | 10/2012 | Demarais et al. | |
| 8,376,707 B2 | 2/2013 | Mcbride et al. | |
| 8,439,859 B2 | 5/2013 | Pfeffer et al. | |
| 8,449,443 B2 | 5/2013 | Rodefeld et al. | |
| 8,485,961 B2 | 7/2013 | Campbell et al. | |
| 8,489,190 B2 | 7/2013 | Pfeffer et al. | |
| 8,512,262 B2 | 8/2013 | Gertner | |
| 8,535,211 B2 | 9/2013 | Walters et al. | |
| 8,538,535 B2 | 9/2013 | Ariav et al. | |
| 8,579,858 B2 | 11/2013 | Reitan et al. | |
| 8,591,393 B2 | 11/2013 | Walters et al. | |
| 8,591,539 B2 | 11/2013 | Gellman | |
| 8,597,170 B2 | 12/2013 | Walters et al. | |
| 8,617,239 B2 | 12/2013 | Reitan | |
| 8,672,868 B2 | 3/2014 | Simons | |
| 8,684,904 B2 | 4/2014 | Campbell et al. | |
| 8,690,749 B1 | 4/2014 | Nunez | |
| 8,721,516 B2 | 5/2014 | Scheckel | |
| 8,721,517 B2 | 5/2014 | Zeng et al. | |
| 8,727,959 B2 | 5/2014 | Reitan et al. | |
| 8,734,331 B2 | 5/2014 | Evans et al. | |
| 8,734,508 B2 | 5/2014 | Hastings et al. | |
| 8,777,832 B1 | 7/2014 | Wang et al. | |
| 8,814,543 B2 | 8/2014 | Liebing | |
| 8,814,776 B2 | 8/2014 | Hastie et al. | |
| 8,814,933 B2 | 8/2014 | Siess | |
| 8,827,887 B2 | 9/2014 | Curtis et al. | |
| 8,849,398 B2 | 9/2014 | Evans | |
| 8,864,642 B2 | 10/2014 | Scheckel | |
| 8,888,728 B2 | 11/2014 | Aboul-Hosn et al. | |
| 8,900,060 B2 | 12/2014 | Liebing | |
| 8,926,492 B2 | 1/2015 | Scheckel | |
| 8,932,141 B2 | 1/2015 | Liebing | |
| 8,944,748 B2 | 2/2015 | Liebing | |
| 8,979,493 B2 | 3/2015 | Roehn | |
| 8,992,163 B2 | 3/2015 | Mcbride et al. | |
| 8,998,792 B2 | 4/2015 | Scheckel | |
| 9,028,216 B2 | 5/2015 | Schumacher et al. | |
| 9,067,006 B2 | 6/2015 | Toellner | |
| 9,072,825 B2 | 7/2015 | Pfeffer et al. | |
| 9,089,634 B2 | 7/2015 | Schumacher et al. | |

(56) References Cited

U.S. PATENT DOCUMENTS

| | | | |
|---|---|---|---|
| 9,138,518 B2 | 9/2015 | Campbell et al. |
| 9,162,017 B2 | 10/2015 | Evans et al. |
| 9,162,019 B2 | 10/2015 | Horvath et al. |
| 9,217,442 B2 | 12/2015 | Wiessler et al. |
| 9,259,521 B2 | 2/2016 | Simons |
| 9,278,189 B2 | 3/2016 | Corbett |
| 9,314,558 B2 | 4/2016 | Er |
| 9,327,067 B2 | 5/2016 | Zeng et al. |
| 9,328,741 B2 | 5/2016 | Liebing |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,592 B2 | 6/2016 | Mcbride et al. |
| 9,364,593 B2 | 6/2016 | Mcbride et al. |
| 9,370,613 B2 | 6/2016 | Hsu et al. |
| 9,381,288 B2 | 7/2016 | Schenck et al. |
| 9,393,384 B1 | 7/2016 | Kapur et al. |
| 9,402,942 B2 | 8/2016 | Hastie et al. |
| 9,404,505 B2 | 8/2016 | Scheckel |
| 9,416,783 B2 | 8/2016 | Schumacher et al. |
| 9,416,791 B2 | 8/2016 | Toellner |
| 9,421,311 B2 | 8/2016 | Tanner et al. |
| 9,446,179 B2 | 9/2016 | Keenan et al. |
| 9,474,840 B2 | 10/2016 | Siess |
| 9,512,839 B2 | 12/2016 | Liebing |
| 9,533,082 B2 | 1/2017 | Reichenbach et al. |
| 9,533,084 B2 | 1/2017 | Siess et al. |
| 9,545,468 B2 | 1/2017 | Aboul-Hosn et al. |
| 9,550,017 B2 | 1/2017 | Spanier et al. |
| 9,561,314 B2 | 2/2017 | Aboul-Hosn et al. |
| 9,572,915 B2 | 2/2017 | Heuring et al. |
| 9,597,205 B2 | 3/2017 | Tuval |
| 9,597,437 B2 | 3/2017 | Aboul-Hosn et al. |
| 9,603,983 B2 | 3/2017 | Roehn et al. |
| 9,611,743 B2 | 4/2017 | Toellner et al. |
| 9,616,159 B2 | 4/2017 | Anderson et al. |
| 9,623,161 B2 | 4/2017 | Medvedev et al. |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,675,740 B2 | 6/2017 | Zeng et al. |
| 9,713,663 B2 | 7/2017 | Medvedev et al. |
| 9,717,833 B2 | 8/2017 | Mcbride et al. |
| 9,750,860 B2 | 9/2017 | Schumacher |
| 9,750,861 B2 | 9/2017 | Hastie et al. |
| 9,759,237 B2 | 9/2017 | Liebing |
| 9,764,113 B2 | 9/2017 | Tuval et al. |
| 9,771,801 B2 | 9/2017 | Schumacher et al. |
| 9,789,238 B2 | 10/2017 | Aboul-Hosn et al. |
| 9,795,727 B2 | 10/2017 | Schumacher |
| 9,814,814 B2 | 11/2017 | Corbett et al. |
| 9,821,146 B2 | 11/2017 | Tao et al. |
| 9,827,356 B2 | 11/2017 | Muller et al. |
| 9,833,550 B2 | 12/2017 | Siess |
| 9,835,550 B2 | 12/2017 | Kakuno et al. |
| 9,850,906 B2 | 12/2017 | Ozaki et al. |
| 9,872,947 B2 | 1/2018 | Keenan et al. |
| 9,872,948 B2 | 1/2018 | Siess |
| 9,878,079 B2 | 1/2018 | Pfeffer et al. |
| 9,889,242 B2 | 2/2018 | Pfeffer et al. |
| 9,895,475 B2 | 2/2018 | Toellner et al. |
| 9,903,384 B2 | 2/2018 | Roehn |
| 9,907,890 B2 | 3/2018 | Muller |
| 9,907,891 B2 | 3/2018 | Wiessler et al. |
| 9,919,087 B2 | 3/2018 | Pfeffer et al. |
| 9,962,475 B2 | 5/2018 | Campbell et al. |
| 9,964,115 B2 | 5/2018 | Scheckel |
| 9,974,893 B2 | 5/2018 | Toellner |
| 9,999,714 B2 | 6/2018 | Spanier et al. |
| 10,029,037 B2 | 7/2018 | Muller et al. |
| 10,029,040 B2 | 7/2018 | Taskin |
| 10,039,872 B2 | 8/2018 | Zeng et al. |
| 10,039,874 B2 | 8/2018 | Schwammenthal et al. |
| 10,052,419 B2 | 8/2018 | Er |
| 10,052,420 B2 | 8/2018 | Medvedev et al. |
| 10,071,192 B2 | 9/2018 | Zeng |
| 10,086,121 B2 | 10/2018 | Fitzgerald et al. |
| 10,105,475 B2 | 10/2018 | Muller |
| 10,107,299 B2 | 10/2018 | Scheckel |
| 10,117,980 B2 | 11/2018 | Keenan et al. |
| 10,119,550 B2 | 11/2018 | Bredenbreuker et al. |
| 10,149,932 B2 | 12/2018 | Mcbride et al. |
| 10,172,985 B2 | 1/2019 | Simon et al. |
| 10,179,197 B2 | 1/2019 | Kaiser et al. |
| 10,183,104 B2 | 1/2019 | Anderson et al. |
| 10,196,899 B2 | 2/2019 | Toellner et al. |
| 10,207,037 B2 | 2/2019 | Corbett et al. |
| 10,208,763 B2 | 2/2019 | Schumacher et al. |
| 10,215,187 B2 | 2/2019 | Mcbride et al. |
| 10,221,866 B2 | 3/2019 | Liebing |
| 10,231,838 B2 | 3/2019 | Chin et al. |
| 10,232,099 B2 | 3/2019 | Peters |
| 10,238,783 B2 | 3/2019 | Aboul-Hosn et al. |
| 10,245,363 B1 | 4/2019 | Rowe |
| 10,265,447 B2 | 4/2019 | Campbell et al. |
| 10,265,448 B2 | 4/2019 | Liebing |
| 10,279,095 B2 | 5/2019 | Aboul-Hosn et al. |
| 10,300,185 B2 | 5/2019 | Aboul-Hosn et al. |
| 10,300,186 B2 | 5/2019 | Aboul-Hosn et al. |
| 10,316,853 B2 | 6/2019 | Toellner |
| 10,322,175 B2 | 6/2019 | Cully |
| 10,330,101 B2 | 6/2019 | Toellner |
| 10,342,904 B2 | 7/2019 | Schumacher |
| 10,342,906 B2 | 7/2019 | D'Ambrosio et al. |
| 10,363,349 B2 | 7/2019 | Muller et al. |
| 10,369,260 B2 | 8/2019 | Smith et al. |
| 10,376,162 B2 | 8/2019 | Edelman et al. |
| 10,413,646 B2 | 9/2019 | Wiessler et al. |
| 10,449,276 B2 | 10/2019 | Pfeffer et al. |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,540 B2 | 11/2019 | Scheckel et al. |
| 10,495,101 B2 | 12/2019 | Scheckel |
| 10,557,475 B2 | 2/2020 | Roehn |
| 10,583,231 B2 | 3/2020 | Schwammenthal et al. |
| 10,584,589 B2 | 3/2020 | Schumacher et al. |
| 10,589,012 B2 | 3/2020 | Toellner et al. |
| 10,617,808 B2 | 4/2020 | Hastie et al. |
| 10,662,967 B2 | 5/2020 | Scheckel |
| 10,669,855 B2 | 6/2020 | Toellner et al. |
| 10,765,789 B2 | 9/2020 | Zeng et al. |
| 10,792,406 B2 | 10/2020 | Roehn et al. |
| 10,799,624 B2 | 10/2020 | Pfeffer et al. |
| 10,799,626 B2 | 10/2020 | Siess et al. |
| 10,801,511 B2 | 10/2020 | Siess et al. |
| 10,806,838 B2 | 10/2020 | Er |
| 10,835,653 B2 | 11/2020 | Liebing |
| 10,842,922 B2 | 11/2020 | Roehn |
| 10,857,272 B2 | 12/2020 | Liebing |
| 10,864,309 B2 | 12/2020 | Mcbride et al. |
| 10,864,310 B2 | 12/2020 | Schwammenthal et al. |
| 10,865,801 B2 | 12/2020 | Mcbride et al. |
| 10,874,783 B2 | 12/2020 | Pfeffer et al. |
| 10,881,770 B2 | 1/2021 | Tuval et al. |
| 10,881,845 B2 | 1/2021 | Siess et al. |
| 10,894,115 B2 | 1/2021 | Pfeffer et al. |
| 10,898,629 B2 | 1/2021 | Siess et al. |
| 10,907,646 B2 | 2/2021 | Bredenbreuker et al. |
| 10,920,596 B2 | 2/2021 | Toellner et al. |
| 10,926,013 B2 | 2/2021 | Schumacher et al. |
| 10,935,038 B2 | 3/2021 | Siess |
| 10,980,927 B2 | 4/2021 | Pfeffer et al. |
| 10,994,120 B2 | 5/2021 | Tuval et al. |
| 11,007,350 B2 | 5/2021 | Tao et al. |
| 11,020,584 B2 | 6/2021 | Siess et al. |
| 11,027,114 B2 | 6/2021 | D'Ambrosio et al. |
| 11,033,729 B2 | 6/2021 | Scheckel et al. |
| 11,040,187 B2 | 6/2021 | Wiessler et al. |
| RE48,649 E | 7/2021 | Siess |
| 11,077,294 B2 | 8/2021 | Keenan et al. |
| 11,107,626 B2 | 8/2021 | Siess et al. |
| 11,116,960 B2 | 9/2021 | Simon et al. |

(56) References Cited

U.S. PATENT DOCUMENTS

| | | | |
|---|---|---|---|
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,168,705 | B2 | 11/2021 | Liebing |
| 11,185,679 | B2 | 11/2021 | Tuval et al. |
| 11,185,680 | B2 | 11/2021 | Tuval et al. |
| 11,191,944 | B2 | 12/2021 | Tuval et al. |
| 11,197,690 | B2 | 12/2021 | Fantuzzi et al. |
| 11,219,755 | B2 | 1/2022 | Siess et al. |
| 11,229,786 | B2 | 1/2022 | Zeng et al. |
| 11,253,692 | B2 | 2/2022 | Schumacher |
| 11,253,693 | B2 | 2/2022 | Pfeffer et al. |
| 11,260,212 | B2 | 3/2022 | Tuval et al. |
| 11,260,213 | B2 | 3/2022 | Zeng et al. |
| 11,260,215 | B2 | 3/2022 | Scheckel et al. |
| 11,266,824 | B2 | 3/2022 | Er |
| 11,268,521 | B2 | 3/2022 | Toellner |
| 11,273,301 | B2 | 3/2022 | Pfeffer et al. |
| 11,278,711 | B2 | 3/2022 | Liebing |
| 11,280,345 | B2 | 3/2022 | Bredenbreuker et al. |
| 11,285,309 | B2 | 3/2022 | Tuval et al. |
| 11,291,825 | B2 | 4/2022 | Tuval et al. |
| 11,298,523 | B2 | 4/2022 | Tuval et al. |
| 11,298,525 | B2 | 4/2022 | Jahangir |
| 11,305,105 | B2 | 4/2022 | Corbett et al. |
| 11,313,228 | B2 | 4/2022 | Schumacher et al. |
| 11,338,124 | B2 | 5/2022 | Pfeffer et al. |
| 11,351,358 | B2 | 6/2022 | Nix et al. |
| 11,364,373 | B2 | 6/2022 | Corbett et al. |
| 11,421,701 | B2 | 8/2022 | Schumacher et al. |
| 11,434,922 | B2 | 9/2022 | Roehn |
| 11,471,663 | B2 | 10/2022 | Tuval et al. |
| 11,708,833 | B2 | 7/2023 | Mcbride et al. |
| 11,833,278 | B2 | 12/2023 | Siess et al. |
| 11,883,274 | B2 | 1/2024 | Schwammenthal |
| 11,986,602 | B2 | 5/2024 | Corbett et al. |
| 12,329,957 | B2 | 6/2025 | Tuval et al. |
| 2001/0031210 | A1 | 10/2001 | Antaki et al. |
| 2001/0031981 | A1 | 10/2001 | Evans et al. |
| 2001/0041934 | A1 | 11/2001 | Yamazaki et al. |
| 2002/0107536 | A1 | 8/2002 | Hussein |
| 2002/0151799 | A1 | 10/2002 | Pantages et al. |
| 2003/0055486 | A1 | 3/2003 | Adams et al. |
| 2003/0088310 | A1 | 5/2003 | Hansen et al. |
| 2003/0100816 | A1 | 5/2003 | Siess |
| 2003/0135086 | A1 | 7/2003 | Khaw et al. |
| 2003/0149473 | A1 | 8/2003 | Chouinard et al. |
| 2003/0187322 | A1 | 10/2003 | Siess |
| 2003/0208097 | A1 | 11/2003 | Aboul-Hosn et al. |
| 2004/0064090 | A1 | 4/2004 | Keren et al. |
| 2004/0064091 | A1 | 4/2004 | Keren et al. |
| 2004/0111006 | A1 | 6/2004 | Alferness et al. |
| 2004/0116769 | A1 | 6/2004 | Jassawalla et al. |
| 2004/0167415 | A1 | 8/2004 | Gelfand et al. |
| 2004/0210236 | A1 | 10/2004 | Allers et al. |
| 2004/0260389 | A1 | 12/2004 | Case et al. |
| 2005/0033406 | A1 | 2/2005 | Barnhart et al. |
| 2005/0049692 | A1 | 3/2005 | Numamoto et al. |
| 2005/0079274 | A1 | 4/2005 | Palasis et al. |
| 2005/0085848 | A1 | 4/2005 | Johnson et al. |
| 2005/0107657 | A1 | 5/2005 | Carrier et al. |
| 2005/0119682 | A1 | 6/2005 | Nguyen et al. |
| 2005/0137680 | A1 | 6/2005 | Ortiz et al. |
| 2005/0180854 | A1 | 8/2005 | Grabau et al. |
| 2005/0250975 | A1 | 11/2005 | Carrier et al. |
| 2006/0062672 | A1 | 3/2006 | McBride et al. |
| 2006/0064059 | A1 | 3/2006 | Gelfand et al. |
| 2006/0106449 | A1 | 5/2006 | Ben |
| 2006/0135961 | A1 | 6/2006 | Rosenman et al. |
| 2006/0155322 | A1 | 7/2006 | Sater et al. |
| 2006/0265051 | A1 | 11/2006 | Caro et al. |
| 2007/0073271 | A1 | 3/2007 | Brucker et al. |
| 2007/0100415 | A1 | 5/2007 | Licata et al. |
| 2007/0100435 | A1 | 5/2007 | Case et al. |
| 2007/0142729 | A1 | 6/2007 | Pfeiffer et al. |
| 2007/0162103 | A1 | 7/2007 | Case et al. |
| 2007/0208291 | A1 | 9/2007 | Patel |
| 2007/0244550 | A1 | 10/2007 | Eidenschink |
| 2007/0260327 | A1 | 11/2007 | Case et al. |
| 2007/0282243 | A1 | 12/2007 | Pini et al. |
| 2007/0282413 | A1 | 12/2007 | Tockman et al. |
| 2007/0293808 | A1 | 12/2007 | Williams et al. |
| 2008/0009668 | A1 | 1/2008 | Cohn |
| 2008/0086027 | A1 | 4/2008 | Siess et al. |
| 2008/0103591 | A1 | 5/2008 | Siess |
| 2008/0114339 | A1 | 5/2008 | McBride et al. |
| 2008/0114374 | A1 | 5/2008 | Soma |
| 2008/0132747 | A1 | 6/2008 | Shifflette |
| 2008/0132748 | A1 | 6/2008 | Shifflette |
| 2008/0140189 | A1 | 6/2008 | Nguyen et al. |
| 2008/0154236 | A1 | 6/2008 | Elkins et al. |
| 2008/0183280 | A1 | 7/2008 | Agnew et al. |
| 2008/0219653 | A1 | 9/2008 | Shioda |
| 2008/0306327 | A1 | 12/2008 | Shifflette |
| 2008/0306328 | A1 | 12/2008 | Ercolani et al. |
| 2009/0024157 | A1 | 1/2009 | Anukhin |
| 2009/0024195 | A1 | 1/2009 | Rezai et al. |
| 2009/0062597 | A1 | 3/2009 | Shifflette |
| 2009/0093764 | A1 | 4/2009 | Pfeffer et al. |
| 2009/0093796 | A1 | 4/2009 | Pfeffer et al. |
| 2009/0264991 | A1 | 10/2009 | Paul et al. |
| 2009/0287299 | A1 | 11/2009 | Tabor et al. |
| 2009/0318857 | A1 | 12/2009 | Goodson et al. |
| 2010/0030098 | A1 | 2/2010 | Fojtik |
| 2010/0048793 | A1 | 2/2010 | Baekelandt et al. |
| 2010/0049313 | A1 | 2/2010 | Alon et al. |
| 2010/0076247 | A1 | 3/2010 | Zilbershlag et al. |
| 2010/0130810 | A1 | 5/2010 | Mohl |
| 2010/0152523 | A1 | 6/2010 | Macdonald et al. |
| 2010/0185043 | A1 | 7/2010 | Woodard et al. |
| 2010/0222632 | A1 | 9/2010 | Poirier |
| 2010/0268017 | A1 | 10/2010 | Siess |
| 2010/0285084 | A1 | 11/2010 | Yang |
| 2011/0004046 | A1 | 1/2011 | Campbell et al. |
| 2011/0034874 | A1 | 2/2011 | Reitan et al. |
| 2011/0106244 | A1 | 5/2011 | Ferrari et al. |
| 2011/0112567 | A1 | 5/2011 | Lenker et al. |
| 2011/0144633 | A1 | 6/2011 | Govari |
| 2011/0152999 | A1 | 6/2011 | Hastings et al. |
| 2011/0190874 | A1 | 8/2011 | Celermajer et al. |
| 2011/0213408 | A1 | 9/2011 | Gross et al. |
| 2011/0230949 | A1 | 9/2011 | Haverkost et al. |
| 2011/0257462 | A1 | 10/2011 | Rodefeld et al. |
| 2011/0264075 | A1 | 10/2011 | Leung et al. |
| 2011/0282128 | A1 | 11/2011 | Reitan et al. |
| 2011/0282274 | A1 | 11/2011 | Fulton |
| 2011/0301662 | A1 | 12/2011 | Bar-Yoseph et al. |
| 2012/0022579 | A1 | 1/2012 | Fulton |
| 2012/0059460 | A1 | 3/2012 | Reitan |
| 2012/0089047 | A1 | 4/2012 | Ryba et al. |
| 2012/0089225 | A1 | 4/2012 | Akkerman et al. |
| 2012/0093628 | A1 | 4/2012 | Liebing |
| 2012/0116382 | A1 | 5/2012 | Ku et al. |
| 2012/0130469 | A1 | 5/2012 | Cragg et al. |
| 2012/0143141 | A1 | 6/2012 | Verkaik et al. |
| 2012/0172654 | A1 | 7/2012 | Bates |
| 2012/0172655 | A1 | 7/2012 | Campbell et al. |
| 2012/0172656 | A1 | 7/2012 | Walters et al. |
| 2012/0178985 | A1 | 7/2012 | Walters et al. |
| 2012/0178986 | A1 | 7/2012 | Campbell et al. |
| 2012/0224970 | A1 | 9/2012 | Schumacher et al. |
| 2012/0234411 | A1 | 9/2012 | Scheckel |
| 2012/0237353 | A1 | 9/2012 | Schumacher et al. |
| 2012/0237357 | A1 | 9/2012 | Schumacher et al. |
| 2012/0245680 | A1 | 9/2012 | Masuzawa et al. |
| 2012/0303112 | A1 | 11/2012 | Armstrong et al. |
| 2012/0316586 | A1 | 12/2012 | Demarais et al. |
| 2012/0328460 | A1 | 12/2012 | Horvath et al. |
| 2013/0041202 | A1 | 2/2013 | Toellner |
| 2013/0046376 | A1 | 2/2013 | Hassan |
| 2013/0053623 | A1 | 2/2013 | Evans et al. |
| 2013/0053732 | A1 | 2/2013 | Heuser |
| 2013/0060077 | A1 | 3/2013 | Liebing |
| 2013/0066140 | A1 | 3/2013 | McBride et al. |

(56) References Cited

U.S. PATENT DOCUMENTS

| | | |
|---|---|---|
| 2013/0079874 A1 | 3/2013 | Doss et al. |
| 2013/0085318 A1 | 4/2013 | Toellner |
| 2013/0085319 A1 | 4/2013 | Evans et al. |
| 2013/0177407 A1 | 7/2013 | Farineau et al. |
| 2013/0177409 A1 | 7/2013 | Schumacher et al. |
| 2013/0177432 A1 | 7/2013 | Toellner et al. |
| 2013/0237744 A1 | 9/2013 | Pfeffer et al. |
| 2013/0245360 A1 | 9/2013 | Schumacher |
| 2013/0253328 A1 | 9/2013 | Zelenka et al. |
| 2013/0303831 A1* | 11/2013 | Evans ............... A61M 60/865 |
| | | 600/16 |
| 2013/0303969 A1 | 11/2013 | Keenan et al. |
| 2013/0331639 A1 | 12/2013 | Campbell |
| 2014/0018840 A1 | 1/2014 | Morgan et al. |
| 2014/0025041 A1 | 1/2014 | Fukuoka et al. |
| 2014/0107399 A1 | 4/2014 | Spence |
| 2014/0128659 A1 | 5/2014 | Heuring et al. |
| 2014/0255176 A1 | 9/2014 | Bredenbreuker et al. |
| 2014/0275720 A1 | 9/2014 | Ferrari |
| 2014/0275722 A1 | 9/2014 | Zimmermann et al. |
| 2014/0276051 A1 | 9/2014 | Hoffman |
| 2014/0350523 A1 | 11/2014 | Dehdashtian et al. |
| 2015/0005570 A1 | 1/2015 | Fritz et al. |
| 2015/0018597 A1 | 1/2015 | Fierens et al. |
| 2015/0051435 A1 | 2/2015 | Siess et al. |
| 2015/0119633 A1 | 4/2015 | Haselby et al. |
| 2015/0157777 A1 | 6/2015 | Tuval et al. |
| 2015/0164372 A1 | 6/2015 | Navab |
| 2015/0164662 A1 | 6/2015 | Tuval |
| 2015/0176582 A1 | 6/2015 | Liebing |
| 2015/0258262 A1 | 9/2015 | Pfeffer et al. |
| 2015/0290372 A1 | 10/2015 | Muller et al. |
| 2015/0306291 A1 | 10/2015 | Bonde et al. |
| 2015/0328382 A1 | 11/2015 | Corbett et al. |
| 2015/0343136 A1 | 12/2015 | Nitzan et al. |
| 2015/0343179 A1 | 12/2015 | Schumacher et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |
| 2016/0106896 A1 | 4/2016 | Pfeffer et al. |
| 2016/0129170 A1 | 5/2016 | Siess |
| 2016/0136341 A1 | 5/2016 | Pfeffer et al. |
| 2016/0136342 A1 | 5/2016 | Pfeffer et al. |
| 2016/0136343 A1 | 5/2016 | Anagnostopoulos |
| 2016/0144089 A1 | 5/2016 | Woo et al. |
| 2016/0184500 A1 | 6/2016 | Zeng |
| 2016/0213827 A1 | 7/2016 | Tanner |
| 2016/0256620 A1 | 9/2016 | Scheckel et al. |
| 2016/0279310 A1 | 9/2016 | Scheckel et al. |
| 2016/0331378 A1 | 11/2016 | Nitzan et al. |
| 2016/0354525 A1 | 12/2016 | Mcbride et al. |
| 2017/0007403 A1 | 1/2017 | Wildhirt et al. |
| 2017/0014562 A1 | 1/2017 | Liebing |
| 2017/0028115 A1 | 2/2017 | Muller |
| 2017/0035954 A1 | 2/2017 | Muller et al. |
| 2017/0049946 A1 | 2/2017 | Kapur et al. |
| 2017/0071769 A1 | 3/2017 | Mangiardi |
| 2017/0087286 A1 | 3/2017 | Spanier et al. |
| 2017/0087288 A1 | 3/2017 | Gross-Hardt et al. |
| 2017/0100527 A1 | 4/2017 | Schwammenthal et al. |
| 2017/0173237 A1 | 6/2017 | Pfeifer et al. |
| 2017/0197021 A1 | 7/2017 | Nitzan et al. |
| 2017/0215918 A1 | 8/2017 | Tao et al. |
| 2017/0232168 A1 | 8/2017 | Reichenbach et al. |
| 2017/0232171 A1 | 8/2017 | Roehn et al. |
| 2017/0258981 A1 | 9/2017 | Franano et al. |
| 2017/0290964 A1 | 10/2017 | Barry |
| 2017/0333067 A1 | 11/2017 | Wilson |
| 2017/0333607 A1 | 11/2017 | Zarins |
| 2017/0340787 A1 | 11/2017 | Corbett |
| 2017/0340791 A1 | 11/2017 | Aboul-Hosn et al. |
| 2017/0348470 A1 | 12/2017 | D'Ambrosio et al. |
| 2018/0050139 A1 | 2/2018 | Siess et al. |
| 2018/0050142 A1 | 2/2018 | Siess et al. |
| 2018/0055979 A1 | 3/2018 | Corbett et al. |
| 2018/0064861 A1 | 3/2018 | Dur et al. |
| 2018/0078159 A1 | 3/2018 | Edelman et al. |
| 2018/0080326 A1 | 3/2018 | Schumacher et al. |
| 2018/0100507 A1 | 4/2018 | Wu et al. |
| 2018/0104453 A1 | 4/2018 | Tao et al. |
| 2018/0149164 A1 | 5/2018 | Siess |
| 2018/0149165 A1 | 5/2018 | Siess et al. |
| 2018/0169312 A1 | 6/2018 | Barry |
| 2018/0169313 A1 | 6/2018 | Schwammenthal et al. |
| 2018/0207334 A1 | 7/2018 | Siess |
| 2018/0228952 A1 | 8/2018 | Pfeffer et al. |
| 2018/0228953 A1 | 8/2018 | Siess et al. |
| 2018/0264182 A1 | 9/2018 | Spanier et al. |
| 2018/0264183 A1 | 9/2018 | Jahangir |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0303992 A1 | 10/2018 | Taskin |
| 2018/0303993 A1 | 10/2018 | Schwammenthal et al. |
| 2018/0311422 A1 | 11/2018 | Greatrex et al. |
| 2018/0353667 A1 | 12/2018 | Moyer et al. |
| 2019/0015570 A1 | 1/2019 | Muller |
| 2019/0030228 A1 | 1/2019 | Keenan et al. |
| 2019/0046702 A1 | 2/2019 | Siess et al. |
| 2019/0060539 A1 | 2/2019 | Siess et al. |
| 2019/0070345 A1 | 3/2019 | Mcbride et al. |
| 2019/0076167 A1 | 3/2019 | Fantuzzi et al. |
| 2019/0083690 A1 | 3/2019 | Siess et al. |
| 2019/0093769 A1 | 3/2019 | Lima Sarabanda et al. |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0134287 A1 | 5/2019 | Demou |
| 2019/0143018 A1 | 5/2019 | Salahieh et al. |
| 2019/0143019 A1 | 5/2019 | Mehaffey et al. |
| 2019/0170153 A1 | 6/2019 | Scheckel |
| 2019/0175802 A1 | 6/2019 | Tuval et al. |
| 2019/0175803 A1 | 6/2019 | Pfeffer et al. |
| 2019/0175805 A1 | 6/2019 | Tuval et al. |
| 2019/0175806 A1 | 6/2019 | Tuval et al. |
| 2019/0209753 A1 | 7/2019 | Tuval et al. |
| 2019/0209755 A1 | 7/2019 | Nix et al. |
| 2019/0209757 A1 | 7/2019 | Tuval et al. |
| 2019/0209758 A1 | 7/2019 | Tuval et al. |
| 2019/0211836 A1 | 7/2019 | Schumacher et al. |
| 2019/0216994 A1 | 7/2019 | Pfeffer et al. |
| 2019/0224391 A1 | 7/2019 | Liebing |
| 2019/0224392 A1 | 7/2019 | Pfeffer et al. |
| 2019/0224393 A1 | 7/2019 | Pfeffer et al. |
| 2019/0239998 A1 | 8/2019 | Tuval et al. |
| 2019/0262518 A1 | 8/2019 | Molteni et al. |
| 2019/0269840 A1 | 9/2019 | Tuval et al. |
| 2019/0274812 A1 | 9/2019 | Groh et al. |
| 2019/0275224 A1 | 9/2019 | Hanson et al. |
| 2019/0282741 A1 | 9/2019 | Franano et al. |
| 2019/0290817 A1 | 9/2019 | Guo et al. |
| 2019/0307561 A1 | 10/2019 | Gosal et al. |
| 2019/0316591 A1 | 10/2019 | Toellner |
| 2019/0321527 A1 | 10/2019 | King et al. |
| 2019/0321530 A1 | 10/2019 | Cambronne et al. |
| 2019/0321531 A1 | 10/2019 | Cambronne et al. |
| 2019/0328948 A1 | 10/2019 | Salahieh et al. |
| 2019/0336664 A1 | 11/2019 | Liebing |
| 2019/0344001 A1 | 11/2019 | Salahieh et al. |
| 2019/0351118 A1 | 11/2019 | Graichen et al. |
| 2019/0365975 A1 | 12/2019 | Muller et al. |
| 2020/0000542 A1 | 1/2020 | Mcfall et al. |
| 2020/0038567 A1 | 2/2020 | Siess et al. |
| 2020/0078506 A1 | 3/2020 | Schwammenthal et al. |
| 2020/0086022 A1 | 3/2020 | El Katerji et al. |
| 2020/0087199 A1 | 3/2020 | Gimblet |
| 2020/0093973 A1 | 3/2020 | Gandhi et al. |
| 2020/0114053 A1 | 4/2020 | Salahieh et al. |
| 2020/0155739 A1 | 5/2020 | Siess et al. |
| 2020/0197585 A1 | 6/2020 | Scheckel et al. |
| 2020/0237981 A1 | 7/2020 | Tuval et al. |
| 2020/0237982 A1 | 7/2020 | Tuval et al. |
| 2020/0237984 A1 | 7/2020 | Tuval et al. |

(56) References Cited

U.S. PATENT DOCUMENTS

| | | | |
|---|---|---|---|
| 2020/0237985 A1 | 7/2020 | Tuval et al. | |
| 2020/0237986 A1 | 7/2020 | Tuval et al. | |
| 2020/0246527 A1* | 8/2020 | Hildebrand | A61M 60/422 |
| 2020/0268952 A1 | 8/2020 | Nitzan et al. | |
| 2020/0276369 A1 | 9/2020 | Nitzan et al. | |
| 2020/0288988 A1 | 9/2020 | Goldvasser | |
| 2020/0376183 A1 | 12/2020 | El Katerji et al. | |
| 2020/0405926 A1 | 12/2020 | Alexander et al. | |
| 2021/0008261 A1 | 1/2021 | Calomeni | |
| 2021/0023285 A1 | 1/2021 | Brandt | |
| 2021/0023286 A1 | 1/2021 | Tuval et al. | |
| 2021/0038794 A1 | 2/2021 | Tuval et al. | |
| 2021/0069394 A1 | 3/2021 | Tuval et al. | |
| 2021/0069395 A1 | 3/2021 | Tuval et al. | |
| 2021/0077676 A1 | 3/2021 | Tuval et al. | |
| 2021/0077692 A1 | 3/2021 | Tanner et al. | |
| 2021/0121617 A1 | 4/2021 | Harjes et al. | |
| 2021/0145475 A1 | 5/2021 | Tao et al. | |
| 2021/0162199 A1 | 6/2021 | Tuval et al. | |
| 2021/0170081 A1 | 6/2021 | Kanz | |
| 2021/0178145 A1 | 6/2021 | Tuval et al. | |
| 2021/0213273 A1 | 7/2021 | Spanier | |
| 2021/0236797 A1 | 8/2021 | D'Ambrosio et al. | |
| 2021/0260361 A1 | 8/2021 | Charafeddine et al. | |
| 2021/0299433 A1 | 9/2021 | Siess et al. | |
| 2022/0072297 A1 | 3/2022 | Tuval et al. | |
| 2022/0079457 A1 | 3/2022 | Tuval et al. | |
| 2022/0088368 A1 | 3/2022 | Tuval et al. | |
| 2022/0134085 A1 | 5/2022 | Siess et al. | |
| 2022/0161018 A1 | 5/2022 | Mitze et al. | |
| 2022/0161019 A1 | 5/2022 | Mitze et al. | |
| 2022/0184376 A1 | 6/2022 | Tuval et al. | |
| 2022/0226632 A1 | 7/2022 | Tuval et al. | |
| 2022/0249830 A1 | 8/2022 | Kanz | |
| 2022/0313980 A1* | 10/2022 | Hildebrand | A61M 60/237 |
| 2022/0355096 A1 | 11/2022 | Tuval et al. | |
| 2023/0001180 A1 | 1/2023 | Boensch et al. | |
| 2023/0052997 A1 | 2/2023 | Skrzypczak | |
| 2023/0063196 A1 | 3/2023 | Spanier et al. | |
| 2023/0071248 A1 | 3/2023 | Keenan et al. | |
| 2023/0137473 A1 | 5/2023 | Zipory et al. | |
| 2023/0226342 A1 | 7/2023 | Tuval et al. | |
| 2023/0390545 A1 | 12/2023 | D'Ambrosio | |
| 2024/0189571 A1 | 6/2024 | Tuval et al. | |
| 2024/0277997 A1 | 8/2024 | Tuval | |
| 2025/0387612 A1 | 12/2025 | van Dort et al. | |

FOREIGN PATENT DOCUMENTS

| | | |
|---|---|---|
| CA | 2701809 A1 | 4/2009 |
| CA | 2927346 A1 | 4/2009 |
| CN | 101448535 A | 6/2009 |
| CN | 101820933 | 9/2010 |
| CN | 101854964 | 10/2010 |
| CN | 102365105 | 2/2012 |
| CN | 102805885 A | 12/2012 |
| CN | 104185481 | 12/2014 |
| CN | 104703532 | 6/2015 |
| CN | 103182105 B | 1/2016 |
| CN | 105214153 | 1/2016 |
| CN | 105682602 | 6/2016 |
| CN | 107050544 | 8/2017 |
| CN | 107137796 | 9/2017 |
| CN | 109069716 | 12/2018 |
| CN | 109821085 | 5/2019 |
| CN | 113457006 A | 10/2021 |
| CN | 114259646 | 4/2022 |
| CN | 114588533 A | 6/2022 |
| CN | 116036463 | 5/2023 |
| CN | 116328174 | 6/2023 |
| CN | 116474257 | 6/2023 |
| CN | 116867541 | 10/2023 |
| DE | 10336902 B3 | 8/2004 |
| EP | 228787 | 6/1987 |
| EP | 256683 | 2/1988 |
| EP | 807447 | 11/1997 |
| EP | 0916359 A1 | 5/1999 |
| EP | 1339443 A1 | 9/2003 |
| EP | 0925801 B1 | 11/2004 |
| EP | 1651290 A1 | 5/2006 |
| EP | 1827531 A1 | 9/2007 |
| EP | 1871441 A2 | 1/2008 |
| EP | 2047872 A1 | 4/2009 |
| EP | 2047873 A1 | 4/2009 |
| EP | 2109394 A2 | 10/2009 |
| EP | 2217300 A1 | 8/2010 |
| EP | 2218469 A1 | 8/2010 |
| EP | 2234658 A2 | 10/2010 |
| EP | 2282070 A1 | 2/2011 |
| EP | 2298374 A1 | 3/2011 |
| EP | 2299119 A1 | 3/2011 |
| EP | 2301598 A1 | 3/2011 |
| EP | 2308524 A1 | 4/2011 |
| EP | 2314331 A1 | 4/2011 |
| EP | 2345440 A1 | 7/2011 |
| EP | 2366412 A2 | 9/2011 |
| EP | 2376788 A1 | 10/2011 |
| EP | 2408489 A1 | 1/2012 |
| EP | 2424587 A1 | 3/2012 |
| EP | 2475415 A1 | 7/2012 |
| EP | 2607712 A1 | 6/2013 |
| EP | 2040639 B1 | 2/2014 |
| EP | 1207934 B1 | 8/2014 |
| EP | 2662099 B1 | 9/2014 |
| EP | 2427230 B1 | 12/2014 |
| EP | 2396050 B1 | 1/2015 |
| EP | 2835141 A1 | 2/2015 |
| EP | 2840954 A1 | 3/2015 |
| EP | 2841122 A1 | 3/2015 |
| EP | 2841124 A1 | 3/2015 |
| EP | 2860849 A1 | 4/2015 |
| EP | 2868331 A2 | 5/2015 |
| EP | 2868332 A1 | 5/2015 |
| EP | 2999496 A2 | 3/2016 |
| EP | 3000492 A1 | 3/2016 |
| EP | 3000493 A1 | 3/2016 |
| EP | 3055922 A1 | 8/2016 |
| EP | 3062730 A1 | 9/2016 |
| EP | 3115070 A1 | 1/2017 |
| EP | 3127562 A1 | 2/2017 |
| EP | 2922486 B1 | 5/2017 |
| EP | 3216467 A1 | 9/2017 |
| EP | 3222302 A1 | 9/2017 |
| EP | 3236079 A1 | 10/2017 |
| EP | 3287154 A1 | 2/2018 |
| EP | 3287155 A1 | 2/2018 |
| EP | 3326567 A1 | 5/2018 |
| EP | 3329951 A1 | 6/2018 |
| EP | 3338825 A1 | 6/2018 |
| EP | 3205360 B1 | 8/2018 |
| EP | 3359214 A1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| EP | 3606575 A1 | 2/2020 |
| EP | 3737436 A1 | 11/2020 |
| EP | 3848089 | 7/2021 |
| EP | 3858421 A1 | 8/2021 |
| EP | 3897814 A1 | 10/2021 |
| EP | 4218899 A1 | 8/2023 |
| EP | 4252825 | 10/2023 |
| GB | 2239675 A | 7/1991 |
| GB | 2451161 A | 1/2009 |
| GB | 2504175 A | 1/2014 |
| GB | 2504177 A | 1/2014 |
| JP | 2003504091 A | 2/2003 |
| JP | 2004-202006 | 7/2004 |
| JP | 2009530041 A | 8/2009 |
| JP | 2012505038 A | 3/2012 |
| JP | 2012527269 A | 11/2012 |
| JP | 2015500666 A | 1/2015 |

(56) References Cited

FOREIGN PATENT DOCUMENTS

| | | |
|---|---|---|
| JP | 2015516267 A | 6/2015 |
| JP | 2016509950 A | 4/2016 |
| JP | 2018509223 A | 4/2018 |
| JP | 2018528804 A | 10/2018 |
| JP | 2018535727 A | 12/2018 |
| JP | 2020503083 A | 1/2020 |
| WO | 9001972 A1 | 3/1990 |
| WO | 90/13321 | 11/1990 |
| WO | 1994/01148 A1 | 1/1994 |
| WO | 99/34847 | 7/1999 |
| WO | 2001/083016 A2 | 5/2000 |
| WO | 2000043053 A1 | 7/2000 |
| WO | 0062838 A2 | 10/2000 |
| WO | 2002/070039 A2 | 3/2001 |
| WO | 2002/038085 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007081818 A2 | 7/2007 |
| WO | 2007112033 A2 | 10/2007 |
| WO | 2007127477 A2 | 11/2007 |
| WO | 2008005747 A2 | 1/2008 |
| WO | 2008005990 A2 | 1/2008 |
| WO | 2008055301 A1 | 5/2008 |
| WO | 2008104858 A2 | 9/2008 |
| WO | 2009010963 A2 | 1/2009 |
| WO | 2009046096 A1 | 4/2009 |
| WO | 2009046790 | 4/2009 |
| WO | 2009064879 A2 | 5/2009 |
| WO | 2009129481 A1 | 10/2009 |
| WO | 2010042546 | 4/2010 |
| WO | 2010063494 A1 | 6/2010 |
| WO | 2010105854 A1 | 9/2010 |
| WO | 2010127871 A1 | 11/2010 |
| WO | 2010133567 A1 | 11/2010 |
| WO | 2010150208 A2 | 12/2010 |
| WO | 2011035926 A1 | 3/2011 |
| WO | 2011047884 A1 | 4/2011 |
| WO | 2011076441 A1 | 6/2011 |
| WO | 2011089022 A1 | 7/2011 |
| WO | 2011160858 A1 | 12/2011 |
| WO | 2012007141 A1 | 1/2012 |
| WO | 2012094535 A2 | 7/2012 |
| WO | 2013032849 A1 | 3/2013 |
| WO | 2013070186 A1 | 5/2013 |
| WO | 2013093001 A2 | 6/2013 |
| WO | 2013119752 | 8/2013 |
| WO | 2013148697 A1 | 10/2013 |
| WO | 2013173239 A1 | 11/2013 |
| WO | 2013183060 A2 | 12/2013 |
| WO | 2014063119 | 4/2014 |
| WO | 2014141284 A2 | 9/2014 |
| WO | 2014164292 | 10/2014 |
| WO | 2015063277 A2 | 5/2015 |
| WO | 2015160943 A1 | 10/2015 |
| WO | 2015177793 A2 | 11/2015 |
| WO | 2016001218 A1 | 1/2016 |
| WO | 2016005803 A2 | 1/2016 |
| WO | 2016185473 A1 | 11/2016 |
| WO | 2016207293 A1 | 12/2016 |
| WO | 2017032751 | 3/2017 |
| WO | 2017053361 A1 | 3/2017 |
| WO | 2017060254 A1 | 4/2017 |
| WO | 2017081561 A1 | 5/2017 |
| WO | 2017137604 A1 | 8/2017 |
| WO | 2017147291 A1 | 8/2017 |
| WO | 2017159849 | 9/2017 |
| WO | 2017162618 | 9/2017 |
| WO | 2018033920 A1 | 2/2018 |
| WO | 2018045299 | 3/2018 |
| WO | 2018061001 A2 | 4/2018 |
| WO | 2018061002 A1 | 4/2018 |
| WO | 2018067410 A1 | 4/2018 |
| WO | 2018078615 A1 | 5/2018 |
| WO | 2018096531 A1 | 5/2018 |
| WO | 2018158636 A1 | 9/2018 |
| WO | 2018172848 A2 | 9/2018 |
| WO | 2018220589 A1 | 12/2018 |
| WO | 2018226991 A1 | 12/2018 |
| WO | 2018234454 A1 | 12/2018 |
| WO | 2019094963 A1 | 5/2019 |
| WO | 2019125899 A1 | 6/2019 |
| WO | 2019138350 A2 | 7/2019 |
| WO | 2019152875 A1 | 8/2019 |
| WO | 2019158996 A1 | 8/2019 |
| WO | 2019229223 A1 | 12/2019 |
| WO | 2020152611 A2 | 7/2020 |
| WO | 2021062265 | 4/2021 |
| WO | 2021152012 A1 | 8/2021 |
| WO | 2021159147 A1 | 8/2021 |
| WO | 2021198881 A1 | 10/2021 |
| WO | 2021205346 A2 | 10/2021 |
| WO | 2022189932 A1 | 9/2022 |
| WO | 2023014742 A1 | 2/2023 |
| WO | 2023062453 A1 | 4/2023 |
| WO | 2024057252 A1 | 3/2024 |
| WO | 2024057253 A2 | 3/2024 |
| WO | 2024057254 A1 | 3/2024 |
| WO | 2024057255 A2 | 3/2024 |
| WO | 2024057256 A2 | 3/2024 |
| WO | 2024057257 A2 | 3/2024 |
| WO | 2025141457 A1 | 7/2025 |

OTHER PUBLICATIONS

Corrected Notice of Allowability for U.S. Appl. No. 17/070,323 mailed Jun. 1, 2023.
Corrected Notice of Allowability for U.S. Appl. No. 17/180,041 mailed Jun. 30, 2023.
Examination Report for Indian Patent Application No. 202147033522 mailed May 24, 2023.
Extended Search Report and Preliminary Opinion for European Application No. 23159720.4 mailed Jun. 27, 2023.
Extended Search Report for European Application No. 22197511.3 mailed Dec. 5, 2022.
Extended Search Report for European Application No. 23159721.2 mailed Jun. 26, 2023.
Extended Search Report for European Application No. 23159724.6 mailed Jun. 26, 2023.
Extended Search Report for European Application No. 23159725.3 mailed Jun. 28, 2023.
Final Office Action for U.S. Appl. No. 16/952,327 mailed Jun. 8, 2023.
Final Office Action for U.S. Appl. No. 16/952,389 mailed Jul. 18, 2023.
Final Office Action for U.S. Appl. No. 16/952,444 mailed Jul. 5, 2023.
Final Office Action for U.S. Appl. No. 17/069,570 mailed Apr. 28, 2023.
Final Office Action for U.S. Appl. No. 17/070,670 mailed Jun. 2, 2023.
Final Office Action for U.S. Appl. No. 17/077,769 mailed Jun. 7, 2023.
International Search Report and Written Opinion from International Application No. PCT/IB2022/058101 mailed Feb. 20, 2023.
Issue Notification for U.S. Appl. No. 16/810,116 mailed May 17, 2023.
Non-Final Office Action for U.S. Appl. No. 17/069,570 mailed Oct. 2, 2023.
Non-Final Office Action for U.S. Appl. No. 17/078,439 mailed Jun. 1, 2023.
Non-Final Office Action for U.S. Appl. No. 17/078,472 mailed May 4, 2023.
Non-Final Office Action for U.S. Appl. No. 17/574,701 mailed Sep. 27, 2023.
Notice of Allowance for U.S. Appl. No. 16/275,559 mailed Jul. 27, 2023.

(56)          References Cited

OTHER PUBLICATIONS

Notice of Allowance for U.S. Appl. No. 16/810,116 mailed Mar. 13, 2023.
Notice of Allowance for U.S. Appl. No. 17/069,064 mailed Mar. 8, 2023.
Notice of Allowance for U.S. Appl. No. 17/070,323 mailed Aug. 30, 2023.
Notice of Allowance for U.S. Appl. No. 17/070,323 mailed May 15, 2023.
Notice of Allowance for U.S. Appl. No. 17/077,769 mailed Sep. 27, 2023.
Notice of Allowance for U.S. Appl. No. 17/173,944 mailed Jul. 10, 2023.
Notice of Allowance for U.S. Appl. No. 17/180,041 mailed Jun. 13, 2023.
Notice of Allowance for U.S. Appl. No. 17/180,041 mailed Sep. 18, 2023.
Notice of Allowance for U.S. Appl. No. 17/182,482 mailed Apr. 21, 2023.
Office Action for Canadian Application No. 3,039,285 mailed Mar. 24, 2023.
Office Action for Canadian Application No. 3,080,800 mailed Sep. 12, 2023.
Office Action for Canadian Application No. 3,122,415 mailed Mar. 31, 2023.
Office Action for Chinese Application No. 201980007116.9 mailed Nov. 28, 2022.
Office Action for Japanese Application No. 2019-521643 mailed Apr. 11, 2023.
Office Action for Japanese Application No. 2020-537746 mailed Feb. 21, 2023.
U.S. Appl. No. 18/121,995, filed Mar. 15, 2023.
U.S. Appl. No. 18/122,456, filed Mar. 16, 2023.
U.S. Appl. No. 18/122,486, filed Mar. 16, 2023.
U.S. Appl. No. 18/122,504, filed Mar. 16, 2023.
U.S. Appl. No. 18/447,025, filed Aug. 9, 2023.
U.S. Appl. No. 18/447,050, filed Aug. 9, 2023.
U.S. Appl. No. 18/447,064, filed Aug. 9, 2023.
U.S. Appl. No. 18/447,074, filed Aug. 9, 2023.
U.S. Appl. No. 18/447,086, filed Aug. 9, 2023.
U.S. Appl. No. 63/158,708, filed Mar. 9, 2021.
U.S. Appl. No. 63/254,321, filed Oct. 11, 2021.
U.S. Appl. No. 63/317,199, filed Mar. 7, 2022.
Corrected Notice of Allowability for U.S. Appl. No. 16/279,352 mailed Nov. 3, 2021.
Corrected Notice of Allowability for U.S. Appl. No. 16/281,237 mailed Mar. 31, 2021.
Corrected Notice of Allowability for U.S. Appl. No. 16/810,121 mailed Jun. 28, 2022.
Corrected Notice of Allowability for U.S. Appl. No. 16/810,121 mailed Sep. 20, 2022.
Corrected Notice of Allowability for U.S. Appl. No. 16/810,172 mailed Feb. 2, 2022.
Examination Report for Australian Patent Application No. 2017349920 issued on Jun. 2, 2022.
Examination Report for Indian Patent Application No. 202047017397 issued on May 4, 2022.
Examination Report for Indian Patent Application No. 201917018651 mailed Jun. 30, 2021.
Extended European Search Report for EP Patent Application No. 22163640.0 mailed Jun. 29, 2022.
Extended European Search Report for European Application No. 21208803.3 issued on Apr. 13, 2022.
Extended European Search Report for European Application No. 21209256.3 issued on Mar. 2, 2022.
Extended Search Report for European Application No. 19172327.9 mailed Aug. 23, 2019.
Extended Search Report for European Application No. 20159714.3 mailed Jul. 3, 2020.

Extended Search Report for European Application No. 20159716.8 mailed Jul. 3, 2020.
Extended Search Report for European Application No. 20159718.4 mailed Jul. 9, 2020.
Extended Search Report for European Application No. 20195082.1 mailed Nov. 5, 2020.
Extended Search Report for European Application No. 20195084.7 mailed Nov. 5, 2020.
Extended Search Report for European Application No. 20195085.4 mailed Nov. 4, 2020.
Extended Search Report for European Application No. 20195987.1 mailed Nov. 5, 2020.
Extended Search Report for European Application No. 21156647.6 mailed May 21, 2021.
Extended Search Report for European Application No. 21158196.2 mailed Apr. 8, 2021.
Extended Search Report for European Application No. 21158902.3 mailed Apr. 29, 2021.
Extended Search Report for European Application No. 21158903.1 mailed Apr. 9, 2021.
Final Office Action for U.S. Appl. No. 16/275,559 mailed Jan. 4, 2021.
Final Office Action for U.S. Appl. No. 16/275,559 mailed May 17, 2022.
Final Office Action for U.S. Appl. No. 16/275,559 mailed Oct. 20, 2021.
Final Office Action for U.S. Appl. No. 16/276,965 mailed Apr. 13, 2021.
Final Office Action for U.S. Appl. No. 16/277,411 mailed Jun. 21, 2021.
Final Office Action for U.S. Appl. No. 16/279,352 mailed May 3, 2021.
Final Office Action for U.S. Appl. No. 17/069,064 mailed May 25, 2022.
International Search Report and Written Opinion from International Application No. PCT/IB2020/050515 mailed Sep. 9, 2020.
International Search Report and Written Opinion from International Application No. PCT/IB2021/052590 mailed Sep. 14, 2021.
International Search Report and Written Opinion from International Application No. PCT/IB2021/052857 mailed Oct. 5, 2021.
International Search Report and Written Opinion from International Application No. PCT/IL2017/051158 mailed Jan. 17, 2018.
International Search Report and Written Opinion from International Application No. PT/IB2019/050186 mailed Jul. 18, 2019.
Invitation to Pay Additional Fees for International Application No. PCT/IB2020/050515 mailed Mar. 31, 2020.
Invitation to Pay Additional Fees for International Application No. PCT/IB2021/052590 mailed Jul. 23, 2021.
Invitation to Pay Additional Fees for International Application No. PCT/IB2021/052857 mailed Jul. 7, 2021.
Issue Notification for U.S. Appl. No. 16/276,965 mailed Mar. 16, 2022.
Issue Notification for U.S. Appl. No. 16/277,411 mailed Feb. 9, 2022.
Issue Notification for U.S. Appl. No. 16/278,482 mailed Jan. 13, 2021.
Issue Notification for U.S. Appl. No. 16/279,352 mailed Nov. 10, 2021.
Issue Notification for U.S. Appl. No. 16/280,566 mailed Nov. 10, 2021.
Issue Notification for U.S. Appl. No. 16/281,237 mailed Apr. 14, 2021.
Issue Notification for U.S. Appl. No. 16/281,264 mailed Dec. 16, 2020.
Issue Notification for U.S. Appl. No. 16/750,354 mailed Nov. 17, 2021.
Issue Notification for U.S. Appl. No. 16/810,086 mailed Mar. 9, 2022.
Issue Notification for U.S. Appl. No. 16/810,172 mailed Mar. 23, 2022.
Issue Notification for U.S. Appl. No. 17/069,321 mailed Mar. 16, 2022.

(56)        References Cited

OTHER PUBLICATIONS

Non-Final Office Action for U.S. Appl. No. 16/275,559 mailed Jan. 26, 2022.
Non-Final Office Action for U.S. Appl. No. 16/275,559 mailed May 26, 2021.
Non-Final Office Action for U.S. Appl. No. 16/275,559 mailed Sep. 4, 2020.
Non-Final Office Action for U.S. Appl. No. 16/276,965 mailed Jul. 26, 2021.
Non-Final Office Action for U.S. Appl. No. 16/276,965 mailed Jun. 19, 2020.
Non-Final Office Action for U.S. Appl. No. 16/276,965 mailed Nov. 30, 2020.
Non-Final Office Action for U.S. Appl. No. 16/277,411 mailed Feb. 9, 2021.
Non-Final Office Action for U.S. Appl. No. 16/278,482 mailed Jun. 23, 2020.
Non-Final Office Action for U.S. Appl. No. 16/279,352 mailed Nov. 10, 2020.
Non-Final Office Action for U.S. Appl. No. 16/280,566 mailed Dec. 21, 2020.
Non-Final Office Action for U.S. Appl. No. 16/281,237 mailed Aug. 21, 2020.
Non-Final Office Action for U.S. Appl. No. 16/281,264 mailed Jun. 29, 2020.
Non-Final Office Action for U.S. Appl. No. 16/810,121 mailed Mar. 9, 2022.
Non-Final Office Action for U.S. Appl. No. 17/069,064 mailed Dec. 9, 2021.
Non-Final Office Action for U.S. Appl. No. 17/069,321 mailed Nov. 18, 2021.
Non-Final Office Action for U.S. Appl. No. 17/176,344 mailed Apr. 20, 2022.
Notice of Allowance for U.S. Appl. No. 16/276,965 mailed Jan. 26, 2022.
Notice of Allowance for U.S. Appl. No. 16/277,411 mailed Dec. 8, 2021.
Notice of Allowance for U.S. Appl. No. 16/278,482 mailed Dec. 2, 2020.
Notice of Allowance for U.S. Appl. No. 16/279,352 mailed Oct. 1, 2021.
Notice of Allowance for U.S. Appl. No. 16/280,566 mailed Aug. 31, 2021.
Notice of Allowance for U.S. Appl. No. 16/281,237 mailed Feb. 1, 2021.
Notice of Allowance for U.S. Appl. No. 16/281,264 mailed Nov. 12, 2020.
Notice of Allowance for U.S. Appl. No. 16/750,354 mailed Oct. 18, 2021.
Notice of Allowance for U.S. Appl. No. 16/810,086 mailed Jan. 7, 2022.
Notice of Allowance for U.S. Appl. No. 16/810,121 mailed Aug. 19, 2022.
Notice of Allowance for U.S. Appl. No. 16/810,121 mailed Jun. 1, 2022.
Notice of Allowance for U.S. Appl. No. 16/810,172 mailed Jan. 10, 2022.
Notice of Allowance for U.S. Appl. No. 16/810,270 mailed Apr. 14, 2022.
Notice of Allowance for U.S. Appl. No. 16/810,270 mailed Jul. 22, 2022.
Notice of Allowance for U.S. Appl. No. 17/069,321 mailed Feb. 2, 2022.
Office Action for Chinese Application No. 201780066201.3 mailed Jun. 29, 2021.
Office Action for Japanese Patent Application No. 2019-521643 mailed Sep. 28, 2021.
Restriction Requirement for U.S. Appl. No. 16/275,559 mailed Jun. 2, 2020.

Restriction Requirement for U.S. Appl. No. 16/279,352 mailed Aug. 11, 2020.
Restriction Requirement for U.S. Appl. No. 16/280,566 mailed Aug. 11, 2020.
Restriction Requirement for U.S. Appl. No. 16/810,116 mailed Jun. 29, 2022.
Supplemental Notice of Allowability for U.S. Appl. No. 16/276,965 mailed Mar. 10, 2022.
Supplemental Notice of Allowability for U.S. Appl. No. 16/276,965 mailed Mar. 2, 2022.
Supplemental Notice of Allowability for U.S. Appl. No. 16/278,482 mailed Dec. 24, 2020.
Supplemental Notice of Allowability for U.S. Appl. No. 16/279,352 mailed Oct. 21, 2021.
U.S. Appl. No. 14/567,439, filed Dec. 11, 2014.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,482, filed Feb. 18, 2019.
U.S. Appl. No. 16/279,352, filed Feb. 19, 2019.
U.S. Appl. No. 16/280,566, filed Feb. 20, 2019.
U.S. Appl. No. 16/281,237, filed Feb. 21, 2019.
U.S. Appl. No. 16/281,264, filed Feb. 21, 2019.
U.S. Appl. No. 16/750,354, filed Jan. 23, 2020.
U.S. Appl. No. 16/810,086, filed Mar. 5, 2020.
U.S. Appl. No. 16/810,121, filed Mar. 5, 2020.
U.S. Appl. No. 16/952,327, filed Nov. 19, 2020.
U.S. Appl. No. 16/952,389, filed Nov. 19, 2020.
U.S. Appl. No. 16/952,444, filed Nov. 19, 2020.
U.S. Appl. No. 17/069,064, filed Oct. 13, 2020.
U.S. Appl. No. 17/069,321, filed Oct. 13, 2020.
U.S. Appl. No. 17/069,570, filed Oct. 13, 2020.
U.S. Appl. No. 17/070,323, filed Oct. 14, 2020.
U.S. Appl. No. 17/070,670, filed Oct. 14, 2020.
U.S. Appl. No. 17/077,769, filed Oct. 22, 2020.
U.S. Appl. No. 17/078,439, filed Oct. 23, 2020.
U.S. Appl. No. 17/078,472, filed Oct. 23, 2020.
U.S. Appl. No. 17/176,344, filed Feb. 16, 2021.
U.S. Appl. No. 17/177,296, filed Feb. 17, 2021.
U.S. Appl. No. 17/180,041, filed Feb. 19, 2021.
U.S. Appl. No. 17/182,482, filed Feb. 23, 2021.
U.S. Appl. No. 17/528,015, filed Nov. 16, 2021.
U.S. Appl. No. 17/528,807, filed Nov. 17, 2021.
U.S. Appl. No. 17/532,318, filed Nov. 22, 2021.
U.S. Appl. No. 17/574,701, filed Jan. 13, 2022.
U.S. Appl. No. 17/609,589, filed Nov. 8, 2021.
U.S. Appl. No. 17/677,571, filed Feb. 22, 2022.
U.S. Appl. No. 17/678,122, filed Feb. 23, 2022.
U.S. Appl. No. 17/857,402, filed Jul. 5, 2022.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,718, filed May 2, 2018.
U.S. Appl. No. 62/681,868, filed Jun. 7, 2018.
U.S. Appl. No. 62/727,605, filed Sep. 6, 2018.
U.S. Appl. No. 62/796,138, filed Jan. 24, 2019.
U.S. Appl. No. 62/851,716, filed May 23, 2019.
U.S. Appl. No. 62/870,821, filed Jul. 5, 2019.
U.S. Appl. No. 62/896,026, filed Sep. 5, 2019.
U.S. Appl. No. 63/003,955, filed Apr. 2, 2020.
U.S. Appl. No. 63/006,122, filed Apr. 7, 2020.
U.S. Appl. No. 63/114,136, filed Nov. 16, 2020.
U.S. Appl. No. 63/129,983, filed Dec. 23, 2020.

(56) References Cited

OTHER PUBLICATIONS

"Tanslation of decision of Board 4 (Nullity Board) of the German Federal Patent Court re German patent 10336902", pronounced Nov. 15, 2016, and appendices to decision, 62 pages.

Agarwal , et al., "Newer-generation ventricular assist devices.", Best Practice & Research Clinical Anaesthesiology, 2012, pp. 117-130.

Alba , et al., "The future is here: ventricular assist devices for the failing heart", Expert review of cardiovascular therapy, 2009, pp. 1067-1077.

Bai , et al., "A Split-Array, C-2C Switched-Capacitor Power Amplifier in 65 nm CMOS", IEEE Radio Frequency Integrated Circuits Symposium, 2017, pp. 336-339.

Burnett , et al., "Renal Interstitial Pressure And Sodium Excretion During Renal Vein Constriction", American Physiological Society, 1980, pp. F279-F282.

Cassidy , et al., "The Conductance vol. Catheter Technique for Measurement of Left Ventricular Volume in Young Piglets", Pediatric Research, 1992, pp. 85-90.

Coxworth , "Artificial Vein Valve Could Replace Drugs For Treating Common Circulatory Problem", Published on Gizmag website (http://www.gizmag.com/artificial-venous-valve-cvi/21785/), Mar. 9, 2012.

Damman , et al., "Decreased Cardiac Output, Venous Congestion And The Association With Renal Impairment In Patients With Cardiac Dysfunction", European Journal of Heart Failure, 2007, pp. 872-878.

Damman , et al., "Increased Central Venous Pressure Is Associated With Impaired Renal Function And Mortality In A Broad Spectrum Of Patients With Cardiovascular Disease", Journal of American College of Cardiology, 2009, pp. 582-588.

Doty , et al., "The Effect Of Increased Renal Venous Pressure On Renal Function", The Journal of Trauma,, Dec. 1999, pp. 1000-1003.

Felker , et al., "Anemia As A Risk Factor And Therapeutic Target In Heart Failure", Journal of the American College of Cardiology, 2004, pp. 959-966.

Firth , et al., "Raised Venous Pressure: A Direct Cause Of Sodium Retention In Oedema?", The Lancet, May 7, 1988, pp. 1033-1036.

Forman , et al., "Incidence, Predictors At Admission, And Impact Of Worsening Renal Function Among Patients Hospitalized With Heart Failure", Journal of American College of Cardiology, 2004, pp. 61-67.

Fraser, et al., "The use of computational fluid dynamics in the development of ventricular assist devices", Medical engineering & physics, 2011, pp. 263-280.

Frazier, et al., "First Human Use of the Hemopump, a Catheter Mounted Ventricular Assist Device", Ann Thorac Surg, 1990, pp. 299-304.

Gomes , et al., "Heterologous Valve Implantation In The Infra-Renal Vena Cava For Treatment Of The Iliac Venous Valve Regurgitation Disease: Experimental Study", Rev Bras Cir Cardiovasc, 2002, pp. 367-369.

Haddy , et al., "Effect Of Elevation Of Intraluminal Pressure On Renal Vascular Resistance", Circulation Research Journal Of The American Heart Association, 1956, pp. 659-663.

Heywood , et al., "High Prevalence Of Renal Dysfunction And Its Impact On Outcome In 118,465 Patients Hospitalized With Acute Decompensated Heart Failure: A Report From The ADHERE Database", Journal of Cardiac Failure, 2007, pp. 422-430.

Hillege , et al., "Renal Function As A Predictor Of Outcome In A Broad Spectrum Of Patients With Heart Failure", Circulation Journal of the American Heart Association, 2006, pp. 671-678.

Hillege , et al., "Renal Function, Neurohormonal Activation, And Survival In Patients With Chronic Heart Failure", Circulation Journal of the American Heart Association, 2000, pp. 203-210.

Hsu , et al., "Review of recent patents on foldable ventricular assist devices", Recent Patents on Biomedical Engineering, 2012, pp. 208-222.

IKARI , "The Physics Of Guiding Catheter; The IKARI Guiding Catheter In TRI", available at httu:i /www.docstoc.com/docs/ 148136553/The-[KARI-catheter---anovel-guide-for-TRI--.

Kafagy , et al., "Design of axial blood pumps for patients with dysfunctional fontan physiology: computational studies and performance testing", Artificial organs, 2015, pp. 34-42.

Kang , et al., "Fluid dynamics aspects of miniaturized axial-flow blood pump", Bio-medical materials and engineering, 2014, pp. 723-729.

Koochaki , et al., "A new design and computational fluid dynamics study of an implantable axial blood pump", Australasian Physical & Engineering Sciences in Medicine, 2013, pp. 417-422.

Lauten , et al., "Heterotopic Transcatheter Tricuspid Valve Implantation: First-In-Man Application Of A Novel Approach To Tricuspid Regurgitation", European Heart Journal, Feb. 15, 2011, pp. 1207-1213.

Mcalister , et al., "Renal Insufficiency And Heart Failure: Prognostic And Therapeutic Implications From A Prospective Cohort Study", Circulation Journal of the American Heart Association, 2004, pp. 1004-1009.

Meyns , et al., "The Heart-Hemopump Interaction: A Study of Hemopump Flow as a Function of Cardiac Activity", Artificial Organs, 1996, pp. 641-649.

Mullens , et al., "Elevated Intra-Abdominal Pressure In Acute Decompensated Heart Failure. A Potential Contributor To Worsening Renal Function", Journal of the American College of Cardiology, 2008, pp. 300-306.

Mullens , et al., "Importance Of Venous Congestion For Worsening Of Renal Function In Advanced Decompensated Heart Failure", Journal of American College of Cardiology, 2009, pp. 589-596.

Mullens , et al., "Prompt Reduction In Intra-Abdominal Pressure Following Large-Volume Mechanical Fluid Removal Improves Renal Insufficiency In Refractory Decompensated Heart Failure", Journal of Cardiac Failure, 2008, pp. 508-514.

Notarius , et al., "Central Venous Pressure During Exercise: Role Of Muscle Pump", Canadian Journal of Physiology and Pharmacology, 1996, pp. 647-651.

Park , et al., "Nutcracker Syndrome: Intravascular Stenting Approach", Nephrol Dial Transplant, 2000, pp. 99-101.

Reul , et al., "Blood pumps for circulatory support", Perfusion-Sevenoaks, 2000, pp. 295-312.

Reul , et al., "Rotary blood pumps in circulatory assist", Perfusion, May 1995, pp. 153-158.

Rodefeld , "Cavopulmonary assist for the univentricular Fontan circulation: von Karman viscous impeller pump", The Journal of Thoracic and Cardiovascular Surgery, 2010, pp. 529-536.

Schmitz-Rode , et al., "An Expandable Percutaneous Catheter Pump For Left Ventricular Support", Journal of the American College of Cardiology, 2005, pp. 1856-1861.

Schmitz-Rode , et al., "Axial flow catheter pump for circulatory support", Biomed Tech (Berl), 2002, pp. 142-143.

Semple , et al., "Effect Of Increased Renal Venous Pressure On Circulatory "Autoregulation" Of Isolated Dog Kidneys", Circulation Research Journal of The American Heart Association, 1959, pp. 643-648.

Sianos , et al., "The Recover® LP 2.5 catheter-mounted left ventricular assist device", EuroIntervention, 2006, pp. 116-119.

Siess , et al., "Concept, realization, and first in vitro testing of an intraarterial microaxial blood pump", Artificial Organs, 1995, pp. 644-652.

Siess , et al., "Hemodynamic system analysis of intraarterial microaxial pumps in vitro and in vivo", Artificial Organs, Jun. 1996, pp. 650-661.

Siess , "PhD Chapter 3—English translation", https://www.shaker. eu/en/content/catalogue/index.asp?lang=en&ID=8&ISBN=978-3-8265-6150-4&search=yes.

Song , et al., "Axial flow blood pumps", ASAIO journal, 2003, pp. 355-364.

Tang , et al., "Anemia In Chronic Heart Failure: Prevalence, Etiology, Clinical Correlates, And Treatment Options", Circulation Journal of the American Heart Association, 2006, pp. 2454-2461.

(56) References Cited

OTHER PUBLICATIONS

Throckmorton , et al., "Design of a protective cage for an intra vascular axial flow blood pump to mechanically assist the failing Fontan", Artificial organs, 2009, pp. 611-621.

Throckmorton , et al., "Mechanical Cavopulmonary Assist for the Univentricular Fontan Circulation Using a Novel Folding Propeller Blood Pump", ASAIO Journal, 2007, pp. 734-741.

Thunberg , et al., "Ventricular assist devices today and tomorrow", Journal of cardiothoracic and vascular anesthesia, 2010, pp. 656-680.

TIMMS , "A review of clinical ventricular assist devices", Medical engineering & physics, 2011, pp. 1041-1047.

Triep , et al., "Computational Fluid Dynamics and Digital Particle Image Velocimetry Study of the Flow Through an Optimized Micro-axial Blood Pump", Artificial Organs, May 2006, pp. 384-391.

Uthoff , et al., "Central venous pressure at emergency room presentation predicts cardiac rehospitalization in patients with decompensated heart failure", European Journal of Heart Failure, 2010, pp. 469-476.

Van Mieghem , et al., "Design and Principle of Operation of the HeartMate PHPTM (Percutaneous Heart Pump)", EuroIntervention, 2016.

Vercaemst , et al., "Impella: A Miniaturized Cardiac Support System in an Era of Minimal Invasive Cardiac Surgery", Presented at the 39th International Conference of the American Society of Extra-Corporeal Technology, Mar. 22-25, 2001.

Wampler , "The first co-axial flow pump for human use: the Hemopump", Flameng W. (eds) Temporary Cardiac Assist with an Axial Pump System, 1991.

Wencker , "Acute Cardio-Renal Syndrome: Progression From Congestive Heart Failure To Congestive Kidney Failure", Current Heart Failure Reports, 2007, pp. 134-138.

Winton , "The Control Of Glomerular Pressure By Vascular Changes Within The Mammalian Kidney, Demonstrated By The Actions Of Adrenaline", Journal of Physiology, Nov. 1931, pp. 151-162.

Winton , "The Influence Of Venous Pressure On The Isolated Mammalian Kidney", Journal of Physiology, Jun. 6, 1931, pp. 49-61.

Wood , "The Mechanism Of The Increased Venous Pressure With Exercise In Congestive Heart Failure", Journal of Clinical Investigation, 1962, pp. 2020-2024.

Wu , et al., "Design and simulation of axial flow maglev blood pump", International Journal of Information Engineering and Electronic Business, 2011, p. 42.

Yancy , et al., "Clinical Presentation, Management, And In-Hospital Outcomes Of Patients Admitted With Acute Decompensated Heart Failure With Preserved Systolic Function. A Report From The Acute Decompensated Heart Failure National Registry (ADHERE) Database", Journal of the American College of Cardiology, 2006, pp. 76-84.

Corrected Notice of Allowability for U.S. Appl. No. 17/182,482 mailed Feb. 7, 2023.

Examination Report for Australian Patent Application No. 2017349920 mailed Nov. 4, 2022.

Extended European Search Report for European Application No. 22155936.2 mailed Jul. 8, 2022.

Extended European Search Report for European Application No. 22163648.3 mailed Aug. 10, 2022.

Extended European Search Report for European Application No. 22163653.3 mailed Jul. 1, 2022.

Final Office Action for U.S. Appl. No. 17/176,344 mailed Oct. 12, 2022.

International Search Report and Written Opinion from International Application No. PCT/IB2022/051990 mailed Aug. 10, 2022.

Invitation to Pay Additional Fees for International Application No. PCT/IB2022/051990 mailed May 13, 2022.

Issue Notification for U.S. Appl. No. 16/810,270 mailed Oct. 12, 2022.

Non-Final Office Action for U.S. Appl. No. 16/275,559 mailed Jan. 19, 2023.

Non-Final Office Action for U.S. Appl. No. 16/952,327 mailed Nov. 8, 2022.

Non-Final Office Action for U.S. Appl. No. 16/952,389 mailed Dec. 21, 2022.

Non-Final Office Action for U.S. Appl. No. 16/952,444 mailed Jan. 6, 2023.

Non-Final Office Action for U.S. Appl. No. 17/069,064 mailed Nov. 7, 2022.

Non-Final Office Action for U.S. Appl. No. 17/069,570 mailed Oct. 6, 2022.

Non-Final Office Action for U.S. Appl. No. 17/070,323 mailed Oct. 6, 2022.

Non-Final Office Action for U.S. Appl. No. 17/070,670 mailed Oct. 5, 2022.

Non-Final Office Action for U.S. Appl. No. 17/077,769 mailed Oct. 5, 2022.

Non-Final Office Action for U.S. Appl. No. 17/180,041 mailed Jan. 31, 2023.

Notice of Allowance for U.S. Appl. No. 17/182,482 mailed Jan. 5, 2023.

Office Action for Japanese Application No. 2019-521643 mailed May 10, 2022.

Office Action for Japanese Application No. 2019-521643 mailed Oct. 27, 2022.

Third Party Submission received during the prosecution of U.S. Appl. No. 17/078,439 on Sep. 28, 2022.

"Compendium of Technical and Scientific Information for the Hemopump Temporary Cardiac Assist System", Johnson & Johnson Interventional Systems, 1988, pp. 1-15.

Achour , et al., "Mechanical Left Ventricular Unloading Prior to Reperfusion Reduces Infarct Size in a Canine Infarction Model", Catheterization and Cardiovascular Interventions 64, 2005, pp. 182-192.

Butler , et al., "The Hemopump—A New Cardiac Prothesis Device", Reprinted from IEEE Transactions on Biomedical Engineering, vol. 37, No. 2, Feb. 1990, pp. 192-195.

Chan , et al., "Rapid manufacturing techniques in the development of an axial blood pump impeller", Proc. Instn Mech. Engrs vol. 217 Part H: J. Engineering in Medicine, 2003, pp. 469-475.

Dekker , et al., "Efficacy of a New Intraaortic Propeller Pump vs the Intraaortic Balloon Pump", Chest, vol. 123, Issue 6, Jun. 2003, pp. 2089-2095.

Flameng , "Temporary Cardiac Assist with an Axial Pump System", Steinkopff Verlag Darmstadt, 1991, 79 pages.

Frazier , et al., "Treatment of Cardiac Allograft Failure by use of an IntraAortic Axial Flow Pump", Journal of Heart Transplantation, St. Louis, vol. 9, No. 4, pp. 408-414, Jul. 1990.

Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.

Merhige , et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.

Roundtree , et al., "The Hemopump Cardiac Assist System: Nursing Care of the Patient", Reprinted from Critical Care Nurse, Apr. 1991.

Scholz , et al., "Mechanical left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.

Siess , "System Analysis and Development of Intravascular Rotation Pumps for Cardiac Assist", Helmholtz-Institute—Chapter 3, Jun. 1998, 17 pages.

Smalling , et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a

(56) References Cited

OTHER PUBLICATIONS

Canine Infarction Model, Presented in part at the American College of Cardiology 38th Annual Scientific Session, Mar. 1990, pp. 1152-1160.

Smalling , et al., "The Hemopump: A transvalvular, axial flow, left ventricular assist device", Coronary Artery Disease, Circulatory support devices in clinical cardiology, vol. 2 No. 6, pp. 666-671, Aug. 1991.

Smalling , et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.

Tamareille , et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.

Wampler , "Newsweek", Captain Hemo, May 16, 1988, 3 pages.

Wampler , "THI Today", Captain Hemo, Summer 1988, 2 pages.

Wampler , "Time Magazine", Captain Hemo, May 1988, 2 pages.

Wampler , et al., "Treatment of Cardiogenic Shock With the Hemopump Left Ventricular Assist Device", Annual of Thoracic Surgery, vol. 52, pp. 560-513, 1991.

Wampler , "U.S. News & World Report", Captain Hemo, pp. 1-2, May 16, 1988.

Corrected Notice of Allowance for U.S. Appl. No. 16/952,389 mailed Feb. 20, 2024.

Corrected Notice of Allowance for U.S. Appl. No. 16/952,389 mailed Mar. 4, 2024.

Corrected Notice of Allowance for U.S. Appl. No. 16/952,444 mailed Mar. 13, 2024.

Corrected Notice of Allowance for U.S. Appl. No. 17/069,570 mailed Apr. 10, 2024.

Corrected Notice of Allowance for U.S. Appl. No. 17/069,570 mailed Jul. 16, 2024.

Examination Report for European Application No. 21158196.2 mailed May 28, 2024.

Examination Report for European Application No. 21158903.1 mailed Jul. 9, 2024.

Examination Report for European Application No. 21718229.4 mailed Mar. 17, 2022.

Extended Search Report for European Application No. 24170573.0 mailed Jul. 29, 2024.

Final Office Action for U.S. Appl. No. 17/078,472 mailed Aug. 9, 2024.

Final Office Action for U.S. Appl. No. 17/176,344 mailed Apr. 12, 2024.

Final Office Action for U.S. Appl. No. 17/528,807 mailed Apr. 24, 2024.

Hearing Notice for Indian Application No. 202147033522 mailed Jul. 24, 2024.

International Search Report and Written Opinion from International Application No. PCT/IB2023/059136 mailed Jan. 2, 2024.

International Search Report and Written Opinion from International Application No. PCT/IB2023/059137 mailed Mar. 21, 2024.

International Search Report and Written Opinion from International Application No. PCT/IB2023/059138 mailed Feb. 7, 2024.

International Search Report and Written Opinion from International Application No. PCT/IB2023/059141 mailed Mar. 22, 2024.

International Search Report and Written Opinion from International Application No. PCT/IB2023/059142 mailed Apr. 16, 2024.

International Search Report and Written Opinion from International Application No. PCT/IB2023/059143 mailed Mar. 14, 2024.

Invitation to Pay Additional Fees for International Application No. PCT/IB2023/059134 mailed Dec. 21, 2023.

Invitation to Pay Additional Fees for International Application No. PCT/IB2023/059137 mailed Jan. 2, 2024.

Invitation to Pay Additional Fees for International Application No. PCT/IB2023/059138 mailed Dec. 8, 2023.

Invitation to Pay Additional Fees for International Application No. PCT/IB2023/059141 mailed Dec. 22, 2023.

Invitation to Pay Additional Fees for International Application No. PCT/IB2023/059142 mailed Jan. 2, 2024.

Issue Notification for U.S. Appl. No. 16/952,389 mailed Mar. 13, 2024.

Issue Notification for U.S. Appl. No. 16/952,444 mailed Mar. 20, 2024.

Issue Notification for U.S. Appl. No. 17,574,701 mailed Aug. 28, 2024.

Issue Notification for U.S. Appl. No. 17/078,439 mailed Apr. 3, 2024.

Issue Notification for U.S. Appl. No. 17/173,944 mailed Jun. 12, 2024.

Issue Notification for U.S. Appl. No. 17/177,296 mailed Mar. 13, 2024.

Non-Final Office Action for U.S. Appl. No. 17/078,472 mailed Feb. 14, 2024.

Non-Final Office Action for U.S. Appl. No. 17/532,318 mailed Jul. 18, 2024.

Non-Final Office Action for U.S. Appl. No. 17/609,589 mailed Jul. 1, 2024.

Non-Final Office Action for U.S. Appl. No. 17/677,571 mailed Aug. 15, 2024.

Non-Final Office Action for U.S. Appl. No. 17/682,073 mailed Aug. 29, 2024.

Notice of Allowance for U.S. Appl. No. 16/952,327 mailed Apr. 29, 2024.

Notice of Allowance for U.S. Appl. No. 16/952,327 mailed Aug. 6, 2024.

Notice of Allowance for U.S. Appl. No. 16/952,444 mailed Feb. 15, 2024.

Notice of Allowance for U.S. Appl. No. 17/069,570 mailed Jun. 24, 2024.

Notice of Allowance for U.S. Appl. No. 17/069,570 mailed Mar. 13, 2024.

Notice of Allowance for U.S. Appl. No. 17/070,670 mailed Jun. 13, 2024.

Notice of Allowance for U.S. Appl. No. 17/078,439 mailed Feb. 27, 2024.

Notice of Allowance for U.S. Appl. No. 17/173,944 mailed Mar. 6, 2024.

Notice of Allowance for U.S. Appl. No. 17/177,296 mailed Feb. 14, 2024.

Notice of Allowance for U.S. Appl. No. 17/574,701 mailed Jun. 26, 2024.

Notice of Missing Requirements for U.S. Appl. No. 18/447,025 mailed Feb. 1, 2024.

Office Action for Japanese Application No. 2023-156391 mailed Jun. 3, 2024.

U.S. Appl. No. 18/444,972, filed Feb. 19, 2024.

U.S. Appl. No. 18/632,533, filed Apr. 11, 2024.

U.S. Appl. No. 18/632,545, filed Apr. 11, 2024.

U.S. Appl. No. 18/632,557, filed Apr. 11, 2024.

U.S. Appl. No. 18/632,569, filed Apr. 11, 2024.

U.S. Appl. No. 18/635,275, filed Apr. 15, 2024.

U.S. Appl. No. 18/635,286, filed Apr. 15, 2024.

U.S. Appl. No. 18/635,292, filed Apr. 15, 2024.

U.S. Appl. No. 18/637,653, filed Apr. 17, 2024.

U.S. Appl. No. 18/637,655, filed Apr. 17, 2024.

U.S. Appl. No. 18/637,667, filed Apr. 17, 2024.

U.S. Appl. No. 18/639,079, filed Apr. 18, 2024.

U.S. Appl. No. 18/639,087, filed Apr. 18, 2024.

U.S. Appl. No. 18/639,094, filed Apr. 18, 2024.

U.S. Appl. No. 18/639,098, filed Apr. 18, 2024.

U.S. Appl. No. 18/640,222, filed Apr. 19, 2024.

U.S. Appl. No. 18/640,260, filed Apr. 19, 2024.

U.S. Appl. No. 18/640,285, filed Apr. 19, 2024.

U.S. Appl. No. 18/640,303, filed Apr. 19, 2024.

U.S. Appl. No. 18/652,930, filed May 2, 2024.

U.S. Appl. No. 18/652,956, filed May 2, 2024.

U.S. Appl. No. 18/652,959, filed May 2, 2024.

U.S. Appl. No. 18/652,962, filed May 2, 2024.

(56) References Cited

OTHER PUBLICATIONS

U.S. Appl. No. 18/654,336, filed May 3, 2024.
U.S. Appl. No. 63/406,427, filed Sep. 14, 2022.
U.S. Appl. No. 63/432,496, filed Dec. 14, 2022.
U.S. Appl. No. 63/443,519, filed Feb. 6, 2023.
U.S. Appl. No. 63/470,259, filed Jun. 1, 2023.
"Peripheral Interventions 2015 Product Catalog", Boston Scientific, 2015, 7 pages.
Alsafarr, et al., "Hydrodynamic Effects on Flow Through Screens at Intakes", Water Research vol. 8, Issue 9, Sep. 1974, pp. 617-622.
Brückler, et al., "Flow Design and Optimization of a Percutaneously Implantable Miniature Blood Pump", Medical technology in cardiology, 2002, 11 pages.
Chang, et al., "Leveraging Device-Arterial Coupling to Determine Cardiac and Vascular State", IEEE Transactions on Biomedical Engineering, vol. 66, No. 10, Oct. 2019, pp. 2800-2808.
Kapur, et al., "Mechanical Left Ventricular Unloading to Reduce Infarct Size During Acute Myocardial Infarction: Insight from Preclinical and Clinical Studies", Journal of Cardiovascular Translational Research, Apr. 23, 2019, pp. 1-8.
Kaufman, "Invasive Vascular Diagnosis", Radiology Key Fastest Radiology Insight Engine, Chapter 3, Dec. 23, 2015, 12 pages.
Keller, et al., "Dynamic Modulation of Device-Arterial Coupling to Determine Cardiac Output and Vascular Resistance", Annals of Biomedical Engineering, vol. 48, No. 9, Sep. 2020, pp. 2333-2342.
Schmitz-Rode, "Percutaneously implantable, self-expanding left heart support pump", Clinic for Radiological Diagnostics, 2001, 19 Pages.
Siess, et al., "Basic Design Criteria for Rotary Blood Pumps", Rotary Blood Pumps, 2000, pp. 69-83.
Corrected Notice of Allowance for U.S. Appl. No. 16/275,559 mailed Nov. 8, 2023.
Corrected Notice of Allowance for U.S. Appl. No. 17/070,323 mailed Oct. 4, 2023.
Corrected Notice of Allowance for U.S. Appl. No. 17/077,769 mailed Nov. 15, 2023.
Corrected Notice of Allowance for U.S. Appl. No. 17/077,769 mailed Nov. 6, 2023.
Corrected Notice of Allowance for U.S. Appl. No. 17/077,769 mailed Oct. 4, 2023.
Corrected Notice of Allowance for U.S. Appl. No. 17/180,041 mailed Oct. 4, 2023.
Examination Report for Australian Patent Application No. 2019206421 mailed Sep. 29, 2023.
Extended Search Report for European Application No. 23189145.8 mailed Nov. 27, 2023.
Extended Search Report for European Application No. 23189147.4 mailed Dec. 13, 2023.
Extended Search Report for European Application No. 23189148.2 mailed Dec. 13, 2023.
Extended Search Report for European Application No. 23189149.0 mailed Dec. 13, 2023.
Final Office Action for U.S. Appl. No. 17/078,472 mailed Oct. 23, 2023.
Final Office Action for U.S. Appl. No. 17/574,701 mailed Feb. 8, 2024.
Hearing Notice for Indian Patent Application No. 201917018651 mailed Dec. 11, 2023.
Issue Notification for U.S. Appl. No. 16/275,559 mailed Nov. 22, 2023.
Issue Notification for U.S. Appl. No. 17/070,323 mailed Oct. 18, 2023.
Issue Notification for U.S. Appl. No. 17/077,769 mailed Nov. 29, 2023.
Issue Notification for U.S. Appl. No. 17/180,041 mailed Oct. 18, 2023.
Non-Final Office Action for U.S. Appl. No. 16/952,327 mailed Oct. 13, 2023.
Non-Final Office Action for U.S. Appl. No. 17/070,670 mailed Oct. 30, 2023.
Non-Final Office Action for U.S. Appl. No. 17/176,344 mailed Oct. 31, 2023.
Non-Final Office Action for U.S. Appl. No. 17/528,807 mailed Jan. 12, 2024.
Notice of Allowance for U.S. Appl. No. 16/275,559 mailed Oct. 4, 2023.
Notice of Allowance for U.S. Appl. No. 16/952,389 mailed Feb. 7, 2024.
Notice of Allowance for U.S. Appl. No. 17/078,439 mailed Dec. 5, 2023.
Notice of Allowance for U.S. Appl. No. 17/173,944 mailed Nov. 8, 2023.
Notice of Allowance for U.S. Appl. No. 17/177,296 mailed Nov. 17, 2023.
Office Action for Canadian Application No. 3,176,272 mailed Jan. 2, 2024.
Office Action for Chinese Application No. 202080017728.9 mailed Nov. 6, 2023.
Office Action for Japanese Application No. 2021-533242 mailed Nov. 8, 2023.
U.S. Appl. No. 18/511,532, filed Nov. 16, 2023.
Corrected Notice of Allowance for U.S. Appl. No. 16/952,327 mailed Sep. 20, 2024.
Corrected Notice of Allowance for U.S. Appl. No. 17/528,015 mailed Apr. 11, 2025.
Corrected Notice of Allowance for U.S. Appl. No. 17/528,807 mailed Sep. 19, 2024.
Corrected Notice of Allowance for U.S. Appl. No. 17/857,402 mailed Nov. 7, 2024.
Extended Search Report for European Application No. 24200871.2 mailed Jan. 30, 2025.
Extended Search Report for European Application No. 24200875.3 mailed Jan. 13, 2025.
Extended Search Report for European Application No. 24206716.3 mailed Nov. 21, 2024.
Extended Search Report for European Application No. 24209593.3 mailed Dec. 4, 2024.
Extended Search Report for European Application No. 24209594.1 mailed Dec. 4, 2024.
Extended Search Report for European Application No. 24211523.6 mailed Feb. 7, 2025.
Extended Search Report for European Application No. 24211525.1 mailed Feb. 20, 2025.
Final Office Action for U.S. Appl. No. 17/078,472 mailed Mar. 12, 2025.
Final Office Action for U.S. Appl. No. 17/723,656 mailed Apr. 8, 2025.
Final Office Action for U.S. Appl. No. 18/511,532 mailed Apr. 11, 2025.
Issue Notification for U.S. Appl. No. 16/952,327 mailed Oct. 9, 2024.
Issue Notification for U.S. Appl. No. 17/070,670 mailed Jan. 8, 2025.
Issue Notification for U.S. Appl. No. 17/528,807 mailed Oct. 9, 2024.
Issue Notification for U.S. Appl. No. 17/857,402 mailed Dec. 18, 2024.
Non-Final Office Action for U.S. Appl. No. 17/176,344 mailed Feb. 20, 2025.
Non-Final Office Action for U.S. Appl. No. 17/528,015 mailed Oct. 21, 2024.
Non-Final Office Action for U.S. Appl. No. 17/609,589 mailed Jan. 30, 2025.
Non-Final Office Action for U.S. Appl. No. 17/677,571 mailed Feb. 20, 2025.
Non-Final Office Action for U.S. Appl. No. 17/678,122 mailed Dec. 5, 2024.
Non-Final Office Action for U.S. Appl. No. 17/678,812 mailed Sep. 26, 2024.
Non-Final Office Action for U.S. Appl. No. 17/682,104 mailed Sep. 30, 2024.
Non-Final Office Action for U.S. Appl. No. 17/722,752 mailed Mar. 17, 2025.

(56)            References Cited

OTHER PUBLICATIONS

Non-Final Office Action for U.S. Appl. No. 17/723,150 mailed Dec. 19, 2024.
Non-Final Office Action for U.S. Appl. No. 17/723,656 mailed Dec. 5, 2024.
Non-Final Office Action for U.S. Appl. No. 18/121,995 mailed Mar. 27, 2025.
Non-Final Office Action for U.S. Appl. No. 18/122,504 mailed Mar. 5, 2025.
Notice of Allowance for U.S. Appl. No. 17/070,670 mailed Sep. 11, 2024.
Notice of Allowance for U.S. Appl. No. 17/528,015 mailed Mar. 25, 2025.
Notice of Allowance for U.S. Appl. No. 17/528,807 mailed Sep. 9, 2024.
Notice of Allowance for U.S. Appl. No. 17/532,318 mailed Feb. 25, 2025.
Notice of Allowance for U.S. Appl. No. 17/723,150 mailed Apr. 7, 2025.
Notice of Allowance for U.S. Appl. No. 17/857,402 mailed Oct. 8, 2024.
Office Action for Japanese Application No. 2022-559757 mailed Dec. 23, 2024.
Office Action for Japanese Application No. 2023-191120 mailed Mar. 17, 2025.
Office Action for Japanese Application No. 2023-191120 mailed Oct. 1, 2024.
Restriction Requirement for U.S. Appl. No. 17/722,752 mailed Sep. 12, 2024.
Restriction Requirement for U.S. Appl. No. 17/723,150 mailed Sep. 11, 2024.
Restriction Requirement for U.S. Appl. No. 17/723,656 mailed Sep. 12, 2024.
Restriction Requirement for U.S. Appl. No. 18/001,680 mailed Mar. 28, 2025.
U.S. Appl. No. 18/882,984, filed Sep. 12, 2024.
U.S. Appl. No. 18/889,744, filed Sep. 19, 2024.
U.S. Appl. No. 18/933,729, filed Oct. 31, 2024.
U.S. Appl. No. 18/933,745, filed Oct. 31, 2024.
U.S. Appl. No. 18/933,749, filed Oct. 31, 2024.
U.S. Appl. No. 18/933,759, filed Oct. 31, 2024.
U.S. Appl. No. 18/947,762, filed Nov. 14, 2024.
U.S. Appl. No. 18/949,258, filed Nov. 15, 2024.
U.S. Appl. No. 18/955,121, filed Nov. 21, 2024.
U.S. Appl. No. 18/958,181, filed Nov. 25, 2024.
U.S. Appl. No. 18/958,189, filed Nov. 25, 2024.
U.S. Appl. No. 18/958,196, filed Nov. 25, 2024.
U.S. Appl. No. 18/958,200, filed Nov. 25, 2024.
U.S. Appl. No. 19/011,892, filed Jan. 7, 2025.
U.S. Appl. No. 19/013,727, filed Jan. 8, 2025.
U.S. Appl. No. 19/013,744, filed Jan. 8, 2025.
U.S. Appl. No. 19/014,336, filed Jan. 9, 2025.
U.S. Appl. No. 19/014,344, filed Jan. 9, 2025.
Corrected Notice of Allowance for U.S. Appl. No. 17/528,015 mailed May 13, 2025.
Corrected Notice of Allowance for U.S. Appl. No. 17/678,122 mailed May 27, 2025.
Corrected Notice of Allowance for U.S. Appl. No. 17/723,150 mailed Apr. 24, 2025.
Examination Report for Australian Application No. 2024203274 mailed May 1, 2025.
Extended Search Report for European Application No. 25151821.3 mailed Apr. 14, 2025.
Extended Search Report for European Application No. 25163036.4 mailed Jul. 25, 2025.
Extended Search Report for European Application No. 25163043.0 mailed Jul. 28, 2025.
Final Office Action for U.S. Appl. No. 17/678,812 mailed May 28, 2025.
International Search Report and Written Opinion for International Application No. PCT/IB2024/063113 mailed Jun. 11, 2025.
International Search Report and Written Opinion for International Application No. PCT/IB2024/063115 mailed Jun. 19, 2025.
International Search Report and Written Opinion for International Application No. PCT/IB2024/063109 mailed Jun. 2, 2025.
International Search Report and Written Opinion for International Application No. PCT/IB2024/063110 mailed Jun. 2, 2025.
Invitation to pay Additional Fees for International Application No. PCT/IB2024/063113 mailed Apr. 17, 2025.
Invitation to pay Additional Fees for International Application No. PCT/IB2024/063115 mailed Apr. 15, 2025.
Issue Notification for U.S. Appl. No. 17/528,015 mailed Jun. 18, 2025.
Issue Notification for U.S. Appl. No. 17/678,122 mailed Jun. 4, 2025.
Non-Final Office Action for U.S. Appl. No. 17/682,073 mailed May 28, 2024.
Non-Final Office Action for U.S. Appl. No. 17/682,104 mailed May 28, 2025.
Non-Final Office Action for U.S. Appl. No. 18/001,680 mailed Jun. 20, 2025.
Notice of Allowance for U.S. Appl. No. 17/678,122 mailed Apr. 30, 2025.
Office Action for Chinese Application No. 202180006817.8 mailed Jun. 13, 2025.
Office Action for Chinese Application No. 202210520564.2 mailed May 23, 2025.
Office Action for Chinese Application No. 202210540435.X mailed May 22, 2025.
Office Action for Chinese Application No. 202210580274.7 mailed May 22, 2025.
Office Action for Chinese Application No. 202210583463.X mailed Jun. 13, 2025.
Office Action for Chinese Application No. 202210587585.6 mailed Jun. 13, 2025.
Office Action for Chinese Application No. 202210587598.3 mailed Jun. 6, 2025.
Office Action for Chinese Application No. 202210791551.9 mailed May 16, 2025.
Office Action for Chinese Application No. 202210802982.0 mailed May 16, 2025.
Office Action for Chinese Application No. 202210847103.6 mailed May 16, 2025.
Office Action for Chinese Application No. 202310541980.5 mailed Jun. 16, 2025.
Office Action for Chinese Application No. 202310542349.7 mailed Jun. 4, 2025.
Office Action for Japanese Application No. 2024-066507 mailed Jun. 11, 2025.
Restriction Requirement for U.S. Appl. No. 18/122,486 mailed Apr. 14, 2025.
Corrected Notice of Allowance for U.S. Appl. No. 17/722,752 mailed Jul. 25, 2025.
Corrected Notice of Allowance for U.S. Appl. No. 17/857,402 mailed Oct. 30, 2024.
Corrected Notice of Allowance for U.S. Appl. No. 18/122,456 mailed Feb. 19, 2026.
Corrected Notice of Allowance for U.S. Appl. No. 18/122,486 mailed Dec. 17, 2025.
Corrected Notice of Allowance for U.S. Appl. No. 18/933,729 mailed Jul. 2, 2025.
Corrected Notice of Allowance for U.S. Appl. No. 18/933,729 mailed Jul. 23, 2025.
Examination Report for Australian Application No. 2021253815 mailed Dec. 19, 2025.
Examination Report for Australian Application No. 2025200291 mailed Sep. 16, 2025.
Examination Report for Indian Application No. 202247058135 mailed Jan. 27, 2026.
Extended Search Report for European Application No. 25204084.5 mailed Feb. 2, 2026.

(56)     References Cited

OTHER PUBLICATIONS

Final Office Action for U.S. Appl. No. 17/176,344 mailed Oct. 7, 2025.
Final Office Action for U.S. Appl. No. 18/001,680 mailed Dec. 23, 2025.
Final Office Action for U.S. Appl. No. 18/121,995 mailed Dec. 19, 2025.
Final Office Action for U.S. Appl. No. 18/122,504 mailed Oct. 23, 2025.
International Search Report and Written Opinion from International Application No. PCT/IB2025/056384 mailed Dec. 16, 2025.
International Search Report and Written Opinion from International Application No. PCT/IB2025/056385 mailed Jan. 16, 2026.
Invitation to pay Additional Fees for International Application No. PCT/IB2025/056384 mailed Oct. 9, 2025.
Invitation to pay Additional Fees for International Application No. PCT/IB2025/056385 mailed Oct. 1, 2025.
Issue Notification for U.S. Appl. No. 17/532,318 mailed Oct. 1, 2025.
Issue Notification for U.S. Appl. No. 17/722,752 mailed Oct. 15, 2025.
Issue Notification for U.S. Appl. No. 17/723,150 mailed Oct. 1, 2025.
Issue Notification for U.S. Appl. No. 18/122,486 mailed Jan. 28, 2026.
Issue Notification for U.S. Appl. No. 18/933,729 mailed Jan. 28, 2026.
Non-Final Office Action for U.S. Appl. No. 17/078,472 mailed Nov. 19, 2024.
Non-Final Office Action for U.S. Appl. No. 17/609,589 mailed Sep. 5, 2025.
Non-Final Office Action for U.S. Appl. No. 17/677,571 mailed Aug. 20, 2025.
Non-Final Office Action for U.S. Appl. No. 17/678,812 mailed Dec. 3, 2025.
Non-Final Office Action for U.S. Appl. No. 17/682,104 mailed Jan. 16, 2026.
Non-Final Office Action for U.S. Appl. No. 17/723,656 mailed Nov. 3, 2025.
Non-Final Office Action for U.S. Appl. No. 18/444,972 mailed Dec. 9, 2025.
Non-Final Office Action for U.S. Appl. No. 18/447,025 mailed Nov. 5, 2025.
Non-Final Office Action for U.S. Appl. No. 18/511,532 mailed Aug. 27, 2024.
Non-Final Office Action for U.S. Appl. No. 18/632,533 mailed Jan. 30, 2026.
Non-Final Office Action for U.S. Appl. No. 18/632,545 mailed Jan. 13, 2026.
Non-Final Office Action for U.S. Appl. No. 18/637,667 mailed Feb. 17, 2026.
Non-Final Office Action for U.S. Appl. No. 18/640,260 mailed Feb. 17, 2026.
Non-Final Office Action for U.S. Appl. No. 18/640,285 mailed Jan. 26, 2026.
Non-Final Office Action for U.S. Appl. No. 18/652,930 mailed Dec. 31, 2025.
Non-Final Office Action for U.S. Appl. No. 18/652,959 mailed Oct. 1, 2025.
Notice of Allowance for U.S. Appl. No. 17/078,472 mailed Dec. 17, 2025.
Notice of Allowance for U.S. Appl. No. 17/609,589 mailed Feb. 4, 2026.
Notice of Allowance for U.S. Appl. No. 17/722,752 mailed Jul. 7, 2025.
Notice of Allowance for U.S. Appl. No. 18/122,456 mailed Aug. 14, 2025.
Notice of Allowance for U.S. Appl. No. 18/122,456 mailed Jan. 12, 2026.
Notice of Allowance for U.S. Appl. No. 18/122,486 mailed Dec. 9, 2025.
Notice of Allowance for U.S. Appl. No. 18/933,729 mailed Jul. 1, 2025.
Notice of Allowance for U.S. Appl. No. 18/933,729 mailed Nov. 18, 2025.
Office Action for Chinese Application No. 202210583463.X mailed Nov. 17, 2025.
Office Action for Chinese Application No. 202210802982.0 mailed Oct. 24, 2025.
Office Action for Chinese Application No. 202280006309.4 mailed Dec. 4, 2025.
Office Action for Chinese Application No. 202280015894.4 mailed Aug. 1, 2025.
Office Action for Chinese Application No. 202310542349.7 mailed Nov. 28, 2025.
Office Action for Japanese Application No. 2023-547155 mailed Jan. 30, 2026.
Restriction Requirement for U.S. Appl. No. 18/635,286 mailed Jan. 28, 2026.
Restriction Requirement for U.S. Appl. No. 18/635,292 mailed Jan. 15, 2026.
U.S. Appl. No. 19/459,719, filed Jan. 26, 2026.
U.S. Appl. No. 19/460,541, filed Jan. 27, 2026.
U.S. Appl. No. 19/463,581, filed Jan. 29, 2026.
U.S. Appl. No. 19/466,779, filed Feb. 2, 2026.
U.S. Appl. No. 63/566,681, filed Mar. 18, 2024.
U.S. Appl. No. 63/615,377, filed Dec. 28, 2023.
U.S. Appl. No. 63/692,734, filed Sep. 10, 2024.
Corrected Notice of Allowance for U.S. Appl. No. 17/609,589 mailed Feb. 24, 2026.
Non-Final Office Action for U.S. Appl. No. 17/078,472 mailed Aug. 12, 2025.
Non-Final Office Action for U.S. Appl. No. 18/511,532 mailed Aug. 18, 2025.
Non-Final Office Action for U.S. Appl. No. 18/632,557 mailed Feb. 24, 2026.

* cited by examiner

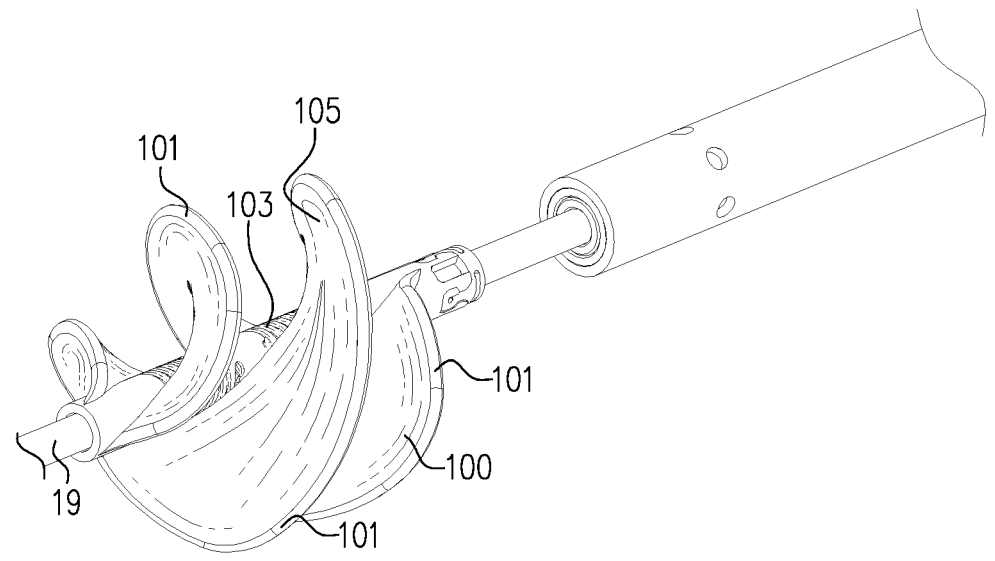
FIG. 20Ai
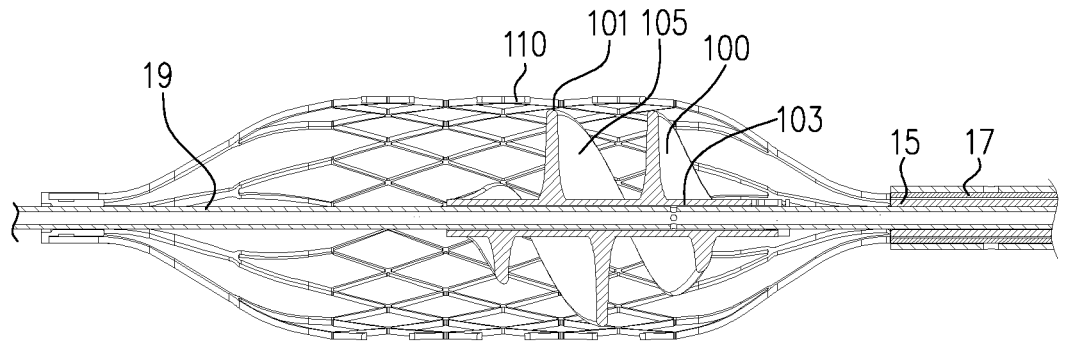
FIG. 20Aii

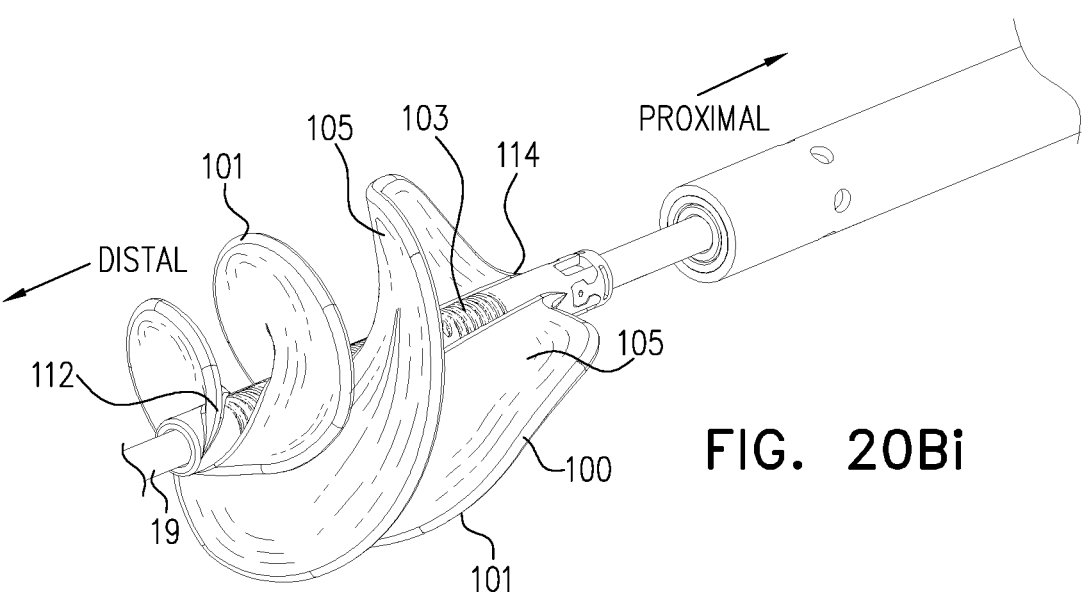
FIG. 20Bi
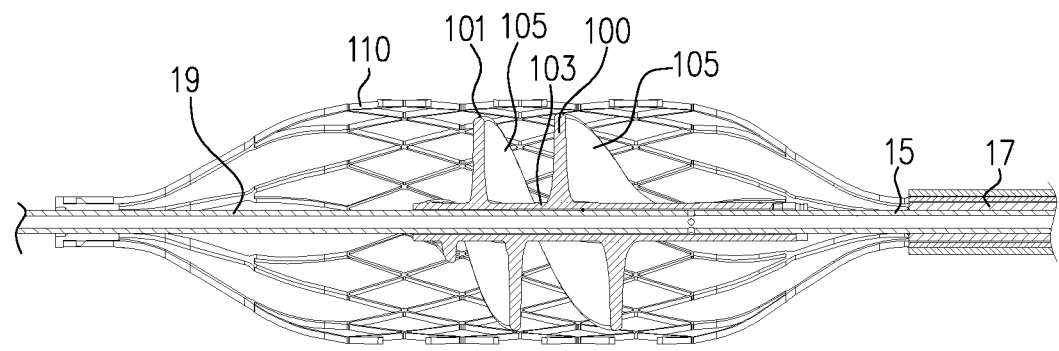
FIG. 20Bii

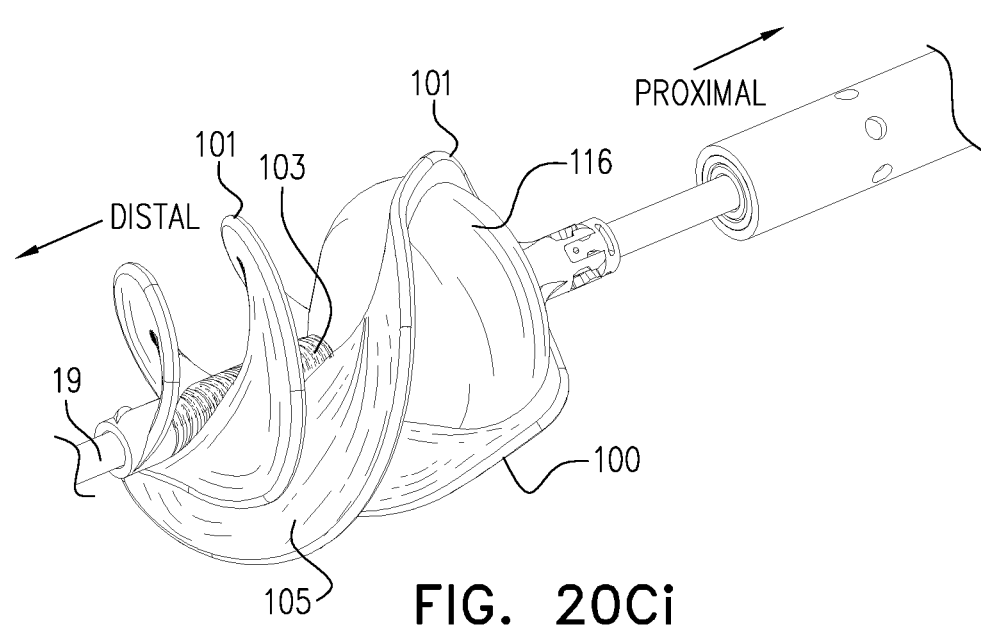
FIG. 20Ci
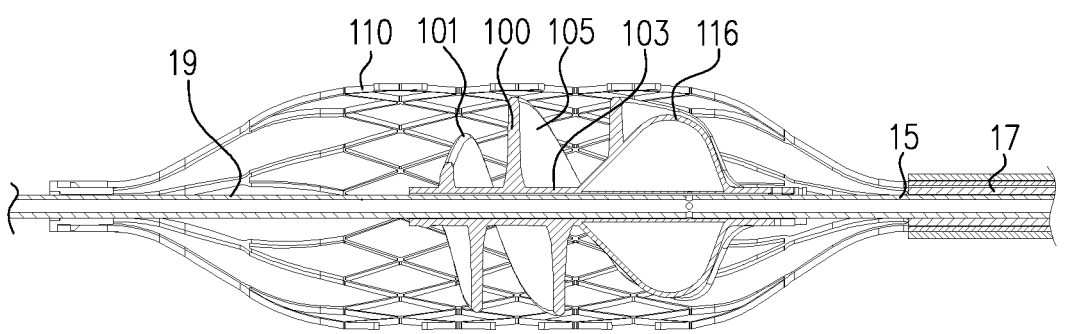
FIG. 20Cii

CENTRIFUGAL AND MIXED-FLOW IMPELLERS FOR USE WITH A BLOOD PUMP

CROSS-REFERENCES TO RELATED APPLICATIONS

The present application is a US national phase application PCT Application No. PCT/IB2021/052590 to Zipory (published as WO 21/198881), filed Mar. 29, 2021, which claims priority from U.S. Provisional Patent Application 63/003,955 to Zipory, entitled "Ventricular assist device," filed Apr. 2, 2020, which is incorporated herein by reference.

FIELD OF EMBODIMENTS OF THE INVENTION

Some applications of the present invention generally relate to medical apparatus. Specifically, some applications of the present invention relate to a ventricular assist device and methods of use thereof.

BACKGROUND

Ventricular assist devices are mechanical circulatory support devices designed to assist and unload cardiac chambers in order to maintain or augment cardiac output. They are used in patients suffering from a failing heart and in patients at risk for deterioration of cardiac function during percutaneous coronary interventions. Most commonly, a left-ventricular assist device is applied to a defective heart in order to assist left-ventricular functioning. In some cases, a right-ventricular assist device is used in order to assist right-ventricular functioning. Such assist devices are either designed to be permanently implanted or mounted on a catheter for temporary placement.

SUMMARY OF EMBODIMENTS

In accordance with some applications of the present invention, a distal end of a ventricular assist device is placed inside a subject's left ventricle, such that one or more centrifugally-pumping impellers of the ventricular assist device are disposed within the subject's left ventricle. For some applications, a plurality of centrifugally-pumping impellers are placed within the left ventricle. Each of the centrifugally-pumping impellers is typically disposed inside a respective impeller housing. Typically, the impeller housing defines at least one blood inlet opening (via which blood flows into the impeller housing), and a blood-outlet portion. Typically, at least one volute is disposed at least partially around the blood-outlet portion. Typically, the volute spirals and curves through 90 degrees and then leads into a pump-outlet tube, which is disposed such that blood-outlet openings defined by a proximal portion of the pump-outlet tube, are disposed in the subject's aorta. Typically, the centrifugally-pumping impellers are configured to assist the functioning of the left ventricle, by pumping blood from the left ventricle, through the volutes, into the pump-outlet tube, and then out of the blood-outlet openings and into the aorta.

For some applications, each of the impeller housings includes a plurality of blood inlet openings, e.g., an upper blood-inlet opening and a lower blood-inlet opening. Similarly, for some applications, each of the impeller housings includes a plurality of volutes, as described in further detail hereinbelow.

For some applications, the ventricular assist device includes two or more centrifugally-pumping impellers, that are disposed in series with one another along the axis of the device. For some such applications, each of the two or more centrifugally-pumping impellers is disposed on a single rigid axial shaft. Pumping blood using a plurality of centrifugally-pumping impellers typically increases the volume of blood that is pumped by the ventricular assist device relative to if only one centrifugally-pumping impeller is used, ceteris paribus. It is noted that although some applications of the present invention are described with reference to a ventricular assist device that includes two or more centrifugally-pumping impellers, the scope of the present application includes practicing some of the applications described herein with a ventricular assist device that includes a single centrifugally-pumping impeller.

For some applications, a left-ventricular assist device includes a pump-outlet tube configured such that a proximal portion of the pump-outlet tube traverses the subject's aortic valve, and a distal portion of the pump-outlet tube is disposed within the subject's left ventricle. The pump-outlet tube typically at least one blood inlet opening that is configured to be disposed within the left ventricle and at least one blood outlet opening that is configured to be disposed within the subject's aorta. For some applications, a mixed-flow impeller is configured to pump blood through the pump-outlet tube from the subject's left ventricle to the subject's aorta. For some such applications, the mixed-flow impeller includes an expandable portion disposed along an axis of the impeller and shaped such that, in its expanded configuration, a diameter of the expandable portion increases from a distal end of the expandable portion to a proximal end of the expandable portion. The mixed-flow impeller is thereby configured to impart radial flow components to blood as the blood flows from the distal end to the proximal end of the mixed-flow impeller.

For some applications, the expandable portion of the impeller is inflatable. Typically, the left-ventricular assist device includes a purging system that is configured to purge portions of the left-ventricular assist device by pumping purging fluid through the left-ventricular assist device. For some applications, the expandable portion of the impeller is configured to be inflated with the purging fluid. For some such applications, the purging system is configured to control the inflation of the expandable portion of the impeller, by modulating the pressure at which the purging fluid is pumped into the ventricular assist device.

For some applications, the impeller includes one or more impeller blades which are shaped to transition from being spiral shaped within a distal portion of the impeller to being substantially radially-extending within a proximal portion of the impeller. Typically, the distal portion of the impeller is configured primarily to impart axial flow to blood that it pumps, and the proximal portion of the impeller is configured to impart substantial radial flow to blood that it pumps.

For some applications, the pump-outlet tube defines a widened region in the vicinity of the impeller, which is wider than a portion of the pump-outlet tube proximal thereto. Typically, the pump-outlet tube is configured to redirect the radial blood flow components axially, by the pump-outlet tube narrowing within the portion of the pump-outlet tube that is proximal to the widened portion. For some applications, one or more spiral flow rectifiers are disposed within the pump-outlet tube, proximally with respect to impeller. Typically, the spiral flow rectifiers are configured to reduce radial flow components from blood flow by converting radial flow components to axial flow prior to the blood flowing out of the at least one blood outlet opening. For some applications, the one or more spiral flow rectifiers have spiral shapes with a pitch of the spiral shapes increasing from the distal ends of the flow rectifiers to their proximal ends, such that the spiral flow rectifiers are configured to gradually covert radial flow to axial flow.

For some applications, an expandable flow rectifier is configured to reduce radial flow components from blood flow through the pump-outlet tube prior to the blood flowing from the at least one blood outlet opening. Typically, the expandable flow rectifier is disposed along an axis of the pump-outlet tube and, in its expanded configuration, is shaped such that its diameter decreases from a distal end of the expandable flow rectifier to a proximal end of the expandable flow rectifier. Typically, the expandable flow rectifier is inflatable. For some such applications, the left-ventricular assist device includes a purging system configured to purge portions of the left-ventricular assist device by pumping purging fluid through the left-ventricular assist device. For some applications, the expandable flow rectifier is configured to be inflated with the purging fluid. For some such applications, the purging system is configured to control the inflation of the expandable flow rectifier, by modulating the pressure at which the purging fluid is pumped into the ventricular assist device.

There is therefore provided, in accordance with some applications of the present invention, apparatus including:

a left-ventricular assist device configured to assist left-ventricular functioning of a subject, the left-ventricular assist device including:

a pump-outlet tube configured such that a proximal portion of the pump-outlet tube traverses an aortic valve of the subject, and a distal portion of the pump-outlet tube is disposed within a left ventricle of the subject, the pump-outlet tube defining at least one blood inlet opening that is configured to be disposed within the left ventricle and at least one blood outlet opening that is configured to be disposed within an aorta of the subject;

a mixed-flow impeller configured to pump blood through the pump-outlet tube from the subject's left ventricle to the subject's aorta, the mixed-flow impeller including an expandable portion disposed along an axis of the impeller and being shaped such that, in its expanded configuration, a diameter of the expandable portion increases from a distal end of the expandable portion to a proximal end of the expandable portion, the mixed-flow impeller thereby being configured to impart radial flow components to blood as the blood flows from the distal end to the proximal end of the mixed-flow impeller.

In some applications, the pump-outlet tube defines a widened region in the vicinity of the impeller, which is wider than a portion of the pump-outlet tube proximal thereto, and pump-outlet tube is configured to redirect the radial blood flow components axially, by the pump-outlet tube narrowing within the portion of the pump-outlet tube that is proximal to the widened portion.

In some applications, in its expanded configuration, the expandable portion of the impeller has a three-dimensional teardrop shape. In some applications, in its expanded configuration, the expandable portion of the impeller has a conical shape. In some applications, in its expanded configuration, the expandable portion of the impeller has a frustoconical shape.

In some applications, the expandable portion of the impeller includes a shape memory alloy that is shape set such that the expandable portion of the impeller is self-expandable.

In some applications, the apparatus further includes an expandable flow rectifier that is configured to reduce radial flow components from blood flow through the pump-outlet tube prior to the blood flowing from the at least one blood outlet opening, the expandable flow rectifier being disposed along an axis of the pump-outlet tube and, in its expanded configuration, being shaped such that its diameter decreases from a distal end of the expandable flow rectifier to a proximal end of the expandable flow rectifier.

In some applications, the expandable portion of the impeller is inflatable. In some applications, the left-ventricular assist device is configured for use with a purging fluid, the left-ventricular assist device includes a purging system configured to purge portions of the left-ventricular assist device by pumping the purging fluid through the left-ventricular assist device, and the expandable portion of the impeller is configured to be inflated with the purging fluid. In some applications, the purging system is configured to control the inflation of the expandable portion of the impeller, by modulating the pressure at which the purging fluid is pumped into the ventricular assist device.

In some applications, the impeller includes one or more impeller blades which are shaped to transition from being spiral shaped within a distal portion of the impeller to being substantially radially-extending within a proximal portion of the impeller. In some applications, the distal portion of the impeller is configured primarily to impart axial flow to blood that it pumps, and the proximal portion of the impeller is configured to impart substantial radial flow to blood that it pumps.

In some applications, the apparatus further includes one or more spiral flow rectifiers disposed within the pump-outlet tube, proximally with respect to impeller, the spiral flow rectifiers being configured to reduce radial flow components from blood flow by converting radial flow components to axial flow prior to the blood flowing out of the at least one blood outlet opening. In some applications, the one or more spiral flow rectifiers have spiral shapes with a pitch of the spiral shapes increasing from the distal ends of the flow rectifiers to their proximal ends, such that the spiral flow rectifiers are configured to gradually covert radial flow to axial flow.

There is further provided, in accordance with some applications of the present invention, apparatus including:

a left-ventricular assist device configured to assist left-ventricular functioning of a subject, the left-ventricular assist device including:

a pump-outlet tube configured such that a proximal portion of the tube traverses an aortic valve of the subject, and a distal portion of the pump-outlet tube is disposed within a left ventricle of the subject, the pump-outlet tube defining at least one blood inlet opening that is configured to be disposed within the left ventricle and at least one blood outlet opening that is configured to be disposed within an aorta of the subject;

an impeller configured to pump blood through the pump-outlet tube from the subject's left ventricle to the subject's aorta;

an expandable flow rectifier that is configured to reduce radial flow components from blood flow through the pump-outlet tube prior to the blood flowing from the at least one blood outlet opening, the expandable flow rectifier being disposed along an axis of the pump-outlet tube and, in its expanded configuration, being shaped such that its diameter decreases from a distal end to a proximal end of the expandable flow rectifier.

In some applications, the pump-outlet tube defines a widened region in the vicinity of the impeller, which is wider than a portion of the pump-outlet tube proximal thereto, the impeller is configured to impart centrifugal flow to blood such as to cause the blood to flow into the widened region of the pump-outlet tube, and pump-outlet tube is configured to redirect the blood axially by the pump-outlet tube narrowing within the portion of the pump-outlet tube that is proximal to the widened portion.

In some applications, in its expanded configuration, the expandable flow rectifier has a three-dimensional teardrop shape. In some applications, in its expanded configuration, the expandable flow rectifier has a conical shape. In some applications, in its expanded configuration, the expandable flow rectifier has a frustoconical shape.

In some applications, the expandable flow rectifier includes a shape memory alloy that is shape set such that the expandable flow rectifier is self-expandable.

In some applications, the expandable flow rectifier is inflatable. In some applications, the left-ventricular assist device is configured for use with a purging fluid, the left-ventricular assist device includes a purging system configured to purge portions of the left-ventricular assist device by pumping the purging fluid through the left-ventricular assist device, and the expandable flow rectifier is configured to be inflated with the purging fluid. In some applications, the purging system is configured to control the inflation of the expandable flow rectifier, by modulating the pressure at which the purging fluid is pumped into the ventricular assist device.

In some applications, the apparatus further includes one or more spiral flow rectifiers disposed within the pump-outlet tube proximally with respect to impeller, the spiral flow rectifiers being configured to reduce radial flow components from blood flow by converting radial flow components to axial flow prior to the blood flowing out of the at least one blood outlet opening. In some applications, the one or more spiral flow rectifiers have spiral shapes with a pitch of the spiral shapes increasing from the distal ends of the flow rectifiers to their proximal ends, such that the spiral flow rectifiers are configured to gradually covert radial flow to axial flow.

There is further provided, in accordance with some applications of the present invention, apparatus including:

a left-ventricular assist device configured to assist left-ventricular functioning of a subject, the left-ventricular assist device including:

a pump-outlet tube configured such that a proximal portion of the pump-outlet tube traverses an aortic valve of the subject, and a distal portion of the pump-outlet tube is disposed within a left ventricle of the subject;

a plurality of centrifugally-pumping impellers, disposed in series with each other, each of the centrifugally-pumping impellers being disposed within a respective impeller housing, and at least one volute being disposed around each of the impeller housings, each of the volutes leading to the pump-outlet tube, each of the impellers being configured to pump blood from the left ventricle to an aorta of the subject by pumping blood into the impeller housing within which the impeller is disposed, into the at least one volute that is disposed around the impeller housing, and into the pump-outlet tube.

There is further provided, in accordance with some applications of the present invention, apparatus including:

a left-ventricular assist device configured to assist left-ventricular functioning of a subject, the left-ventricular assist device including:

a pump-outlet tube configured such that a proximal portion of the pump-outlet tube traverses an aortic valve of the subject, and a distal portion of the pump-outlet tube is disposed within a left ventricle of the subject;

at least one centrifugally-pumping impeller disposed within an impeller housing, the impeller housing defining an upper blood-inlet opening and a lower blood inlet opening;

at least one volute disposed around the impeller housing, the volute leading to the pump-outlet tube, the impeller being configured to pump blood from the left ventricle to an aorta of the subject by pumping blood into the impeller housing via both the upper blood-inlet opening and the lower blood-inlet opening, into the at least one volute that is disposed around the housing, and into the pump-outlet tube.

There is further provided, in accordance with some applications of the present invention, apparatus including:

a left-ventricular assist device configured to assist left-ventricular functioning of a subject, the left-ventricular assist device including:

a pump-outlet tube configured such that a proximal portion of the pump-outlet tube traverses an aortic valve of the subject, and a distal portion of the pump-outlet tube is disposed within a left ventricle of the subject;

at least one centrifugally-pumping impeller disposed within an impeller housing, the impeller housing defining at least one blood-inlet opening;

at least one volute disposed around the impeller housing, the volute leading to the pump-outlet tube;

at least one blood-inflow tube that passes through at least one of the volute and pump-outlet tube, the blood-inflow tube defining a blood-inlet-tube opening, which is an opening through at least one of the volute and pump-outlet tube that is fluid communication with the ventricular blood stream;

the impeller being configured to pump blood from the left ventricle to an aorta of the subject by pumping blood into the impeller housing via the blood-inflow tube, into the blood-inlet opening, into the at least one volute that is disposed around the housing, and into the pump-outlet tube.

There is further provided, in accordance with some applications of the present invention, a method including:

manufacturing a multi-layered biconical centrifugal impeller, by:

cutting a tube of a shape-memory alloy, such that the tube defines a plurality of elongate struts;

curving respective sets of the elongate struts such that the respective sets of elongate struts defines respective layers of the multi-layered biconical centrifugal impeller; and covering the respective sets of elongate struts with respective layers of a covering material.

The present invention will be more fully understood from the following detailed description of embodiments thereof, taken together with the drawings, in which:

BRIEF DESCRIPTION OF THE DRAWINGS

FIGS. 20Ai and 20Aii are schematic illustrations of respective views of an impeller, in accordance with some applications of the present invention;

FIGS. 20Bi and 20Bii are schematic illustrations of respective views of an impeller, in accordance with some alternative applications of the present invention;

FIGS. 20Ci and 20Cii are schematic illustrations of respective views of an impeller, in accordance with some further alternative applications of the present invention;

DETAILED DESCRIPTION OF EMBODIMENTS

Figure 1A:
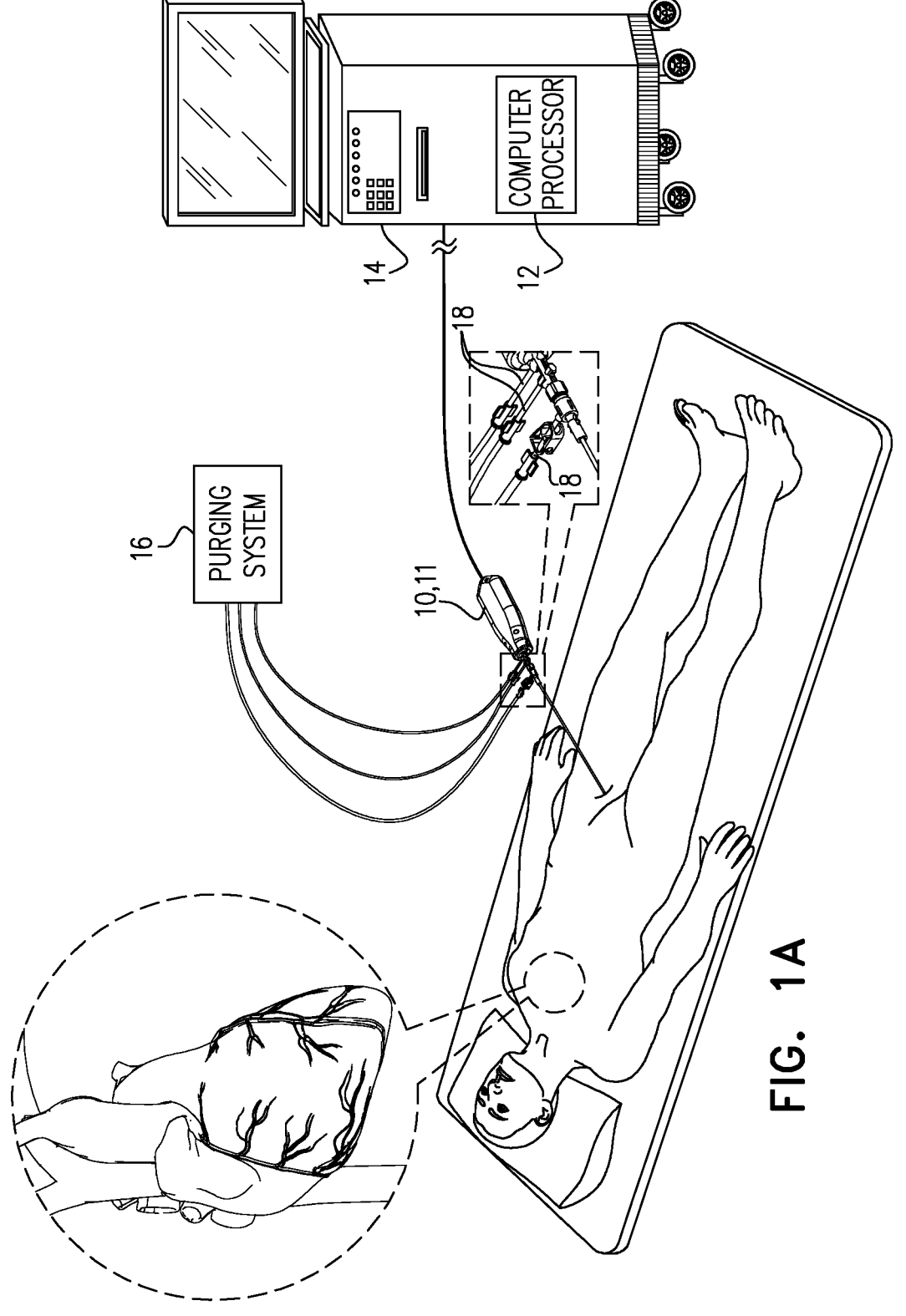
FIGS. 1A and 1B are schematic illustrations of a ventricular assist device that includes one or more centrifugally-pumping impellers, in accordance with some applications of the present invention.
Figure 1B:
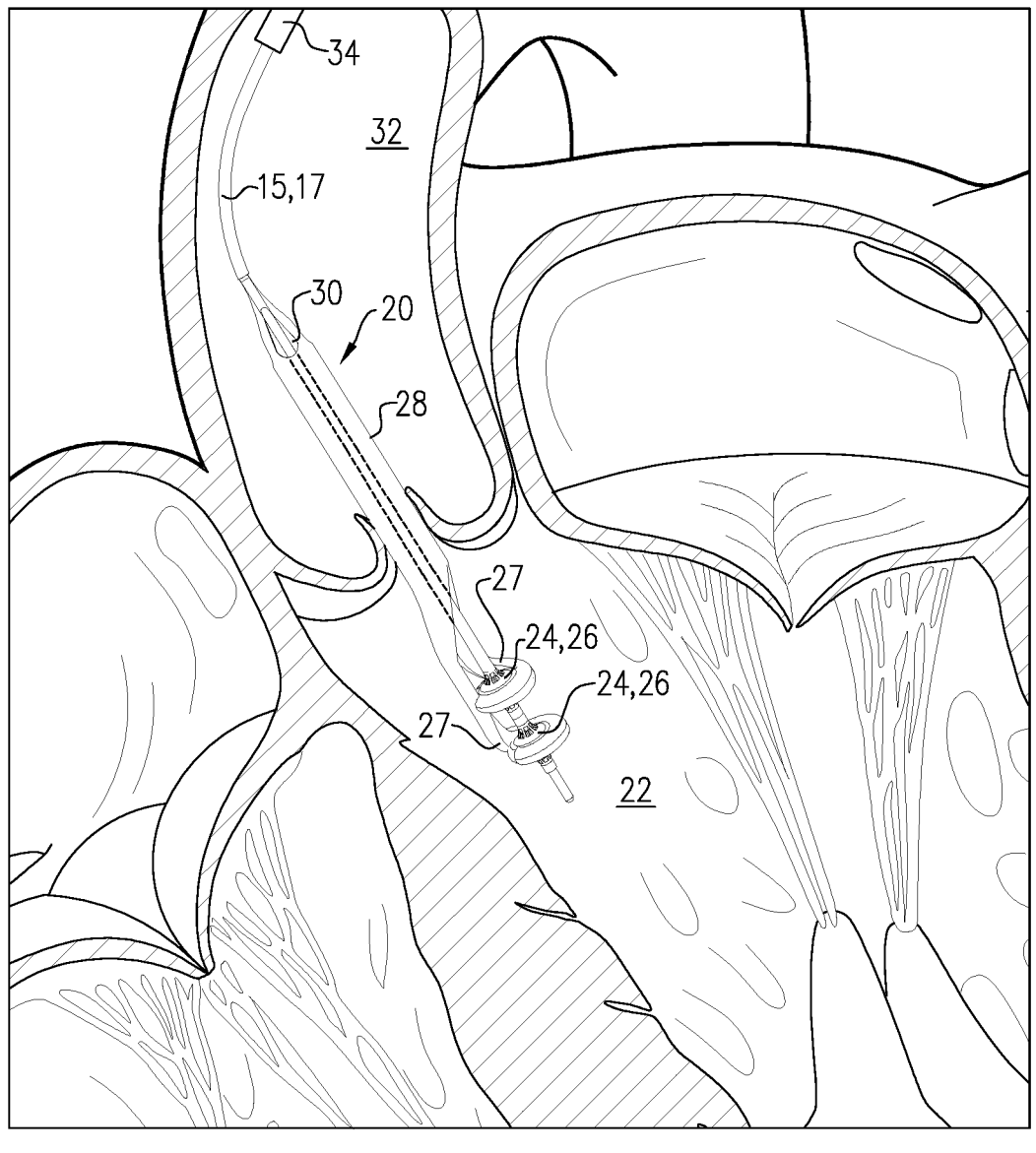

Reference is now made to FIGS. 1A-B, which are schematic illustrations of a ventricular assist device 20, a distal end of which is configured to be disposed in a subject's left ventricle 22, in accordance with some applications of the present invention. The ventricular assist device includes one or more centrifugally-pumping impellers 24 that are configured to be disposed within the subject's left ventricle 22. For some applications, the ventricular assist device includes a plurality of centrifugally-pumping impellers 24 that are configured to be disposed within left ventricle 22. Each of the centrifugally-pumping impellers 24 is typically disposed inside a respective impeller housing 26. Typically, the impeller housing defines at least one blood inlet opening 42, 44 (via which blood flows into the impeller housing, shown in FIG. 3), and a blood-outlet portion 46 (shown in FIG. 3). Typically at least one volute 27 is disposed at least partially around the blood-outlet portion. Typically, the volute spirals and curves through 90 degrees and then leads into a pump-outlet tube 28, which is disposed such that blood-outlet openings 30, defined by a proximal portion of the pump-outlet tube, are disposed in the subject's aorta 32. By being shaped in this way, the volute gradually converts radial flow to axial flow. Typically, the centrifugally-pumping impellers are configured to assist the functioning of the left ventricle, by pumping blood from the left ventricle, through volutes 27, into pump-outlet tube 28, and then out of blood-outlet openings 30 and into aorta 32.

For some applications, each of the impeller housings includes a plurality of blood-inlet openings, e.g., an upper blood-inlet opening 42 and a lower blood-inlet opening 44, as described in further detail hereinbelow. Similarly, for some applications, each of the impeller housings includes a plurality of volutes 27, as described in further detail hereinbelow.

With reference to FIG. 1A, for some applications, a motor 10 is disposed inside a motor unit 11 that is disposed outside the subject's body. Typically, a computer processor 12, which is part of a control console 14, drives the motor to rotate. The motor typically conveys rotational motion to the impeller via a drive cable 15, which is typically disposed within an outer tube 17 (with the outer tube acting as a bearing within which the drive cable rotates). For some applications, the drive cable is directly coupled to the centrifugally-pumping impeller. Alternatively, the drive cable is coupled to a rigid axial shaft 19 (shown in FIG. 4, for example), and the centrifugally pumping impeller is disposed on the rigid axial shaft. For some applications, the apparatus includes a purging system 16 and a plurality of purging fluid ports 18 (e.g., purging fluid inlet ports, and/or purging fluid outlet ports), via which a purging fluid (e.g., a glucose-based solution and/or saline) is pumped into the ventricular assist device, in order to purge portions of the ventricular assist device. Typically, the purging fluid is configured to be pumped into the apparatus such that the purging fluid flows between drive cable 15 and outer tube 17 and thereby purges the interface between the drive cable and the outer tube. Further typically, the purging fluid is configured to purge interfaces between axial shaft 19 and radial bearings within which the axial shaft rotates. For some applications, ventricular assist device 20 includes two or more centrifugally-pumping impellers 24, that are disposed in series with one another along the axis of the device, as shown in FIG. 1B. (It is noted that, in FIG. 1B, the ventricular-assist device is not shown to scale relative to the subject's anatomy. Similarly, the disposition of portions of the ventricular assist device relative to portions of the left ventricular anatomy is typically different from that shown in FIG. 1B.) For some such applications, each of the two or more centrifugally pumping impellers is disposed on a single rigid axial shaft 19. Pumping blood using a plurality of centrifugally-pumping impellers typically increases the volume of blood that is pumped by the ventricular assist device relative to if only one centrifugally-pumping impeller is used, ceteris paribus. It is noted that although some applications of the present invention are described with reference to a ventricular assist device that includes two or more centrifugally-pumping impellers, the scope of the present application includes practicing some of the applications described herein with a ventricular assist device that includes a single centrifugally-pumping impeller.

For some applications, the ventricular assist device is used to assist the functioning of a subject's left ventricle during a percutaneous coronary intervention. In such cases, the ventricular assist device is typically used for a period of up to 10 hours (e.g., up to six hours), during a period in which there is risk of developing hemodynamic instability (e.g., during or immediately following the percutaneous coronary intervention). Alternatively or additionally, the ventricular assist device is used to assist the functioning of a subject's left ventricle for a longer period (e.g., for example, 2-20 days, e.g., 4-14 days) upon a patient suffering from cardiogenic shock, which may include any low-cardiac-output state (e.g., acute myocardial infarction, myocarditis, cardiomyopathy, post-partum, etc.). For some applications, the ventricular assist device is used to assist the functioning of a subject's left ventricle for yet a longer period (e.g., several weeks or months), e.g., in a "bridge to recovery" treatment. For some such applications, the ventricular assist device is permanently or semi-permanently implanted, and the impellers of the ventricular assist device are powered transcutaneously, e.g., using an external antenna that is magnetically coupled to the impeller.

Typically the distal end of the ventricular assist device is guided to the left ventricle over a guidewire (not shown). During the insertion of the distal end of the device to the left ventricle, a delivery catheter 34 (shown in FIG. 1B) is disposed over the distal end of the device. Once the distal end of the device is disposed in the left ventricle, the delivery catheter is typically retracted to the aorta, and the guidewire is withdrawn from the subject's body. Typically, centrifugally-pumping impellers 24 and impeller housings 26 are radially expandable (e.g., radially self-expandable), as described in further detail hereinbelow. During the insertion of the distal end of the device to the left ventricle, delivery catheter 34 typically maintains the centrifugally-pumping impellers 24 and impeller housings 26 in radially-constrained (also known as, crimped) configurations. The retraction of the delivery catheter typically causes the centrifugally-pumping impellers 24 and impeller housings 26 to assume non-radially-constrained configurations, due to the centrifugally-pumping impellers 24 and impeller housings 26 radially self-expanding. Alternatively or additionally, upon having been delivered to the left ventricle, the centrifugally-pumping impellers 24 and impeller housings 26 are manually radially expanded. Typically, the ventricular assist device is inserted into the subject's body in order to provide an acute treatment to the subject. For some applications, in order to withdraw the left ventricular device from the subject's body at the end of the treatment, the delivery catheter is advanced over the distal end of the device, which causes the centrifugally-pumping impellers 24 and impeller housings 26 to assume radially-constrained configurations. Alternatively or additionally, the distal end of the device is retracted into the delivery catheter which causes centrifugally-pumping impellers 24 and impeller housings 26 to assume radially-constrained configurations.

For some applications (not shown), the ventricular assist device and/or delivery catheter 34 includes an ultrasound transducer at its distal end and the ventricular assist device is advanced toward the subject's ventricle under ultrasound guidance.

Typically, the pump-outlet tube and the one or more volutes are continuous with respect to each other. That is to say that, typically, the pump-outlet tube and the one or more volutes are made of the same material as each other, and the volutes merge with the blood-outlet tube to form a continuous blood flow channel. Pump-outlet tube 28 and/or volute 27 are typically made of a blood-impermeable collapsible material. For example, pump-outlet tube 28 and/or volute 27 may include polyurethane, polyester, and/or silicone. Alternatively or additionally, pump-outlet tube 28 and/or volute 27 are made of polyethylene terephthalate (PET) and/or polyether block amide (e.g., PEBAX®). For some applications (not shown), pump-outlet tube 28 and/or volute 27 are reinforced with a reinforcement structure, e.g., a braided reinforcement structure, such as a braided nitinol tube.

Typically, the proximal portion of pump-outlet tube 28 is configured to be placed such that it is at least partially disposed within the subject's ascending aorta. For some applications, the proximal portion of pump-outlet tube 28 traverses the subject's aortic valve, passing from the subject's left ventricle into the subject's ascending aorta, as shown in FIG. 1B. As described hereinabove, for some applications, the proximal portion of pump-outlet tube 28 defines one or more blood-outlet openings 30, via which blood flows from the tube into the ascending aorta, during operation of the impeller. Typically, pump-outlet tube 28 defines a plurality of blood-outlet openings 30, for example, between two and eight blood-outlet openings (e.g., between two and four blood-outlet openings). During operation of the impeller, the pressure of the blood flow through pump-outlet tube 28 typically maintains the proximal portion of pump-outlet tube 28 in an open state. For some applications, in the event that, for example, the impellers malfunction, the proximal portion of pump-outlet tube 28 is configured to collapse inwardly, in response to pressure outside of the proximal portion of the pump-outlet tube exceeding pressure inside the proximal portion of the tube. In this manner, the proximal portion of the pump-outlet tube acts as a safety valve, preventing retrograde blood flow into the left ventricle from the aorta.

Figure 2:
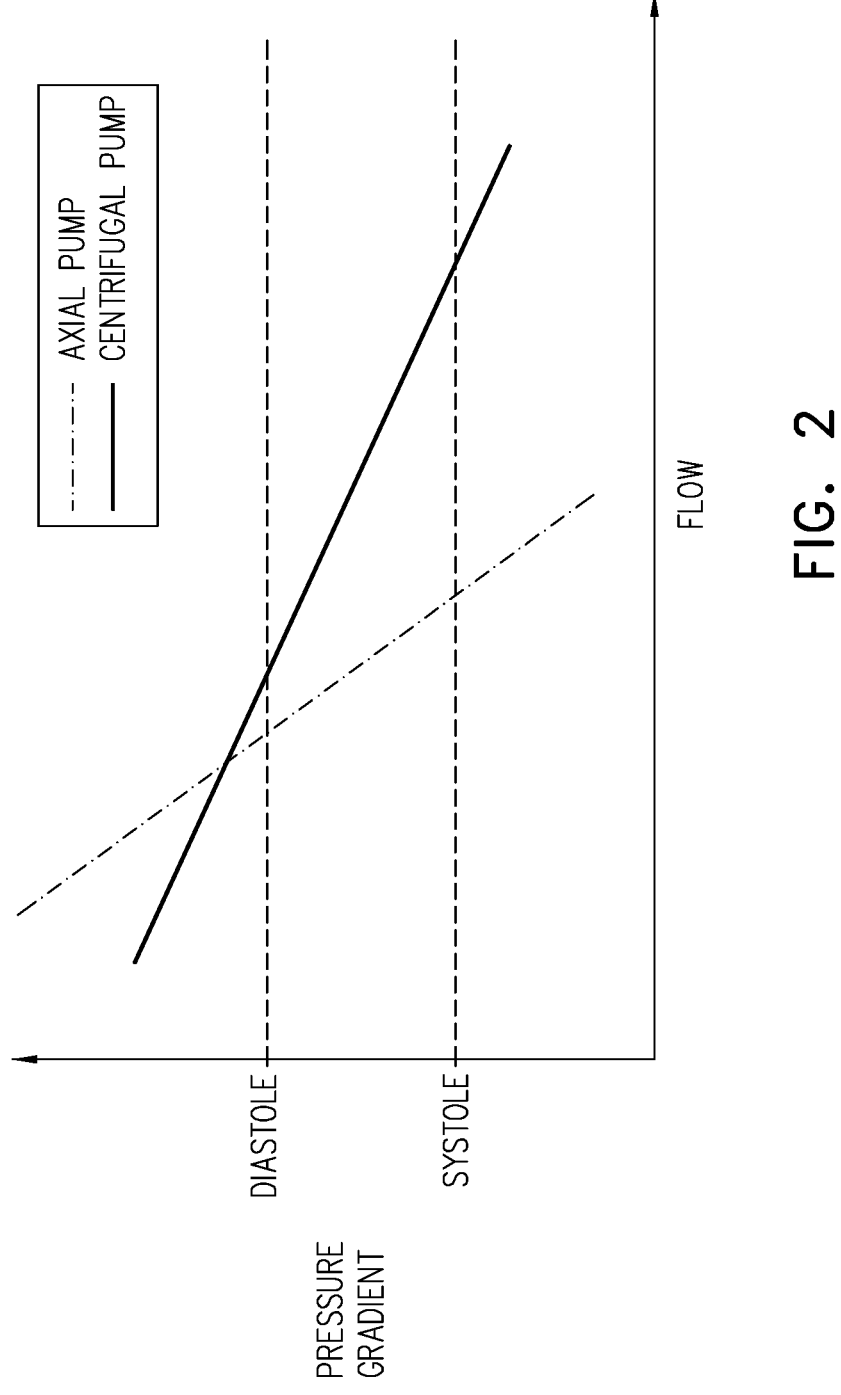
FIG. 2 is a graph showing pressure-flow curves, respectively, for axially-pumping impellers, and for centrifugally-pumping impellers, such as centrifugally-pumping impellers that are used in accordance with some applications of the present invention.

Reference is now made to FIG. 2, which is a graph showing pressure-flow curves, respectively, for axially-pumping impellers and for centrifugally-pumping impellers, such as impellers 24 of the present application. The curves schematically illustrate the flow that is generated by the impellers when they are pumping against a given pressure gradient, with the dashed lines added to the graph to illustrate the pressure gradients, respectively, at diastole and systole. As shown, it is typically the case the that the pressure-flow curve of a centrifugally-pumping impeller is flatter than that of an axially-pumping impeller. Typically, this results in the flow (and arterial pressure) that is generated by a centrifugally-pumping impeller being more pulsatile than that generated by an axially-pumping impeller, since there is a greater change in flow between diastole and systole. In some patients, it may be desirable for the patient's arterial blood pressure to maintain pulsatility even while a treatment is being provided to the patient to assist with the patient's left-ventricular functioning. Therefore, in accordance with some applications, centrifugally-pumping impellers 24 are used in ventricular assist device 20. Alternatively or additionally, ventricular assist device 20 includes centrifugally-pumping impellers 24 due to other considerations.

Figure 3:
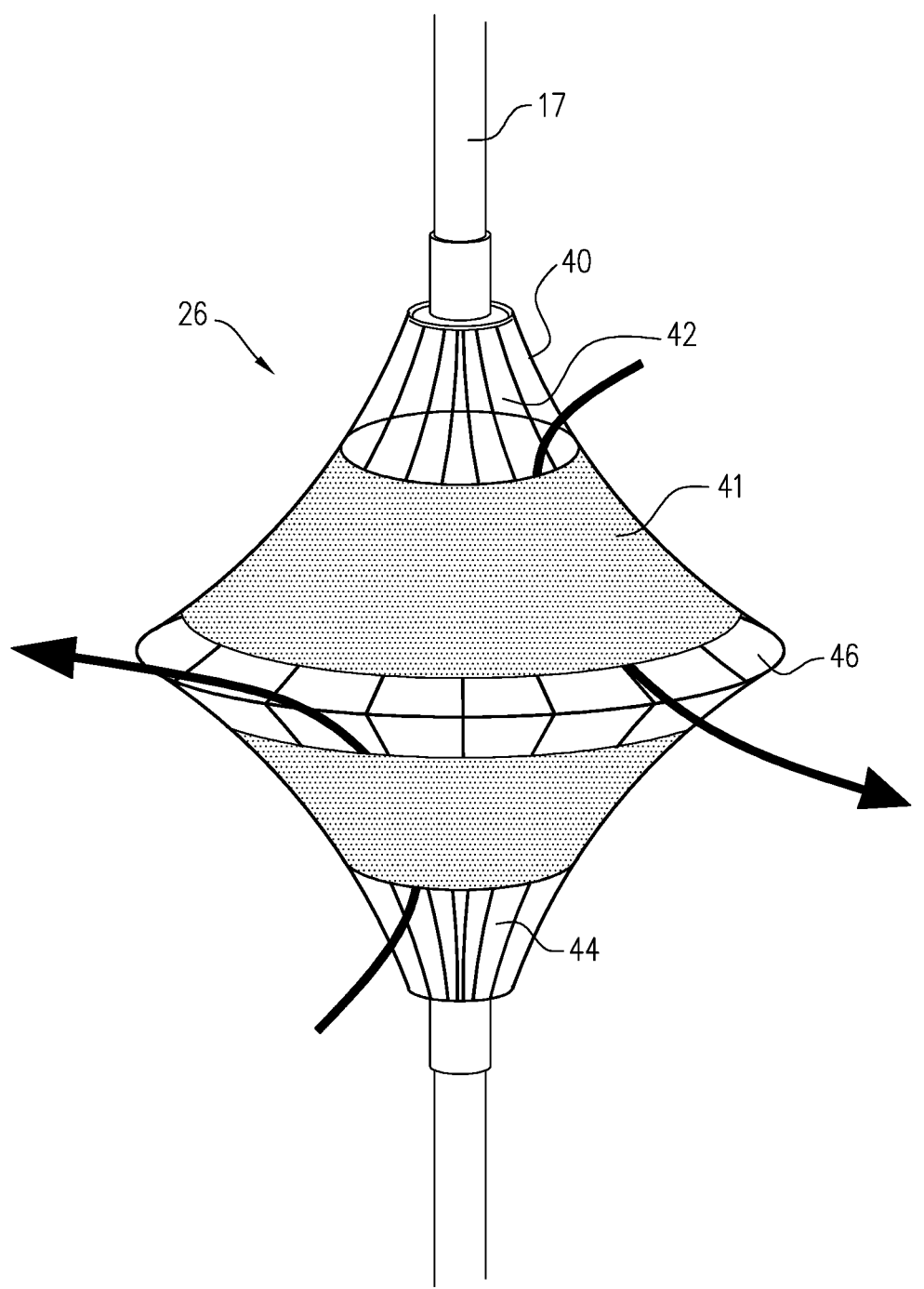
FIG. 3 is a schematic illustration of an impeller housing, in a non-radially-constrained configuration, in accordance with some applications of the present invention.

Reference is now made to FIG. 3, which is a schematic illustration of impeller housing 26, in a non-radially-constrained configuration, in accordance with some applications of the present invention. Typically the impeller housing is radially expandable (e.g., radially self-expandable), such that the impeller housing may be delivered while it is disposed in a radially-constrained configuration inside delivery catheter 34, and may subsequently be deployed in a non-radially-constrained configuration inside the left ventricle. For some applications, the impeller housing includes a self-expandable frame 40, which is typically made of a shape-memory alloy, such as nitinol. Typically, the frame is a stent-like frame, in that it comprises struts that typically, in turn, define cells. For some applications, at least a portion of the frame is covered with a covering material 41, such as silicone, polyurethane, polyester, polyethylene terephthalate (PET), and/or polyether block amide (e.g., PEBAX®). For some applications, the covering is disposed around the frame, such as to define an upper blood-inlet opening 42 and a lower blood-inlet opening 44. During operation of the centrifugally-pumping impeller, blood is pumped into impeller housing 26 by the impeller via both the upper blood-inlet opening and the lower blood-inlet opening. Typically, this increases the volume of blood that is pumped into the housing by the impeller relative to if the impeller housing only defined a single blood-inlet opening. For some applications, covering material 41 is disposed around the frame, such as to define a blood-outlet portion 46. Typically, the blood-outlet portion is a circumferential portion of the frame that is not covered by covering material 41. Further typically, volute 27 surrounds the blood outlet portion, as described in further detail hereinbelow. For some applications, the impeller housing is radially constrained by axially elongating the frame, such that the diameter of the frame is decreased.

Figure 4:
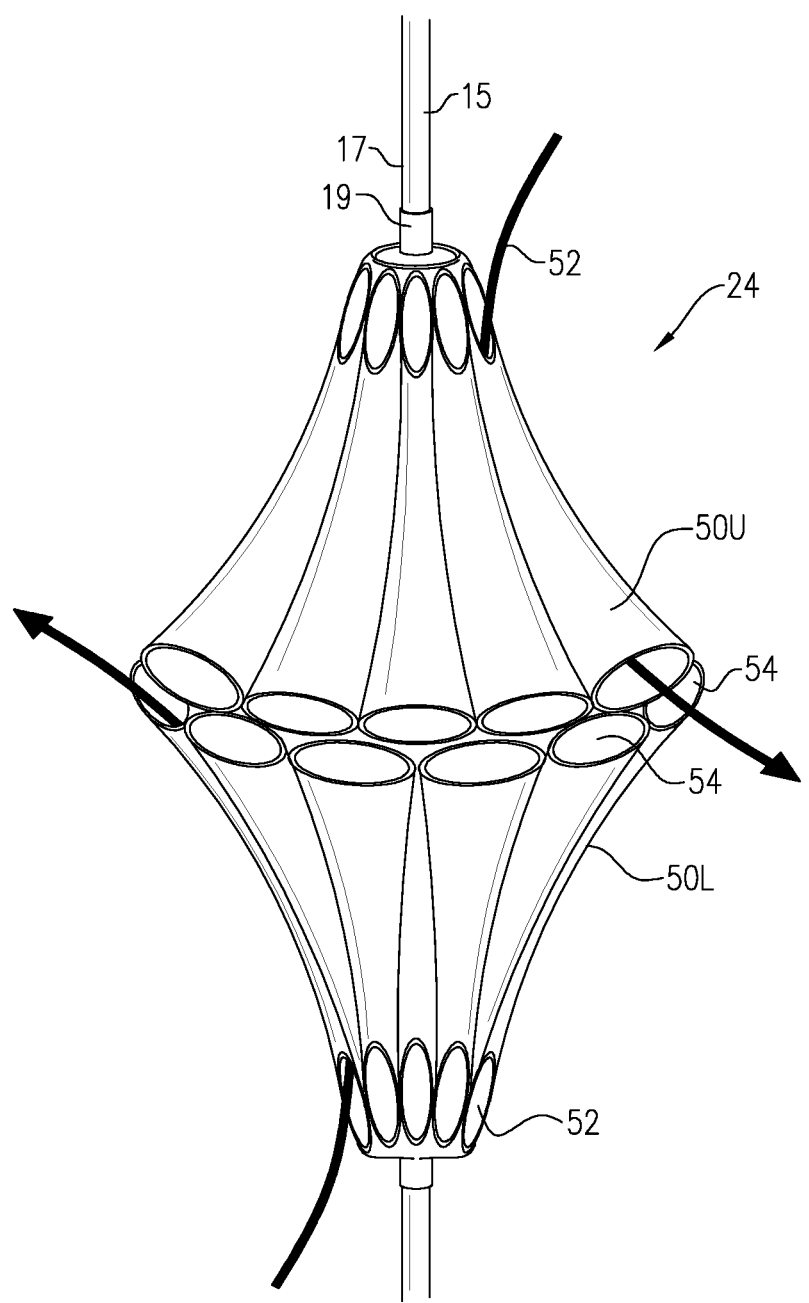
FIG. 4 is a schematic illustration of a centrifugally-pumping impeller, in a non-radially-constrained configuration, in accordance with some applications of the present invention.

Reference is now made to FIG. 4, which is a schematic illustration of centrifugally-pumping impeller 24, in a non-radially-constrained configuration, in accordance with some applications of the present invention. For some applications, in its non-radially-constrained configuration, the impeller defines a plurality of blood-flow channels 50U or 50L, each of which channels blood from an axially-facing, blood-inlet opening 52 that is disposed at an upper or lower end of the impeller, to a radially-facing, blood-outlet opening 54 that is disposed between the upper and lower ends of the impeller, e.g., toward or at the axial center of the impeller. Typically, the impeller includes at least one upper blood-flow channel 50U that defines a blood-inlet opening at the upper end of the impeller and at least one lower blood-flow channel 50L that defines a blood-inlet opening at the lower end of the impeller. For some applications, each of the blood-flow channels is individually constructed. Alternatively, the blood-channels are defined by an element, such as a frame (e.g., a shape-memory alloy frame, such as a nitinol frame) that is dipped in a material (e.g., a polymer, such as an elastomeric polymer, silicone, polyurethane, polyester, polyethylene terephthalate (PET), and/or polyether block amide (e.g., PEBAX®)), with the material being made to cover the frame such as to define the blood-flow channels (e.g., via the dipping process, and/or by cutting the material).

It is noted that, for some applications, the blood-inlet openings are disposed at an angle with respect to the axial direction, and/or the blood-outlet openings are disposed at an angle with respect to the radial direction. However, it is typically the case that the blood-inlet openings are substantially axially facing, and the blood-outlet openings are substantially radially facing.

The blood-flow channels are typically coupled to axial shaft 19 in such a manner that during insertion of the impeller via delivery catheter 34 (shown in FIG. 1B), the blood-flow channels are radially constrained by one or both ends of the blood-flow channels sliding axially with respect to the axial shaft. An example of this is described in further detail hereinbelow with reference to FIGS. 10A-C.

Typically, during operation of the centrifugally-pumping impeller, the impeller is disposed in its non-radially-constrained configuration. While disposed in its non-radially-constrained configuration, the impeller is driven to rotate, by the motor rotating the drive cable, and the drive cable rotating axial shaft 19, to which the blood-flow-channels are coupled. The rotation of the impeller causes the impeller to draw blood in through the axially-facing blood-inlet openings 52 of the blood-flow channels (and through blood-inlet openings 42, 44 of the impeller housing, shown in FIG. 3), and to pump blood out of radially-facing blood outlet openings 54 (and out of blood-outlet portion 46 of the impeller housing, shown in FIG. 3).

Figure 5A:
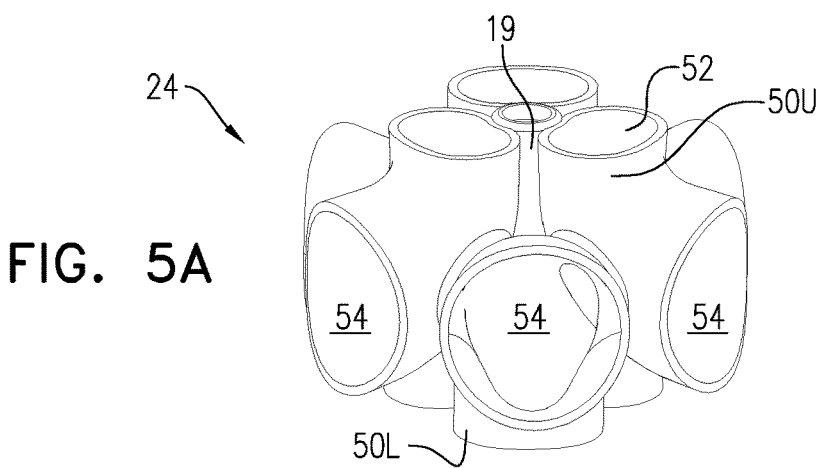
FIGS. 5A, 5B, 5C, and 5D are schematic illustrations of respective views of a centrifugally-pumping impeller, in accordance with some applications of the present invention.
Figures 5B, 5C:
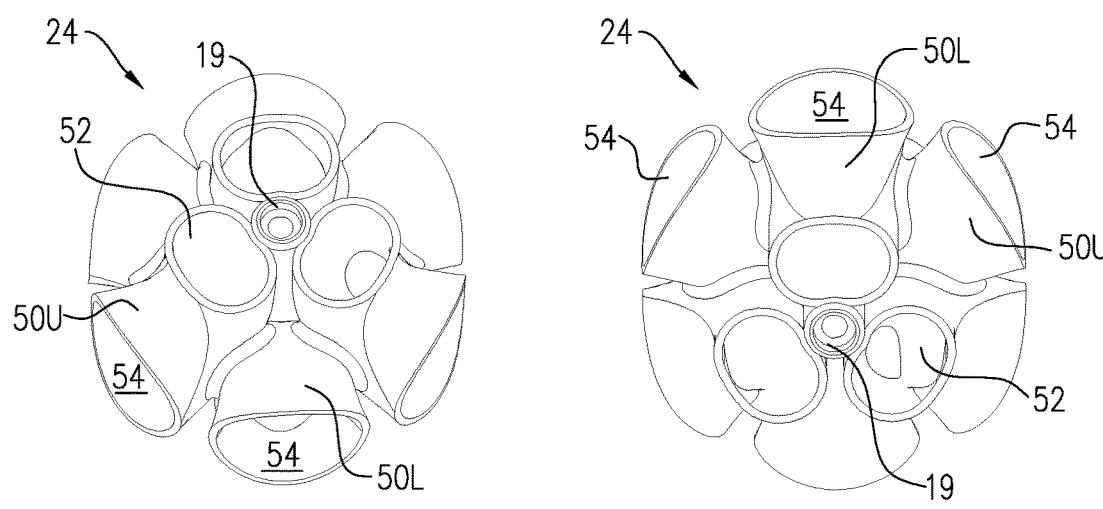
Figure 5D:
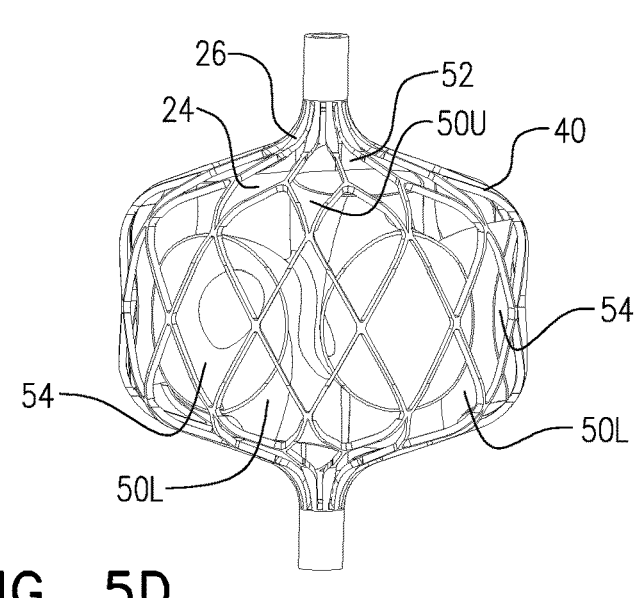

Reference is now made to FIGS. 5A, 5B, 5C, and 5D which are schematic illustrations of respective views of centrifugally-pumping impeller 24, in accordance with some applications of the present invention. FIG. 5A shows a side view of the impeller, FIG. 5B shows a top view, FIG. 5C shows a bottom view, and FIG. 5D shows a side view of the impeller disposed inside frame 40 of impeller housing 26. (For illustrative purposes, frame 40 is shown in the absence of covering material 41 in FIG. 5D.) As described hereinabove, typically, the impeller includes at least one upper blood-flow channel 50U that defines a blood-inlet opening at the upper end of the impeller and at least one lower blood-flow channel 50L that defines a blood-inlet opening at the lower end of the impeller. As shown, for some applications, blood-outlet openings defined by the upper and lower blood-flow channels are disposed around the circumference of the impeller at the same axial location as each other, and alternate with each other around the circumference of the impeller. For some applications, the blood-flow channels of the impeller do not define any circumferential curvature. Rather, as shown in FIGS. 5A-D, each of the blood-flow channels curves through 90 degrees from the axially-facing blood-inlet opening 52 to the radially-facing blood-outlet opening 54.

Figure 6A:
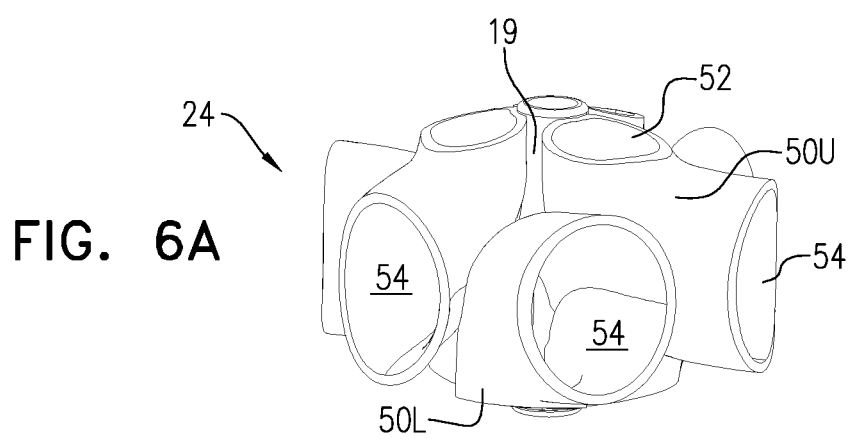
FIGS. 6A, 6B, and 6C are schematic illustrations of respective views of a centrifugally-pumping impeller, in accordance with some alternative applications of the present invention.
Figure 6B:
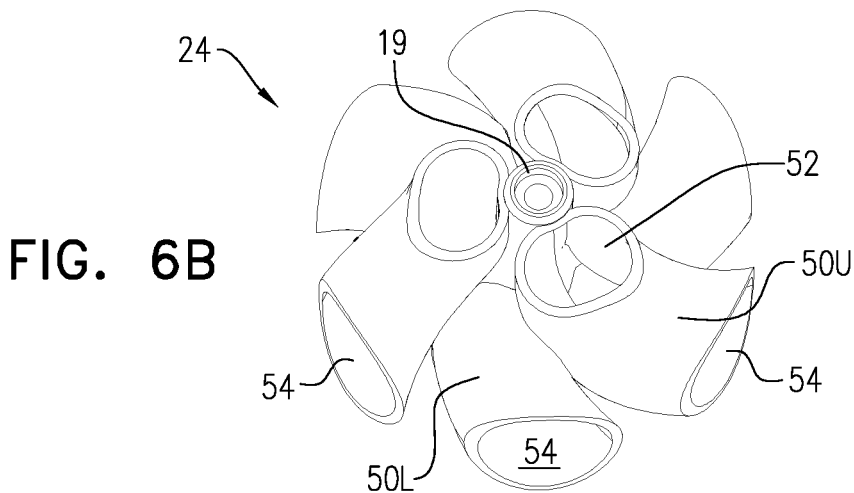
Figure 6C:
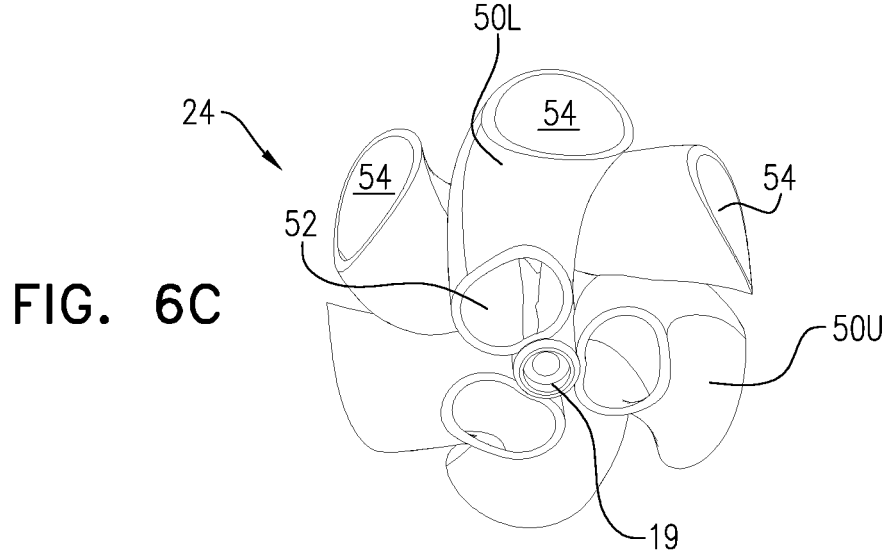

Reference is now made to FIGS. 6A, 6B, and 6C, which are schematic illustrations of respective views of centrifugally-pumping impeller 24, in accordance with some applications of the present invention. FIG. 6A shows a side view of the impeller, FIG. 6B shows a top view, and FIG. 6C shows a bottom view. As described hereinabove, typically, the impeller includes at least one upper blood-flow channel 50U that defines a blood-inlet opening at the upper end of the impeller and at least one lower blood-flow channel 50L that defines a blood-inlet opening at the lower end of the impeller. As shown, for some applications, blood-outlet openings defined by the upper and lower blood-flow channels are disposed around the circumference of the impeller at the same axial location as each other, and alternate with each other around the circumference of the impeller. For some applications, the blood-flow channels of the impeller define a circumferential curvature. For example, as shown in FIGS. 6A-C, each of the blood-flow channels curves through 90 degrees from the axially-facing blood-inlet opening 52 to the radially-facing blood-outlet opening 54, and additionally curves circumferentially around the axial shaft.

Figure 7A:
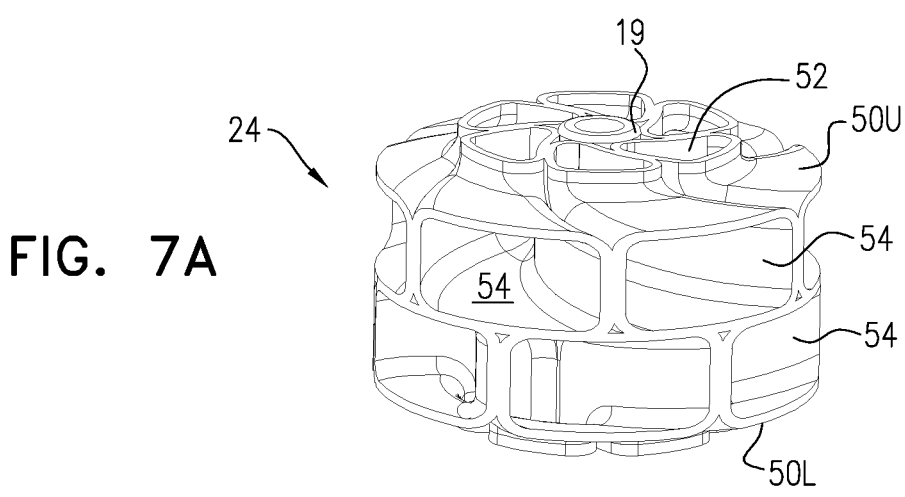
FIGS. 7A, 7B, and 7C are schematic illustrations of respective views of a centrifugally-pumping impeller, in accordance with some further alternative applications of the present invention.
Figure 7B:
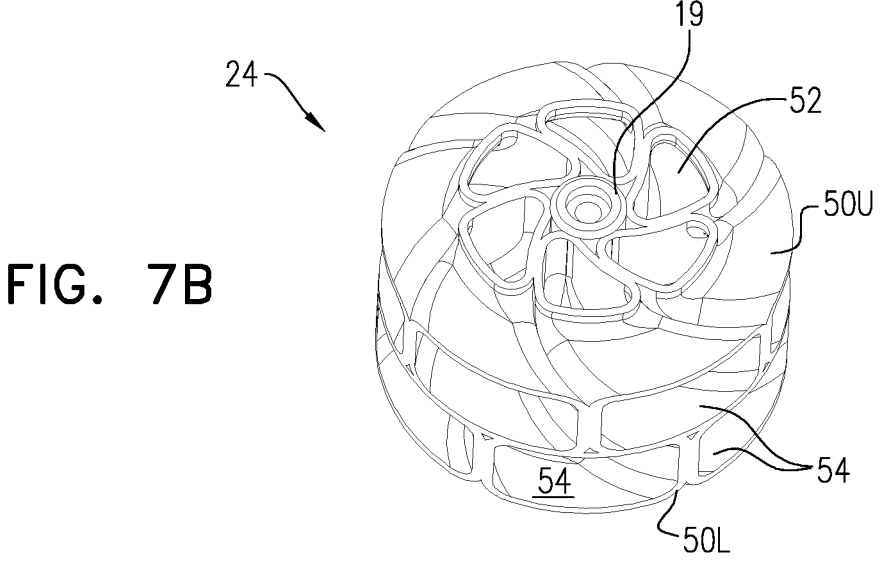
Figure 7C:
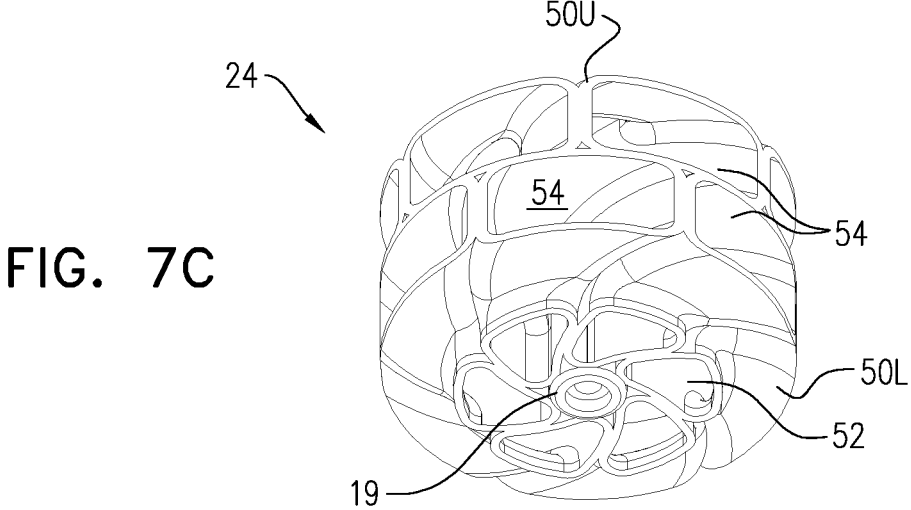

Reference is now made to FIGS. 7A, 7B, and 7C, which are schematic illustrations of respective views of centrifugally-pumping impeller 24, in accordance with some applications of the present invention. FIG. 7A shows a side view of the impeller, FIG. 7B shows a top view, and FIG. 7C shows a bottom view. As described hereinabove, typically, the impeller includes at least one upper blood-flow channel 50U that defines a blood-inlet opening at the upper end of the impeller and at least one lower blood-flow channel 50L that defines a blood-inlet opening at the lower end of the impeller. As shown, for some applications, blood-outlet openings defined by the upper and lower blood-flow channels are disposed around the circumference of the impeller at different axial locations from each other, with the blood-outlet openings of the upper blood-flow channels typically disposed above those of the lower blood-flow channels. For some applications, the blood-outlet openings at the upper and lower axial locations are staggered with respect to each other, as shown in FIGS. 7A-C. For some applications, the blood-flow channels of the impeller define a circumferential curvature. For example, as shown in FIGS. 7A-C, each of the blood-flow channels curves through 90 degrees from the axially-facing blood-inlet opening 52 to the radially-facing blood-outlet opening 54, and additionally curves circumferentially around the axial shaft.

Figure 8A:
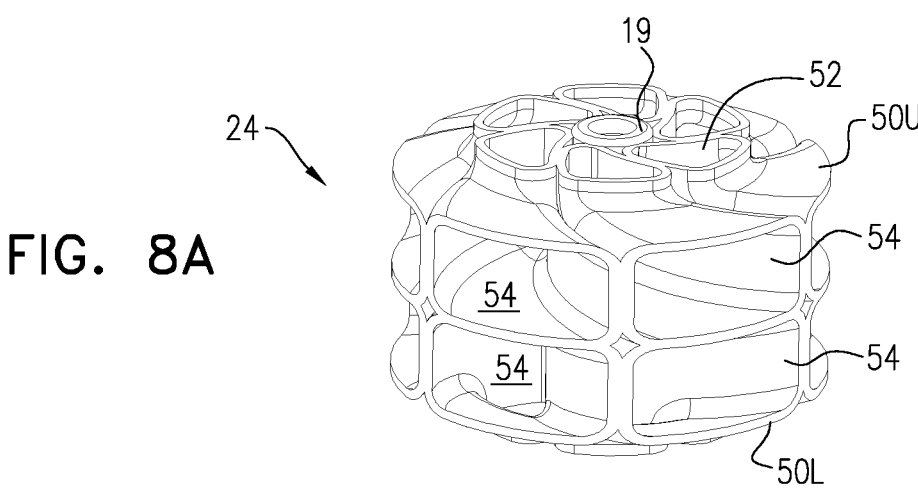
FIGS. 8A, 8B, and 8C are schematic illustrations of respective views of a centrifugally-pumping impeller, in accordance with some still further alternative applications of the present invention.
Figure 8B:
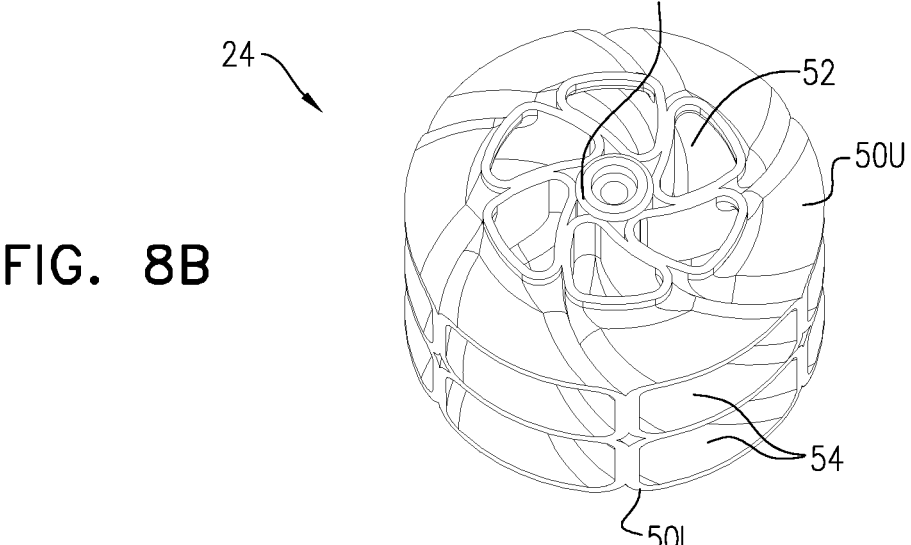
Figure 8C:
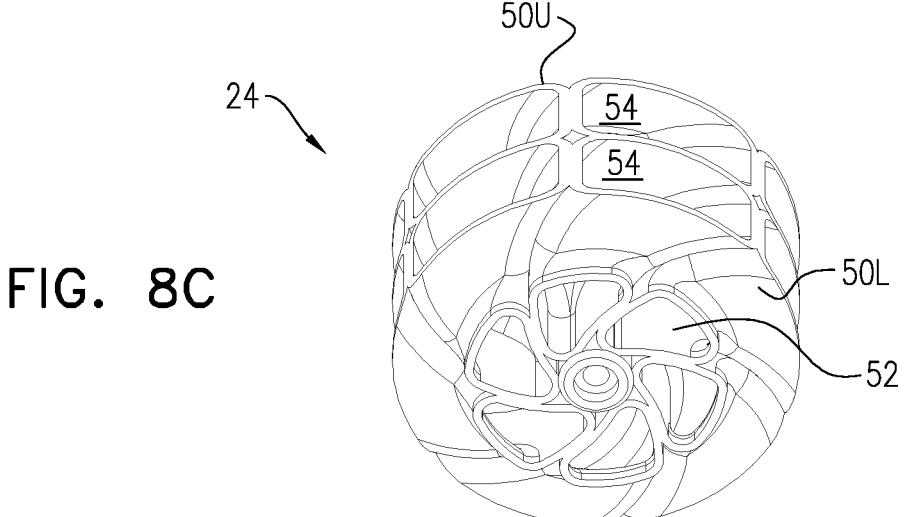

Reference is now made to FIGS. 8A, 8B, and 8C, which are schematic illustrations of respective views of centrifugally-pumping impeller 24, in accordance with some applications of the present invention. FIG. 8A shows a side view of the impeller, FIG. 8B shows a top view, and FIG. 8C shows a bottom view. As described hereinabove, typically, the impeller includes at least one upper blood-flow channel 50U that defines a blood-inlet opening at the upper end of the impeller and at least one lower blood-flow channel 50L that defines a blood-inlet opening at the lower end of the impeller. As shown, for some applications, blood-outlet openings defined by the upper and lower blood-flow channels are disposed around the circumference of the impeller at the different axial locations from each other, with the blood-outlet openings of the upper blood-flow channels typically disposed above those of the lower blood-flow channels. For some applications, the blood-outlet openings at the upper and lower axial locations are not staggered with respect to each other. Rather, a single blood-outlet opening is disposed at the upper axial location above a single corresponding blood-outlet opening disposed at the lower axial location, as shown in FIGS. 8A-C. For some applications, the blood-flow channels of the impeller define a circumferential curvature. For example, as shown in FIGS. 8A-C, each of the blood-flow channels curves through 90 degrees from the axially-facing blood-inlet opening 52 to the radially-facing blood-outlet opening 54, and additionally curves circumferentially around the axial shaft.

With reference to each of the examples of the blood-flow channels shown in FIGS. 5A-8C, it is noted that it is typically the case that the blood-flow channel widens from the blood-inlet opening to the blood-outlet opening, i.e., the cross-sectional area of the channel increases from the blood-inlet opening to the blood-outlet opening.

Figures 9A, 9B, 9C:
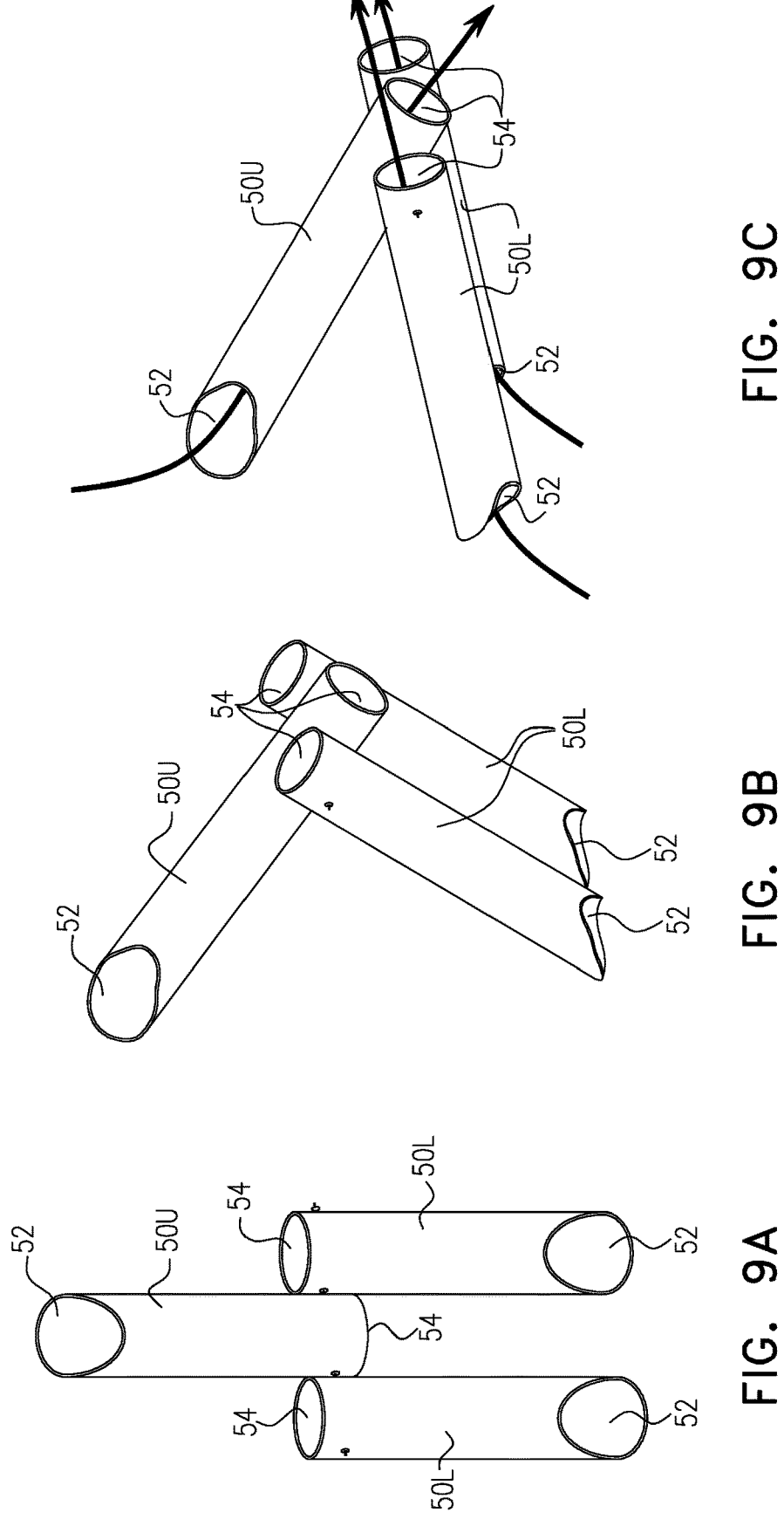
FIGS. 9A, 9B, and 9C are schematic illustrations of blood-flow channels of an impeller in respective states of radial constraint, in accordance with some applications of the present invention.

Reference is now made to FIGS. 9A, 9B, and 9C, which are schematic illustrations of blood-flow channels 50U and 50L of an impeller in respective states of radial constraint, in accordance with some applications of the present invention. As described hereinabove, typically, the impeller includes at least one upper blood-flow channel 50U that defines a blood-inlet opening at the upper end of the impeller and at least one lower blood-flow channel 50L that defines a blood-inlet opening at the lower end of the impeller. For some applications, each of the blood-flow channels comprises a tube, and the upper and lower blood-flow channels alternate with each other around the circumference of the impeller. Each of the tubes that defines the blood-flow channels typically defines a first hole at its first end that the defines blood-inlet opening 52 and a second hole at its second end that defines blood-outlet opening 54. Typically, in the non-radially-constrained configuration of the impeller (shown in FIG. 9C), the blood-flow channels are disposed at an angle with respect to the axis of the impeller, such that the blood outlet openings are substantially radially facing. In the radially-constrained configuration of the impeller (shown in FIG. 9A), the blood-flow channels are substantially aligned with the axis of the impeller. FIG. 9B shows the blood-flow channels during the transition from the radially-constrained configuration to the non-radially-constrained configuration of the impeller.

Figure 10A:
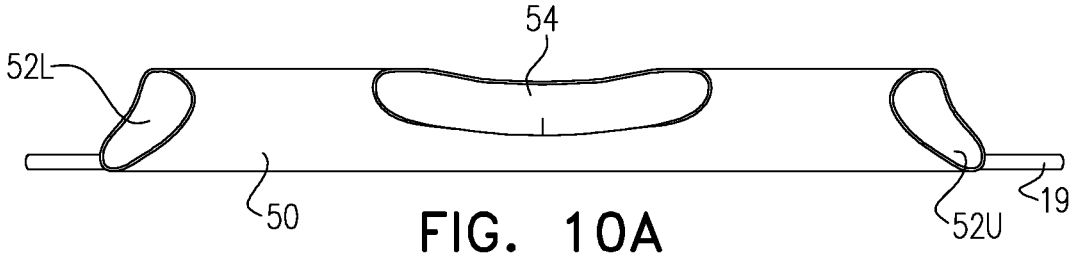
FIGS. 10A, 10B, and 10C are schematic illustrations of a blood-flow channel of an impeller in respective states of radial constraint, in accordance with some applications of the present invention.
Figure 10B:
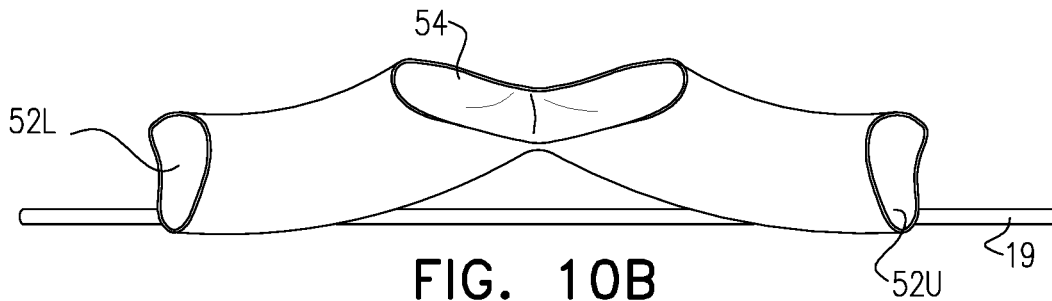
Figure 10C:
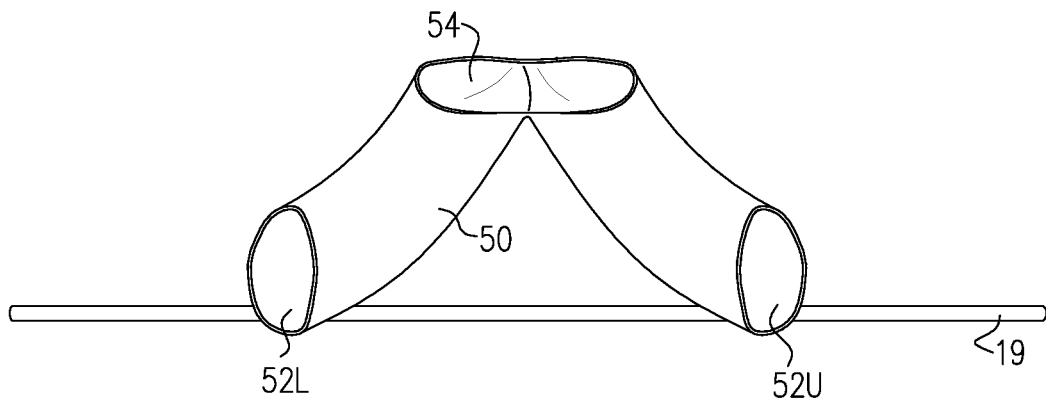

Reference is now made to FIGS. 10A, 10B, and 10C, which are schematic illustrations of a blood-flow channel 50 of an impeller in respective states of radial constraint, in accordance with some applications of the present invention. For some applications, a single blood-flow channel 50 defines an upper blood-inlet opening 52U at the upper end of the impeller and a lower blood-inlet opening 52L at the lower end of the impeller, in addition to a blood-outlet opening 54 between the upper and lower ends. Typically, in the non-radially-constrained configuration of the impeller (shown in FIG. 10C), the blood-flow channel forms a laterally-facing V-shape or U-shape with respect to axial shaft 19, with the blood-outlet opening facing radially outwardly at the center of the V-shape or U-shape. In the radially-constrained configuration of the impeller (shown in FIG. 10A), the blood-flow channel is substantially aligned with the axial shaft. FIG. 10B shows the blood-flow channel during the transition from the radially-constrained configuration to the non-radially-constrained configuration of the impeller.

Figures 11A, 11B:
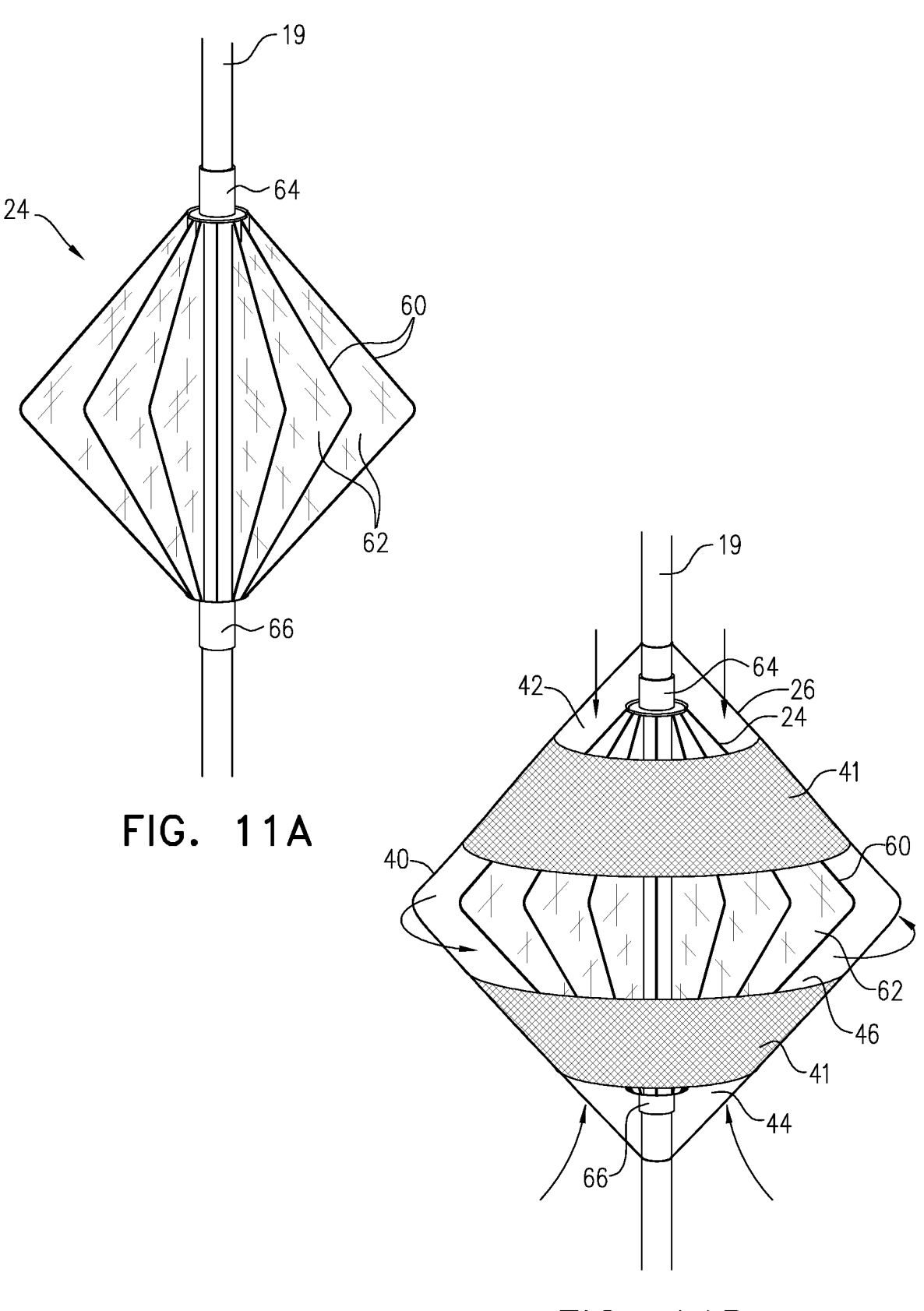
FIGS. 11A and 11B are schematic illustrations of a biconical centrifugally-pumping impeller, in accordance with some applications of the present invention.

Reference is now made to FIGS. 11A and 11B, which are schematic illustrations of centrifugally-pumping impeller 24 in a non-radially-constrained configuration, the impeller being a biconical centrifugally-pumping impeller, in accordance with some applications of the present invention. FIG. 11A shows just the impeller, and FIG. 11B shows the impeller disposed inside impeller housing 26. For some applications, the impeller has a generally biconical shape. Typically, the impeller is constructed from a self-expandable frame 60, which is typically made of a shape-memory alloy, such as nitinol. For some applications, at least a portion of the frame is covered with a covering material 62, such as silicone, polyurethane, polyester, polyethylene terephthalate (PET), and/or polyether block amide (e.g., PEBAX®). For some applications, frame 60 includes struts that extend between a proximal bushing 64 and a distal bushing 66. Typically, one of the bushings is coupled to axial shaft 19, and the other bushing is axially slidable with respect to axial shaft 19. For some applications, during insertion of the impeller via delivery catheter 34 (shown in FIG. 1B), the impeller is radially constrained by the slidable bushing sliding axially with respect to the axial shaft.

Typically, during operation of the centrifugally-pumping impeller, the impeller is disposed in its non-radially-constrained configuration (shown in FIGS. 11A-B). While disposed in its non-radially-constrained configuration, the impeller is driven to rotate, by the motor rotating the drive cable, and the drive cable rotating axial shaft 19, to which frame 60 is coupled. The rotation of the impeller causes the impeller to draw blood in through blood-inlet openings 42, 44 of the impeller housing (shown in FIG. 11B), and to pump blood out of blood-outlet portion 46 of the impeller housing (shown in FIG. 11B).

Figure 12A:
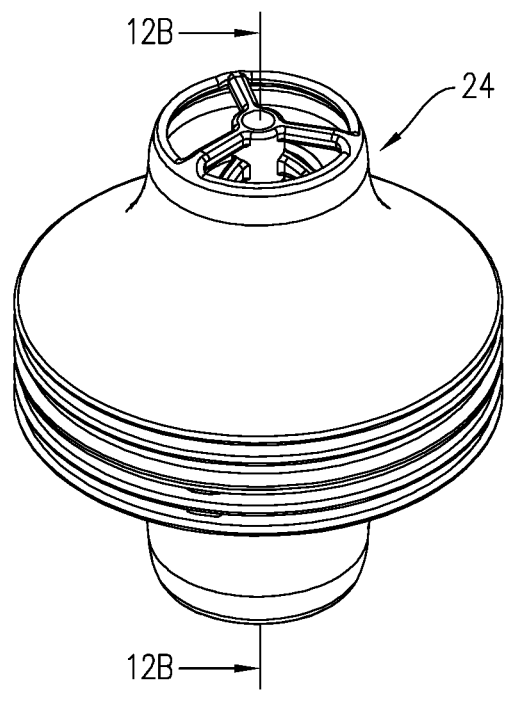
FIGS. 12A, 12B, and 12C are schematic illustrations a multi-layered, biconical centrifugally-pumping impeller, in accordance with some applications of the present invention.
Figure 12B:
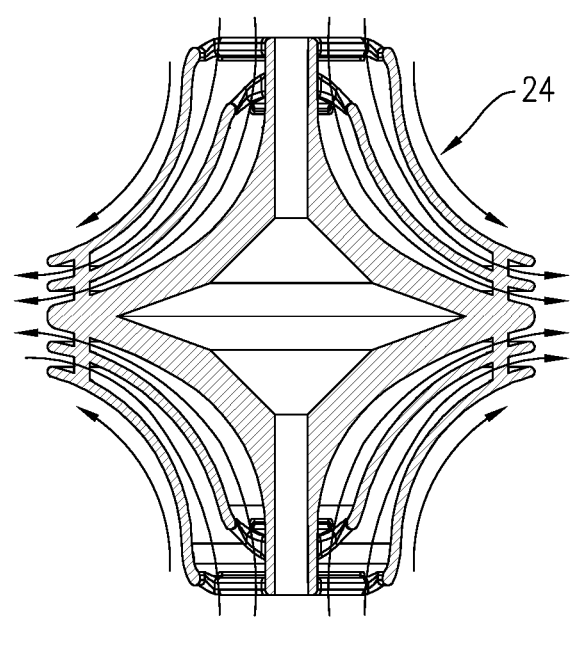
Figure 12C:
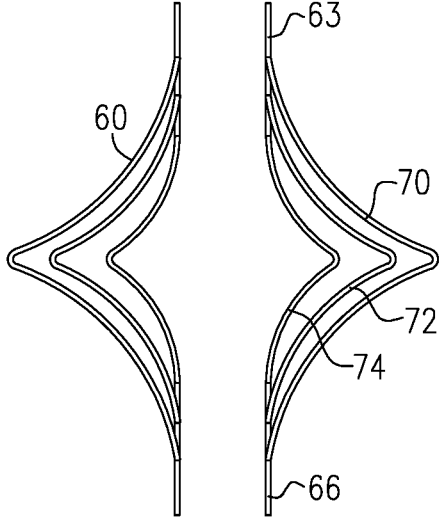
Figures 13A, 13B:
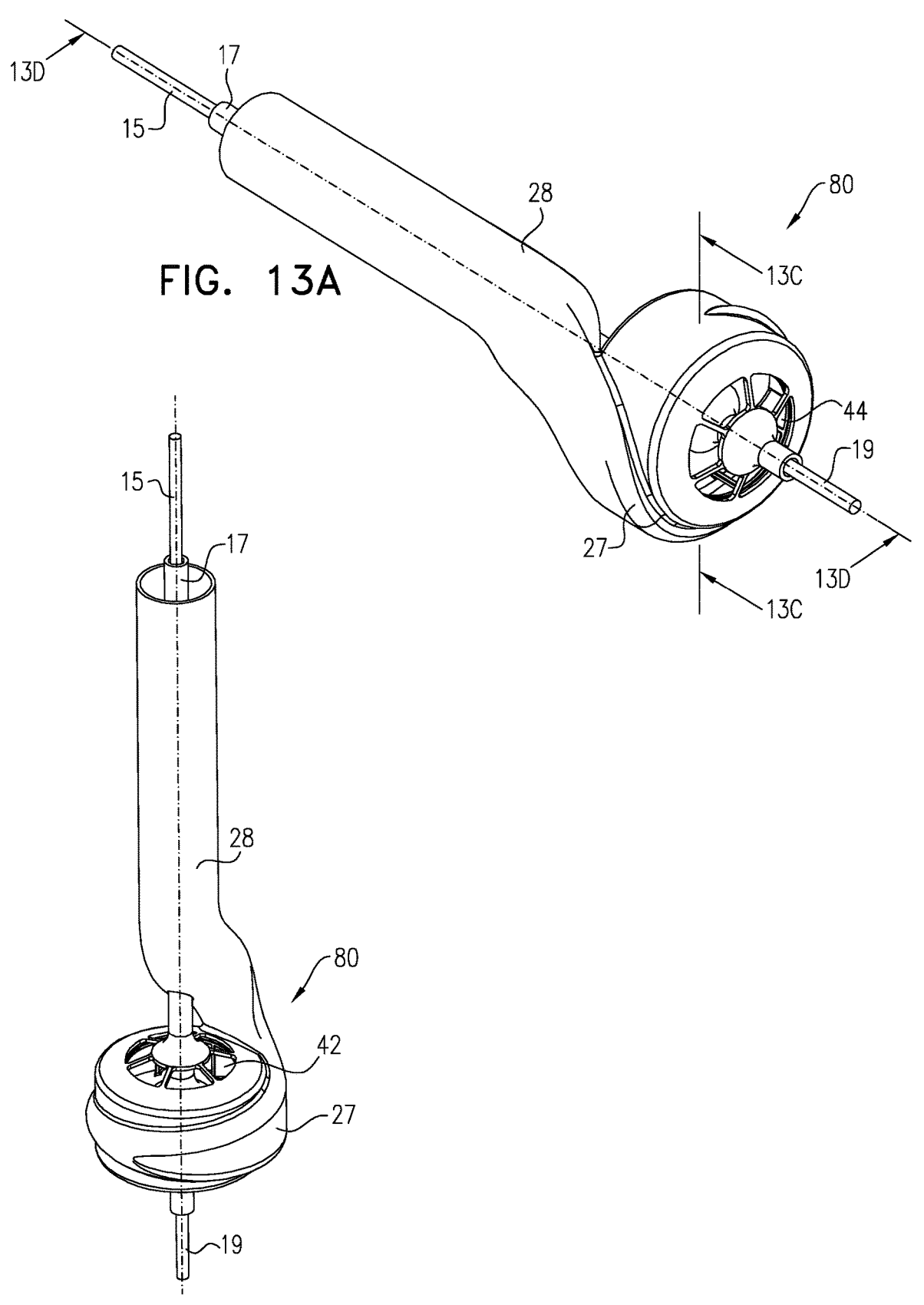
FIGS. 13A, 13B, 13C, and 13D are schematic illustrations of a pump-head portion of a ventricular assist device, in accordance with some applications of the present invention.
Figures 13C, 13D:
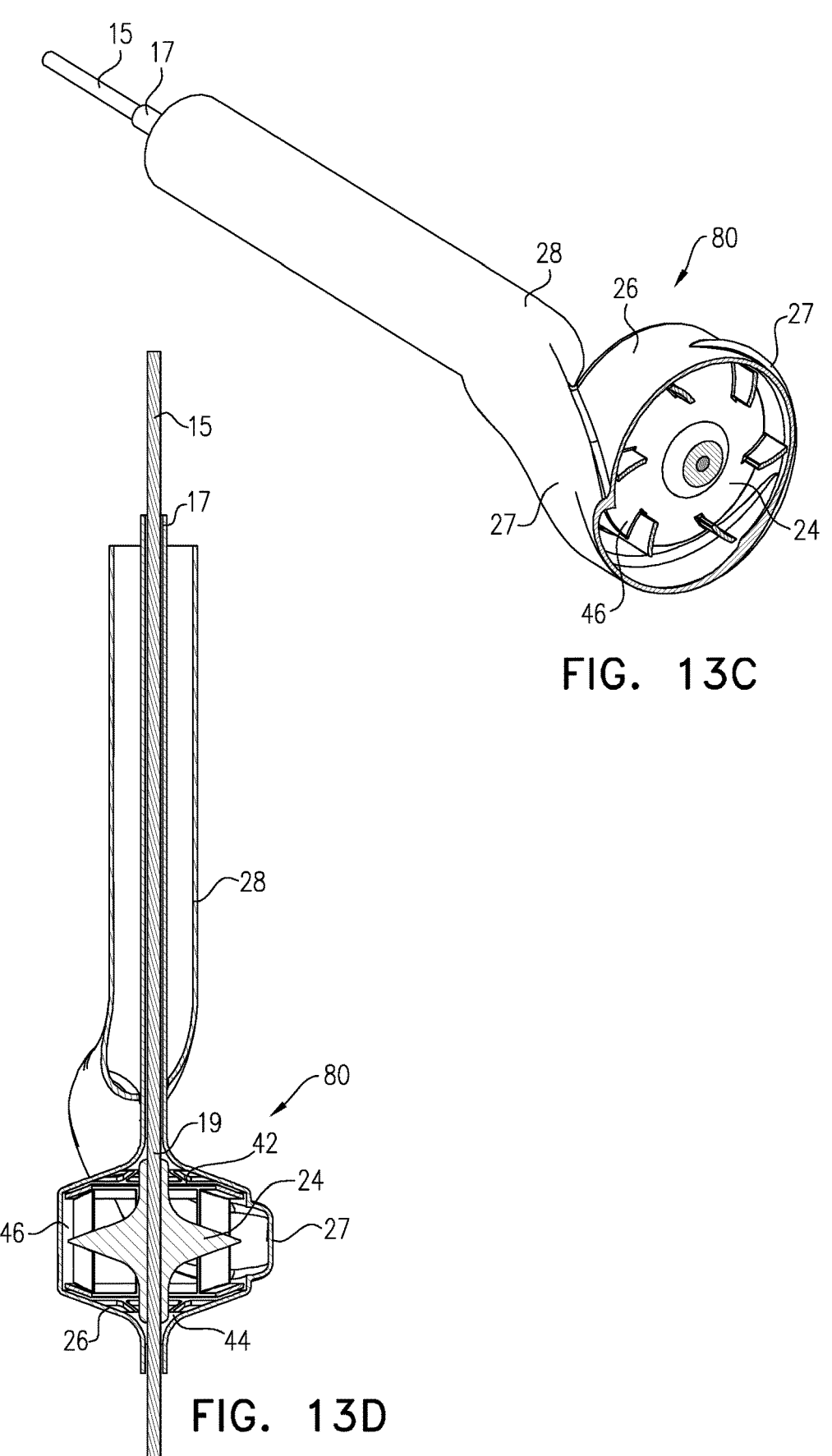
Figures 14A, 14B:
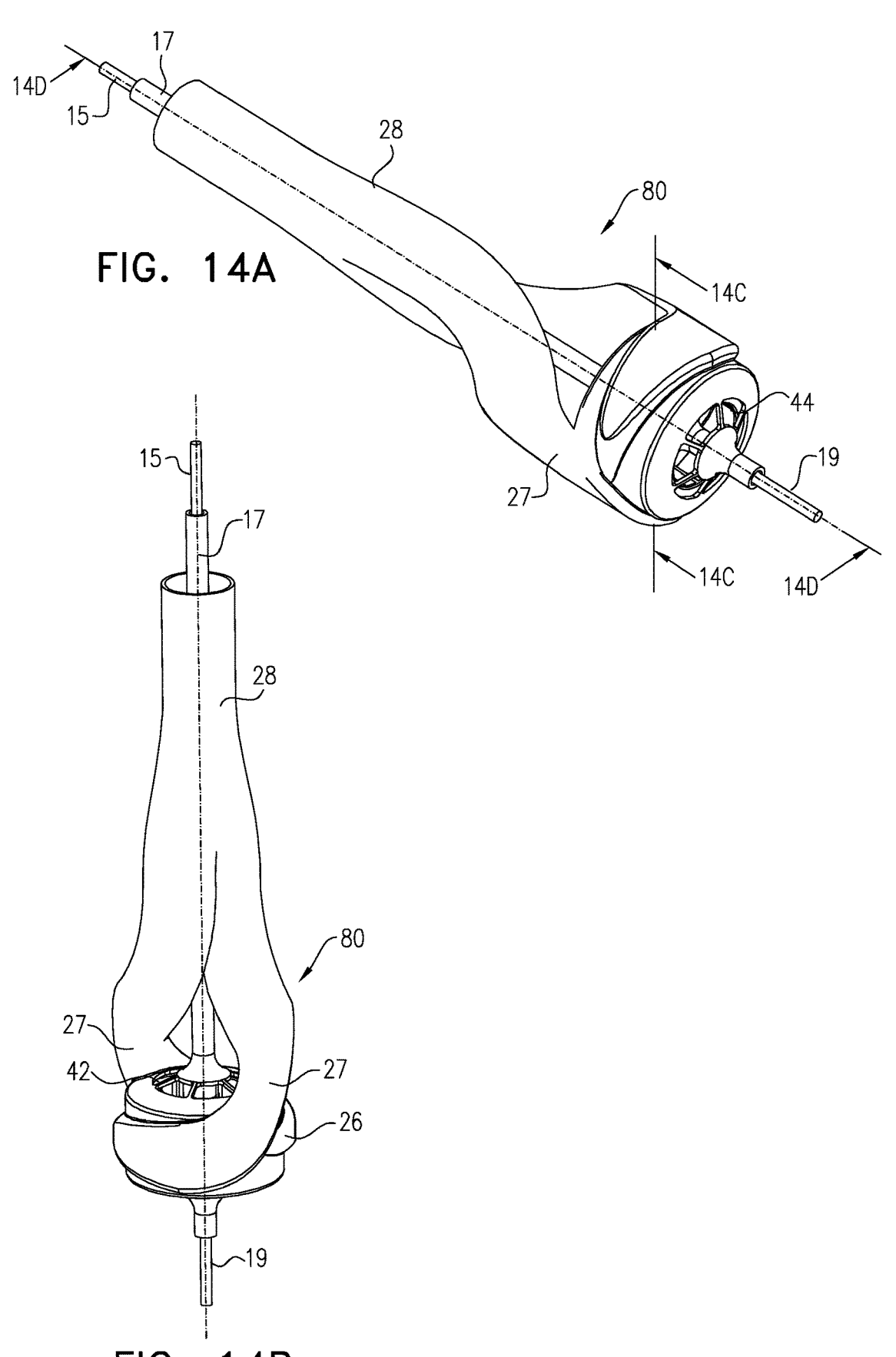
FIGS. 14A, 14B, 14C, and 14D are schematic illustrations of a pump-head portion of a ventricular assist device, in accordance with some alternative applications of the present invention.
Figures 14C, 14D:
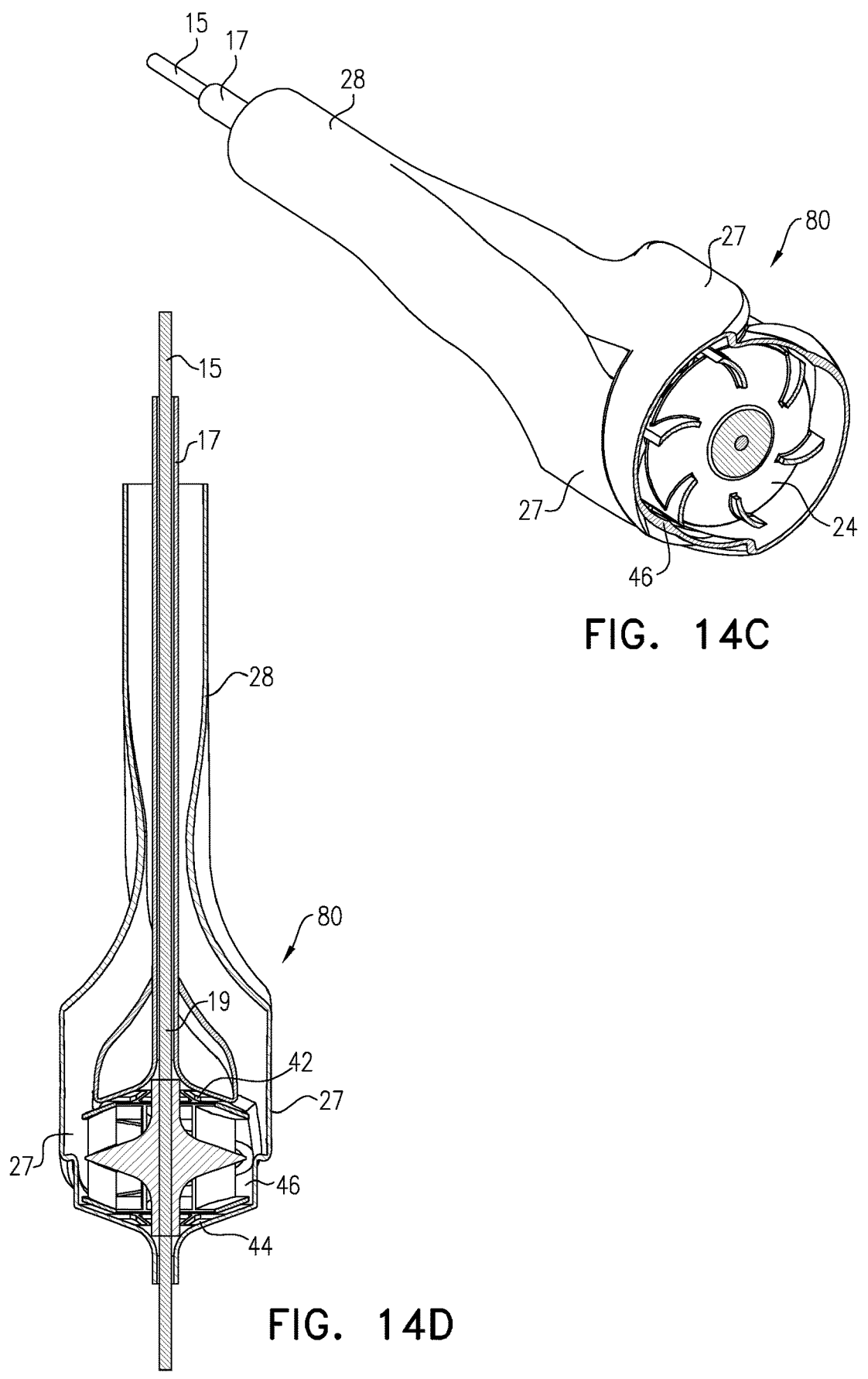
Figures 15A, 15B:
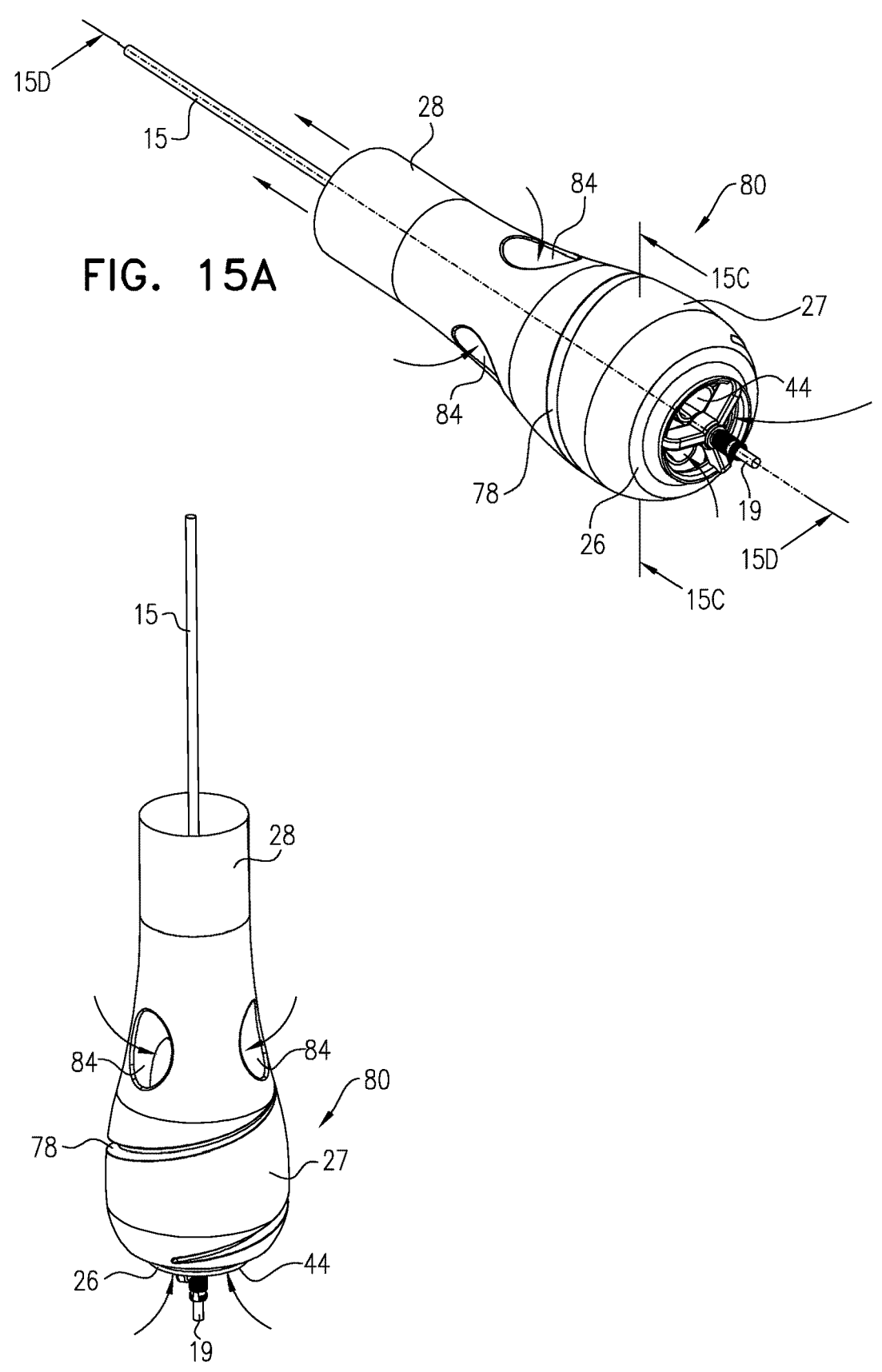
FIGS. 15A, 15B, 15C, and 15D are schematic illustrations of a pump-head portion of a ventricular assist device that includes one or more blood inlet tubes that pass through a volute and/or a pump-outlet tube, in accordance with some applications of the present invention.
Figures 15C, 15D:
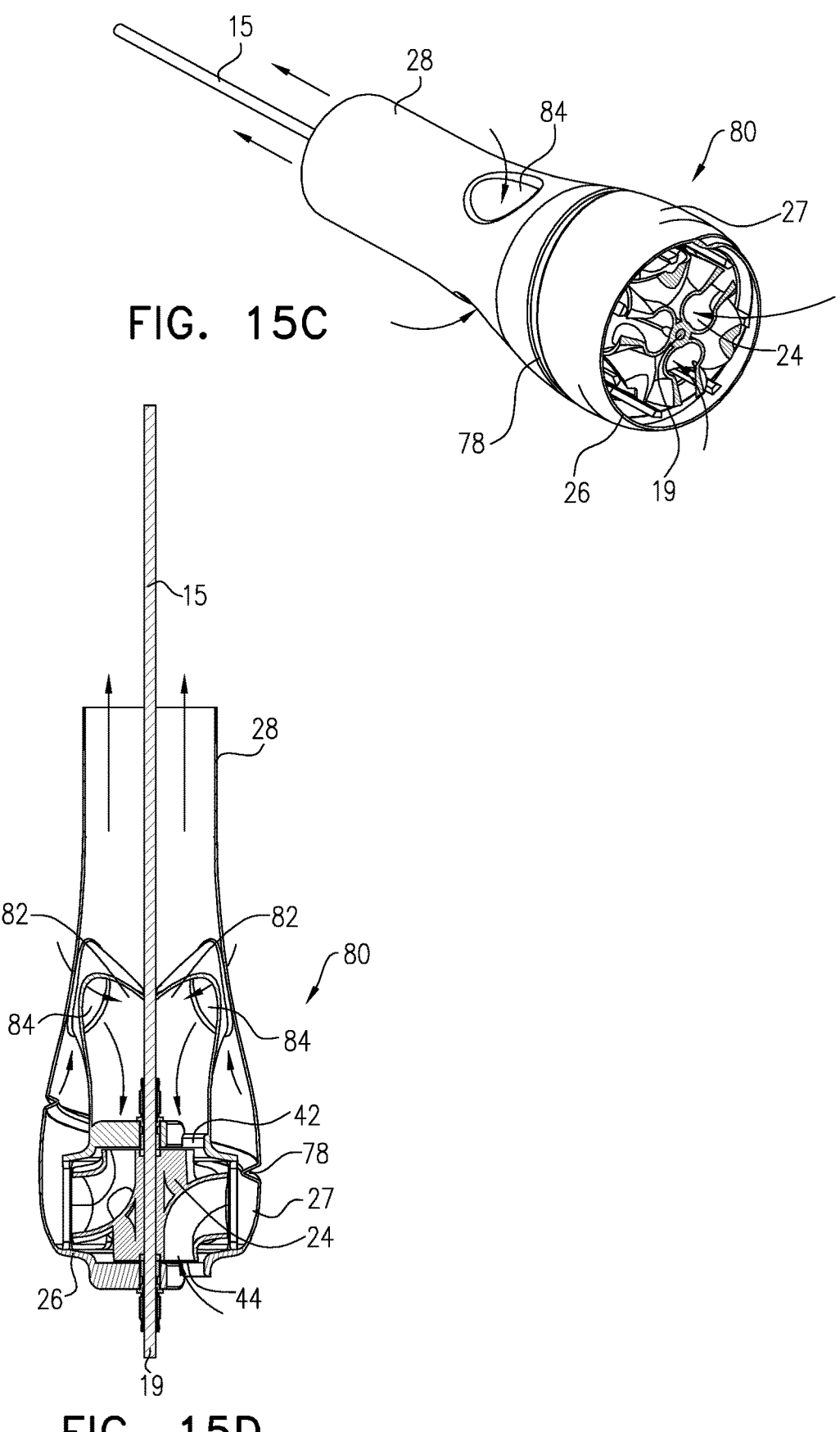
Figure 16A:
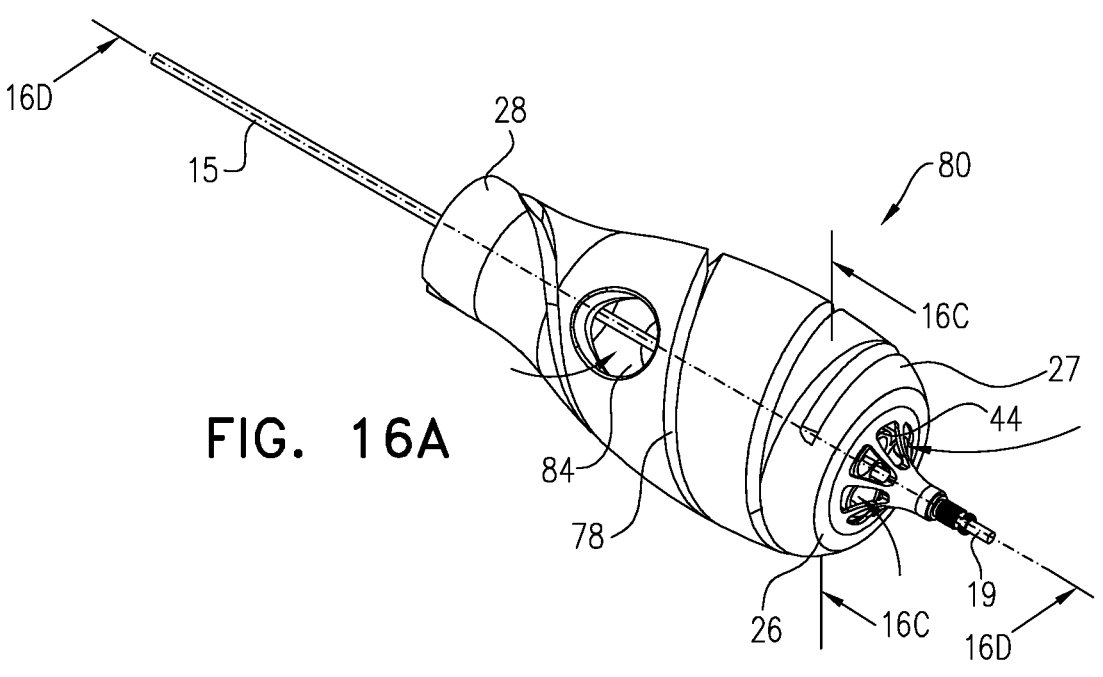
FIGS. 16A, 16B, 16C, and 16D are schematic illustrations of a pump-head portion of a ventricular assist device that includes one or more blood inlet tubes that pass through a volute and/or a pump-outlet tube, in accordance with some alternative applications of the present invention.
Figure 16B:
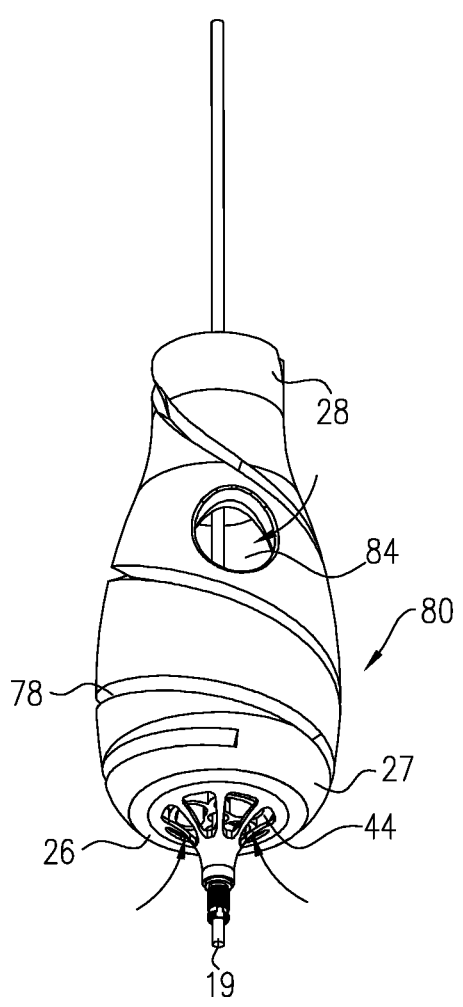
Figures 16C, 16D:
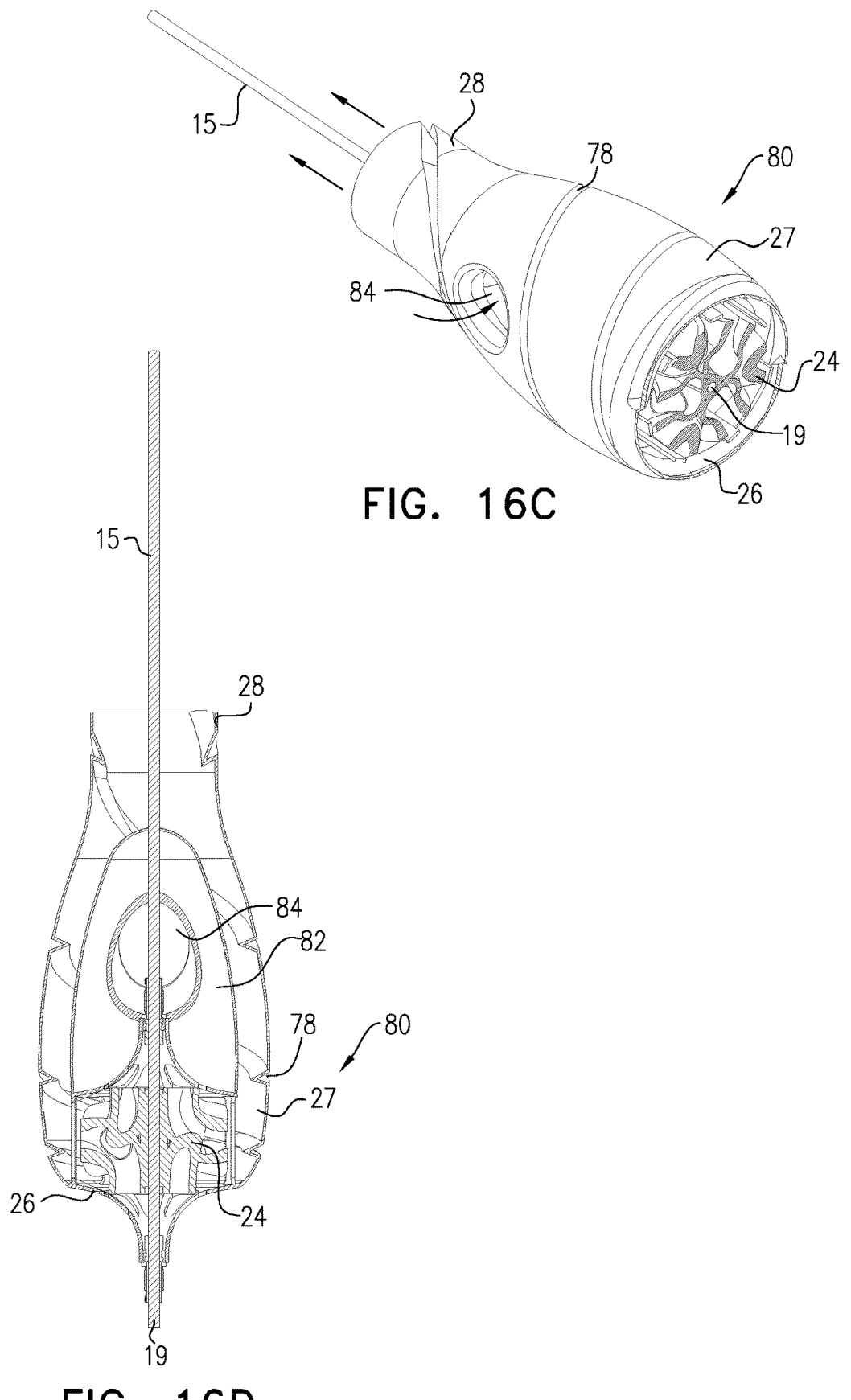

Reference is now made to FIGS. 12A, 12B, and 12C, which are schematic illustrations of centrifugally-pumping impeller 24 in a non-radially-constrained configuration, the impeller being a multi-layered biconical centrifugally-pumping impeller, in accordance with some applications of the present invention. The impeller shown in FIGS. 12A-C typically functions in a generally-similar manner to that described with reference to the impeller shown in FIGS. 11A-B, except for the differences described hereinbelow.

FIGS. 12A and 12B show, respectively, a 3D view and a cross-sectional view of an illustrative example of a multi-layered biconical centrifugally-pumping impeller that is made out of a solid material. In practice, impeller 24 is typically constructed from a frame 60 and a covering material 62, as described with reference to FIGS. 11A-B. Typically, each layer of the impeller is configured to pump blood from the ends of the impeller and radially outwardly from the center of the impeller, as is schematically illustrated in FIG. 12B. FIG. 12C is a schematic illustration of a slice of frame 60 of a multi-layered biconical centrifugally-pumping impeller. For some applications, a single tube of a shape-memory alloy (such as nitinol) is cut into struts and the struts are shaped such as to define each of the layers of the multi-layered biconical centrifugally-pumping impeller. For example, in the slice shown in FIG. 12C, strut 70 (in combination with additional struts that are not shown) defines an outer layer, strut 72 (in combination with additional struts that are not shown) defines an intermediate layer and strut 74 (in combination with additional struts that are not shown) defines an inner layer. Typically the covering material is applied to the struts that define each of the layers of the multi-layered biconical centrifugally-pumping impeller. For some applications, the struts extend from proximal bushing 64 to distal bushing 66, with the bushings typically being defined by the same tube from which the struts were cut, and with the bushings typically functioning as described hereinabove with reference to FIGS. 11A-B.

Reference is now made to FIGS. 13A-D, which are schematic illustrations of ventricular assist device 20, in accordance with some applications of the present invention. As described hereinabove, the ventricular assist device includes one or more centrifugally-pumping impellers 24 that are configured to be disposed within the subject's left ventricle. Each of the centrifugally-pumping impellers 24 is typically disposed inside an impeller housing 26. Typically, the impeller housing defines at least one blood inlet opening 42, 44 (via which blood flows into the impeller housing) and blood-outlet portion 46. Typically at least one volute 27 is disposed at least partially around the blood-outlet portion. Typically, the volute spirals and curves through 90 degrees and then leads into pump-outlet tube 28, which is disposed such that blood-outlet openings 30, defined by a proximal portion of the pump-outlet tube (shown in FIG. 1B), are disposed in the subject's aorta 32. Typically, by being shaped in the above-described shape, the volute gradually coverts radial flow to axial flow. As described hereinabove, typically, the pump-outlet tube and the volute are continuous with respect to each other. That is to say that, typically, the pump-outlet tube and the volute are made of the same material as each other, and the volute merges with the blood-outlet tube to form a continuous blood flow channel.

Typically, the centrifugally-pumping impellers are configured to assist the functioning of the left ventricle, by pumping blood from the left ventricle, through volute 27, into pump-outlet tube 28, and then out of blood-outlet openings 30 and into aorta 32. For some applications, each of the impeller housings includes a plurality of blood inlet openings, e.g., an upper blood-inlet opening 42 and a lower blood-inlet opening 44, as shown.

Reference is now made to FIGS. 14A-D, which are schematic illustrations of pump-head portion 80 of ventricular assist device 20, in accordance with some applications of the present invention. As described hereinabove, the ventricular assist device includes one or more centrifugally-pumping impellers 24 that are configured to be disposed within the subject's left ventricle. Each of the centrifugally-pumping impellers 24 is typically disposed inside an impeller housing 26. Typically, the impeller housing defines at least one blood inlet opening 42, 44 (via which blood flows into the impeller housing) and blood-outlet portion 46. For some applications, a plurality of volutes 27 are disposed at least partially around the blood-outlet portion, with the inlets to each of the volutes typically being spaced from each other around the circumference of the blood-outlet portion. Typically, each of the volutes spirals and curves through 90 degrees and then leads into pump-outlet tube 28, which is disposed such that blood-outlet openings 30, defined by a proximal portion of the tube (shown in FIG. 1B), are disposed in the subject's aorta 32. As described hereinabove, typically, the pump-outlet tube and the volutes are continuous with respect to each other. That is to say that, typically, the pump-outlet tube and the one or more volutes are made of the same material as each other, and the volutes merge with the blood-outlet tube to form a continuous blood flow channel.

Typically, the centrifugally-pumping impellers are configured to assist the functioning of the left ventricle, by pumping blood from the left ventricle, through volutes 27, into pump-outlet tube 28, and then out of blood-outlet openings 30 and into aorta 32. For some applications, each of the impeller housings includes a plurality of blood inlet openings, e.g., an upper blood-inlet opening 42 and a lower blood-inlet opening 44, as shown.

Reference is now made to FIGS. 15A-D, which are schematic illustrations of pump-head portion 80 of ventricular assist device 20, in accordance with some applications of the present invention. Reference is also made to FIGS. 16A-D, which are schematic illustrations of pump-head portion 80 of ventricular assist device 20, in accordance with some alternative applications of the present invention.

As described hereinabove, the ventricular assist device includes one or more centrifugally-pumping impellers 24 that are configured to be disposed within the subject's left ventricle. Each of the centrifugally-pumping impellers 24 is typically disposed inside an impeller housing 26. Typically, the impeller housing defines at least one blood inlet opening 42, 44 (via which blood flows into the impeller housing) and blood-outlet portion 46. For some applications, volute 27 is disposed at least partially around the blood-outlet portion and the volute spirals and curves through 90 degrees and then leads into pump-outlet tube 28, which is disposed such that blood-outlet openings 30, defined by a proximal portion of the pump-outlet tube (shown in FIG. 1B), are disposed in the subject's aorta 32. As described hereinabove, typically, the pump-outlet tube and the one or more volutes are continuous with respect to each other. That is to say that, typically, the pump-outlet tube and the one or more volutes are made of the same material as each other, and the volutes merge with the blood-outlet tube to form a continuous blood flow channel. For some applications, the continuous blood flow channel is shaped to define a fold 78, with the fold defining the spiraling and the curvature of the volute, and defining respective levels of the spiral of the volute, as shown in FIGS. 15A-D and 16A-D. Alternatively (not shown), a closed blood-flow channel defines the spiraling and the curvature of the volute, with the closed blood-flow channel forming respective levels of the volute, and with respective levels of the volute having one or more layers of material separating between them, rather than the fold defining the levels of the volute.

For some applications blood flow into the upper blood inlet opening is via one or more blood inlet tubes 82, which pass through volute 27 and/or pump-outlet tube 28. For example, as shown in FIGS. 15A-D and 16A-D, pump head portion 80 includes a plurality of blood inlet tubes 82, each of which defines a blood-inlet-tube opening 84, which is an opening through volute 27 and/or pump-outlet tube 28 that is fluid communication with the ventricular blood stream.

Blood flows into impeller housing 26 via blood-inlet-tube openings 84, through the blood-inlet tubes and into blood-inlet opening 42. For some applications, blood additionally flows into impeller housing 26 via lower blood-inlet opening 44. Blood typically flows out of the impeller housing via outlet portion 46 of the impeller housing, into volute 27 and then into pump-outlet tube 28. As described hereinabove, the blood typically then flows out of pump-outlet tube 28, via blood-outlet openings 30 (shown in FIG. 1B) and into aorta 32.

It is noted that in FIGS. 13A-16D, the proximal end of pump-outlet tube 28 (which defines blood-outlet openings) is not shown, for illustrative purposes.

Figure 17:
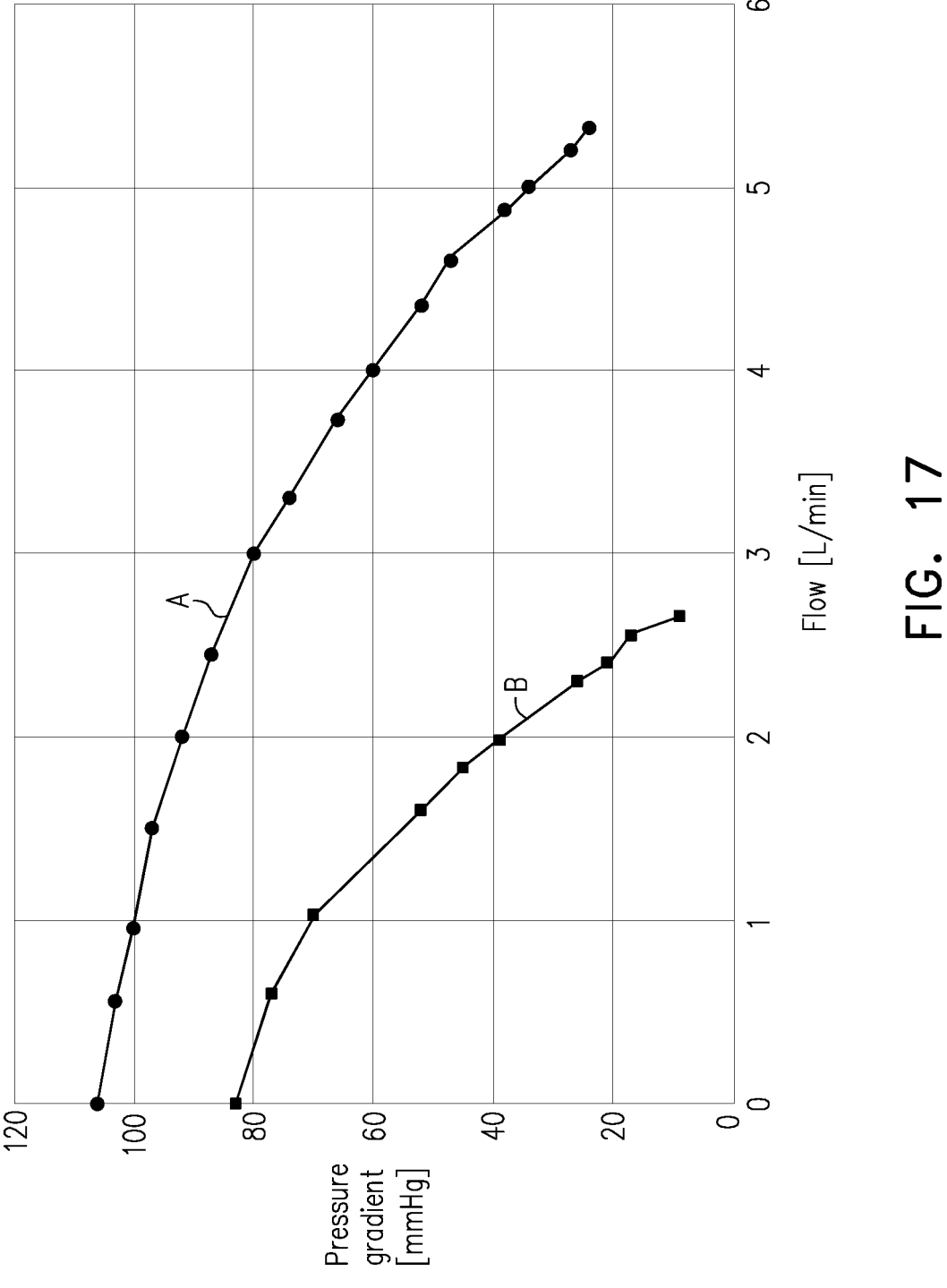
FIG. 17 is a graph showing pressure-flow curves for respective centrifugally-pumping impellers, in accordance with some applications of the present invention.

Reference is now made to FIG. 17, which is a graph showing pressure-flow curves for respective centrifugally-pumping impellers, in accordance with some applications of the present invention. Curve A is the pressure-flow curve for a first impeller having a height of 5 mm that is disposed inside an impeller housing having blood-inlet openings that are 8.4 mm in diameter, whereas curve B is the pressure-flow curve for a second impeller having a height of 2.5 mm and that is disposed inside an impeller housing having blood-inlet openings that are 5 mm in diameter. Both curves correspond to a rotation rate of 6,500 RPM. As may be observed, the flow generated by the second impeller is lower than that generated by the first impeller at all pressure gradients, and the flow generated by the second impeller drops to zero at a lower pressure gradient than that of the first impeller. Therefore, in accordance with some applications of the present invention, an impeller is used that has a minimum height of 4 mm (e.g., 5 mm). For some applications, the diameter of the blood-inlet opening (e.g., the upper blood-inlet opening, and/or the lower blood-inlet opening) of the impeller housing is more than 5 mm (e.g., more than 7 mm).

Figure 18:
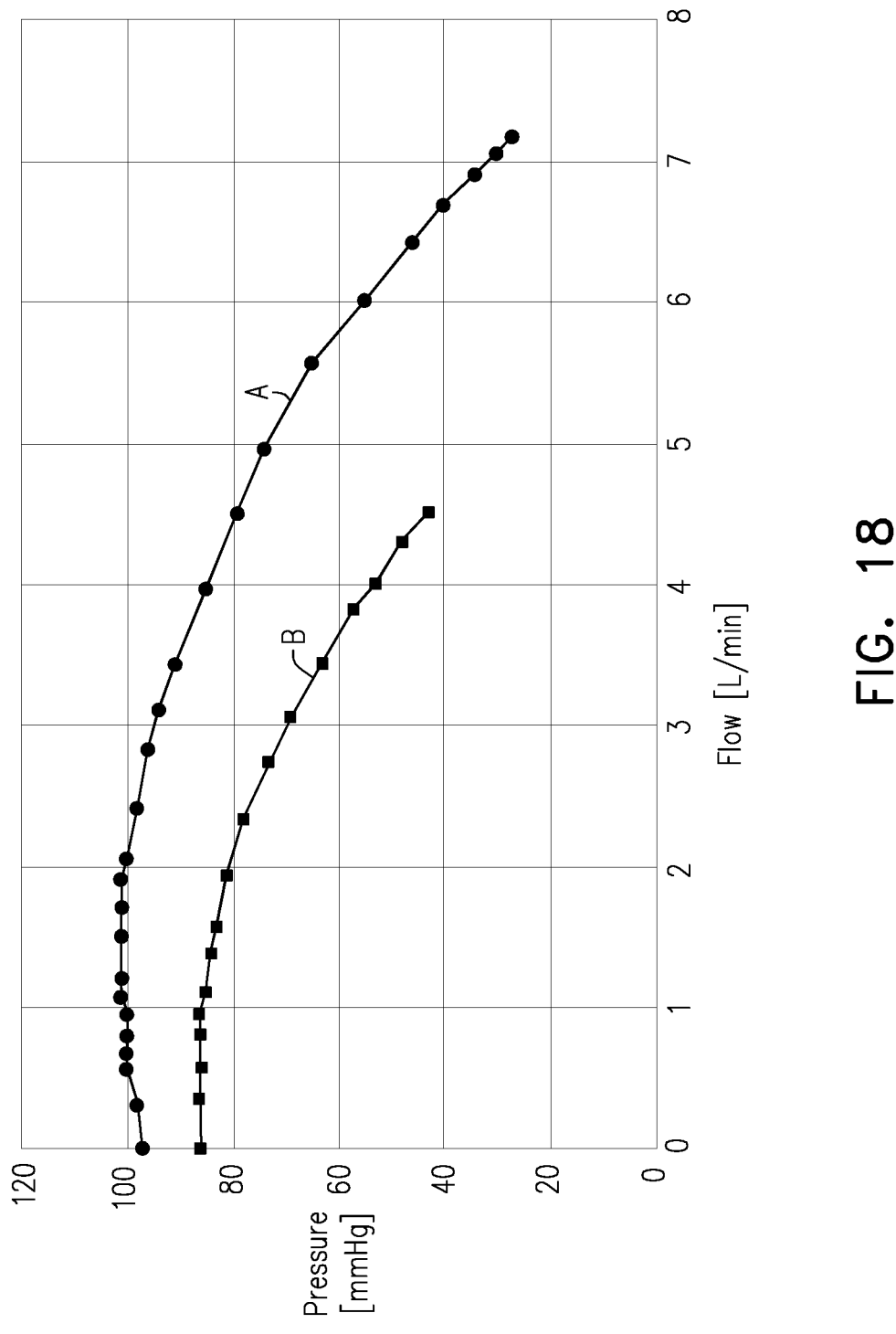
FIG. 18 is a graph showing pressure-flow curves for respective centrifugally-pumping impellers, in accordance with some applications of the present invention.

Reference is now made to FIG. 18, which is a graph showing pressure-flow curves for respective centrifugally-pumping impellers, in accordance with some applications of the present invention. Curve A is the pressure-flow curve for a forward-curved impeller (i.e., an impeller the blades of which curve circumferentially in the same direction as the direction in which the impeller is rotated), and curve B is for a generally similar impeller but one that is backward-curved (i.e., an impeller the blades of which curve circumferentially in the opposite direction from the direction in which the impeller is rotated). Both curves correspond to a rotation rate of 6,500 RPM. As may be observed, the flow generated by the second impeller is lower than that generated by the first impeller at all pressure gradients, and the flow generated by the second impeller drops to zero at a lower pressure gradient than that of the first impeller. Therefore, in accordance with some applications of the present invention, a forward-curved impeller is used.

Figure 19A:
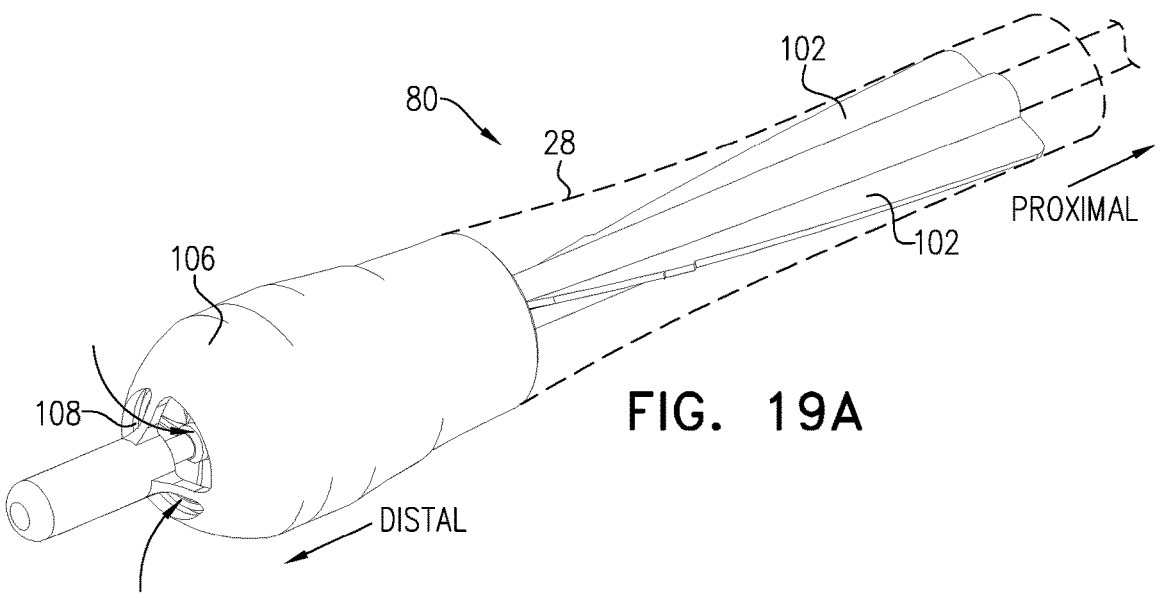
FIGS. 19A, 19B, and 19C are schematic illustrations of a pump-head portion of a ventricular assist device that includes a mixed-flow impeller, in accordance with some applications of the present invention.
Figure 19B:
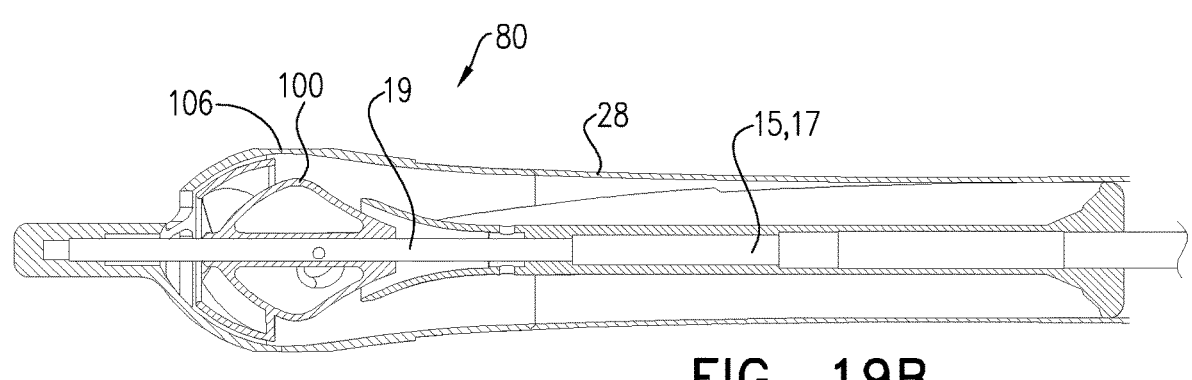
Figure 19C:
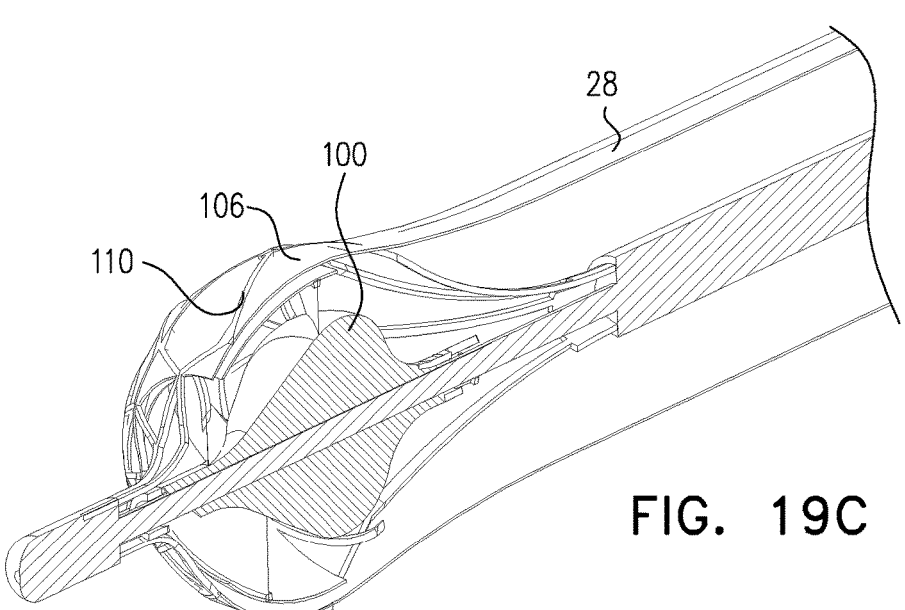

Reference is now made to FIGS. 19A, 19B, and 19C, which are schematic illustrations of pump-head portion 80 of a ventricular assist device 20 that includes a mixed-flow impeller 100, in accordance with some applications of the present invention. For some applications, a mixed-flow impeller that is configured to pump blood both axially and centrifugally is used within the ventricular assist device. For some applications, the mixed-flow impeller is disposed inside a frame 110, and pump-outlet tube 28 extends over the frame or within the frame such as to cover the portion of the frame within which the impeller is disposed. It is noted that in FIG. 19C, the pump-outlet tube is shown inside frame 110 for illustrative purposes, but typically, the pump outlet-tube is disposed outside of frame 110. For some applications (not shown), an additional inner lining lines at least a portion of frame 110, such that blood flow into the frame is exposed to a smooth inner surface.

Typically, the pump-outlet tube defines one or more blood inlet openings 108 via which blood is pumped into a distal end of pump-outlet tube 28 (which is configured to be placed within the ventricle). As described hereinabove, the blood typically then flows out of pump-outlet tube 28, via blood-outlet openings 30 (shown in FIG. 1B) and into aorta 32. It is noted that in FIGS. 19A-C, the proximal end of pump-outlet tube 28 (which defines blood-outlet openings) is not shown, for illustrative purposes. For some applications, a widened region 106 of the pump-outlet tube around the impeller is widened relative to a region proximal thereto. The impeller is configured to pump blood entering through blood inlet openings 108 both axially (in the proximal direction) and radially. The radial flow that is imparted to the blood causes the blood to flow into the widened region of the pump-outlet tube, and the blood is then redirected axially by the narrowing of the pump-outlet tube.

For some applications, spiral flow rectifiers 102 are disposed within pump-outlet tube 28 proximally with respect to impeller 100. The spiral flow rectifiers are configured to reduce radial and/or rotational flow components from the blood flow by converting these components to axial flow prior to the blood flowing out of the proximal end of the pump-outlet tube. For some applications, the flow rectifiers have spiral shapes with a pitch of the spiral increasing from the distal ends of the flow rectifiers to their proximal ends. By being shaped in this way, the flow rectifiers gradually covert radial flow to axial flow. For some applications, the flow rectifiers extend radially from a tube within which the drive cable is disposed (e.g., tube 17) to pump-outlet tube. In accordance with respective applications, the flow rectifiers are made of a flexible material (e.g., an elastomeric material, silicone, polyurethane, polyester, polyethylene terephthalate (PET), and/or polyether block amide (e.g., PEBAX®)), or comprise a structure that is made of a shape memory alloy (such as nitinol) that is covered with a flexible material (e.g., an elastomeric material, silicone, polyurethane, polyester, polyethylene terephthalate (PET), and/or polyether block amide (e.g., PEBAX®)).

Reference is now made to FIGS. 20Ai and 20Aii, which are schematic illustrations of respective views of impeller 100, in accordance with some applications of the present invention. FIG. 20Ai shows the impeller disposed on axial shaft 19, in the absence of any surrounding portions of pump-head portion 80, for illustrative purposes. FIGS. 20Aii shows a cross-sectional view of the impeller disposed within frame 110, but in the absence of pump-outlet tube 28, again for illustrative purposes. For some applications, the impeller has a generally similar structure to that described in US 2020/0237981 to Tuval, which is incorporated herein by reference. Typically, the impeller includes a plurality of outer elongate elements 101, which are helical and which wind around a central axial spring 103, such that the helices defined by the helical elongate elements are coaxial with the central axial spring. Typically, the impeller includes two or more helical elongate elements (e.g., three helical elongate elements). For some applications, the helical elongate elements and the central axial spring are made of a shape-memory material, e.g., a shape-memory alloy such as nitinol. Typically, each of the helical elongate elements and the central axial spring support a film 105 of a material (e.g., an elastomer, such as polyurethane, and/or silicone) therebetween. For some applications, the film of material includes pieces of nitinol embedded therein, for example in order to strengthen the film of material.

As shown in FIGS. 20Ai-ii, for some applications, the shapes of the helical elongate elements are axially symmetrical, i.e., the shapes of the helical elongate elements at their proximal ends is the same as that of their distal ends. Typically, when deployed within a pump head that is as shown in FIGS. 21Bi-Bii, such an impeller is configured to pump blood both axially and radially, as described in further detail hereinbelow.

Reference is now made to FIGS. 20Bi and 20Bii, which are schematic illustrations of respective views of impeller 100, in accordance with some applications of the present invention. FIG. 20Bi shows the impeller disposed on axial shaft 19, in the absence of any surrounding portions of pump-head portion 80, for illustrative purposes. FIGS. 20Bii shows a cross-sectional view of the impeller disposed within frame 110, but in the absence of pump-outlet tube 28, again for illustrative purposes. For some applications, the impeller has a generally similar structure to that described in US 2020/0237981 to Tuval, which is incorporated herein by reference, except for differences described hereinbelow. Typically, the impeller includes a plurality of outer elongate elements 101, which wind around a central axial spring 103. For some applications, toward a distal end of the impeller, the elongate elements are helical, such that the helices defined by the helical elongate elements are coaxial with the central axial spring. As the elongate elements transition toward the proximal end of the impeller, the elongate elements transition to defining a paddle shape that extends radially from the central axial spring. Typically, the impeller includes two or more elongate elements (e.g., three elongate elements). For some applications, the elongate elements and the central axial spring are made of a shape-memory material, e.g., a shape-memory alloy such as nitinol. Typically, each of the elongate elements and the central axial spring support a film 105 of a material (e.g., an elastomer, such as polyurethane, and/or silicone) therebetween. For some applications, the film of material includes pieces of nitinol embedded therein, for example in order to strengthen the film of material.

Typically, by virtue of the change in the shapes of the elongate elements, the impeller blades transition from being spiral shaped within a distal portion of the impeller to being substantially radially-extending and paddle shaped within a proximal portion of the impeller. The distal portion of the impeller (by virtue of its shape) is configured primarily to impart axial flow to blood that it pumps, whereas the proximal portion of the impeller is configured to impart substantial radial flow to blood that it pumps. For some applications, this increases the flow and/or pressure that impeller is able to add to blood that it pumps (relative to an impeller that is shaped as shown in FIGS. 20Ai-Aii, for example) because as blood flows from the distal end of the impeller to the proximal end of the impeller the impeller continues to impart additional flow and/or pressure to the blood.

Reference is now made to FIGS. 20Ci and 20Cii, which are schematic illustrations of respective views of impeller 100, in accordance with some applications of the present invention. FIG. 20Ci shows the impeller disposed on axial shaft 19, in the absence of any surrounding portions of pump-head portion 80, for illustrative purposes. FIGS. 20Cii shows a cross-sectional view of the impeller disposed within frame 110, but in the absence of pump-outlet tube 28, again for illustrative purposes. For some applications, the impeller has a generally similar structure to that described with reference to FIGS. 20Bi-Bii, but the impeller includes an expandable portion 116 disposed between the central axial spring 103 and elongate elements 101. Alternatively, the impeller has a different configuration but has expandable portion 116 disposed along its axis. In its expanded configuration, the expandable portion is typically shaped such that its diameter increases from the distal end of the expandable portion to the proximal end of the expandable portion. For example, the expandable portion may have a conical shape, a frustoconical shape, or a three-dimensional teardrop shape (i.e., with a semispherical distal end, and a conical or frustoconical proximal end). For some applications, the expandable portion is self-expandable. For example, the expandable portion may be made of a shape-memory alloy (e.g., nitinol) that is covered with a material (e.g., an elastomeric material, and/or a flexible plastic material). Alternatively or additionally, the expandable portion is inflatable.

As described hereinabove, for some applications, the apparatus includes a purging system 16 and a plurality of purging fluid ports 18 (e.g., purging fluid inlet ports, and/or purging fluid outlet ports), via which a purging fluid (e.g., a glucose-based solution and/or saline) is pumped into the ventricular assist device, in order to purge portions of the ventricular assist device. Typically, the purging fluid is configured to be pumped into the apparatus such that the purging fluid flows between drive cable 15 and outer tube 17, and thereby purges the interface between the drive cable and the outer tube. Further typically, the purging fluid is configured to purge interfaces between axial shaft 19 and radial bearings within which the axial shaft rotates. For some applications, expandable portion 116 of impeller 100 is configured to be inflated by the purging fluid. Typically, in such applications, in order to control the inflation of the expandable portion of the impeller, the pressure at which the purging fluid is pumped into the ventricular assist device is modulated.

Typically, by virtue of the shape of the expandable portion of the impeller, the impeller is configured to impart additional radial flow to the blood as it flows from the distal end to the proximal end of the impeller. For some applications, this increases the flow and/or pressure that impeller is able to add to blood that it pumps (relative to an impeller that is shaped as shown in FIGS. 20Ai-Aii, for example) because as blood flows from the distal end of the impeller to the proximal end of the impeller the impeller imparts additional flow and/or pressure to the blood.

Figure 21A:
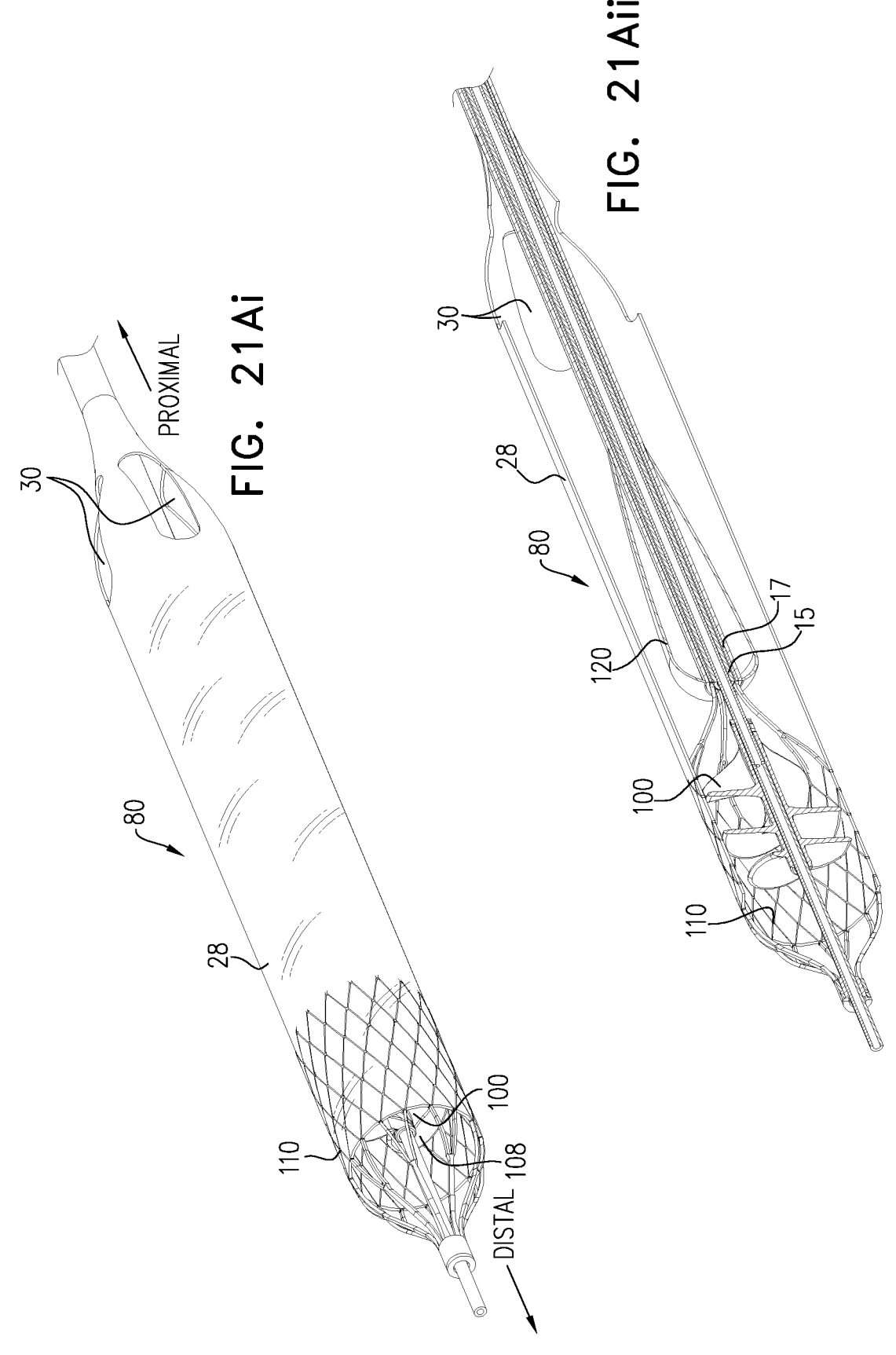
FIGS. 21Ai and 21Aii are schematic illustrations of respective views of a pump-head portion of a ventricular assist device that includes an expandable flow rectifier, in accordance with some applications of the present invention.
Figure 21B:
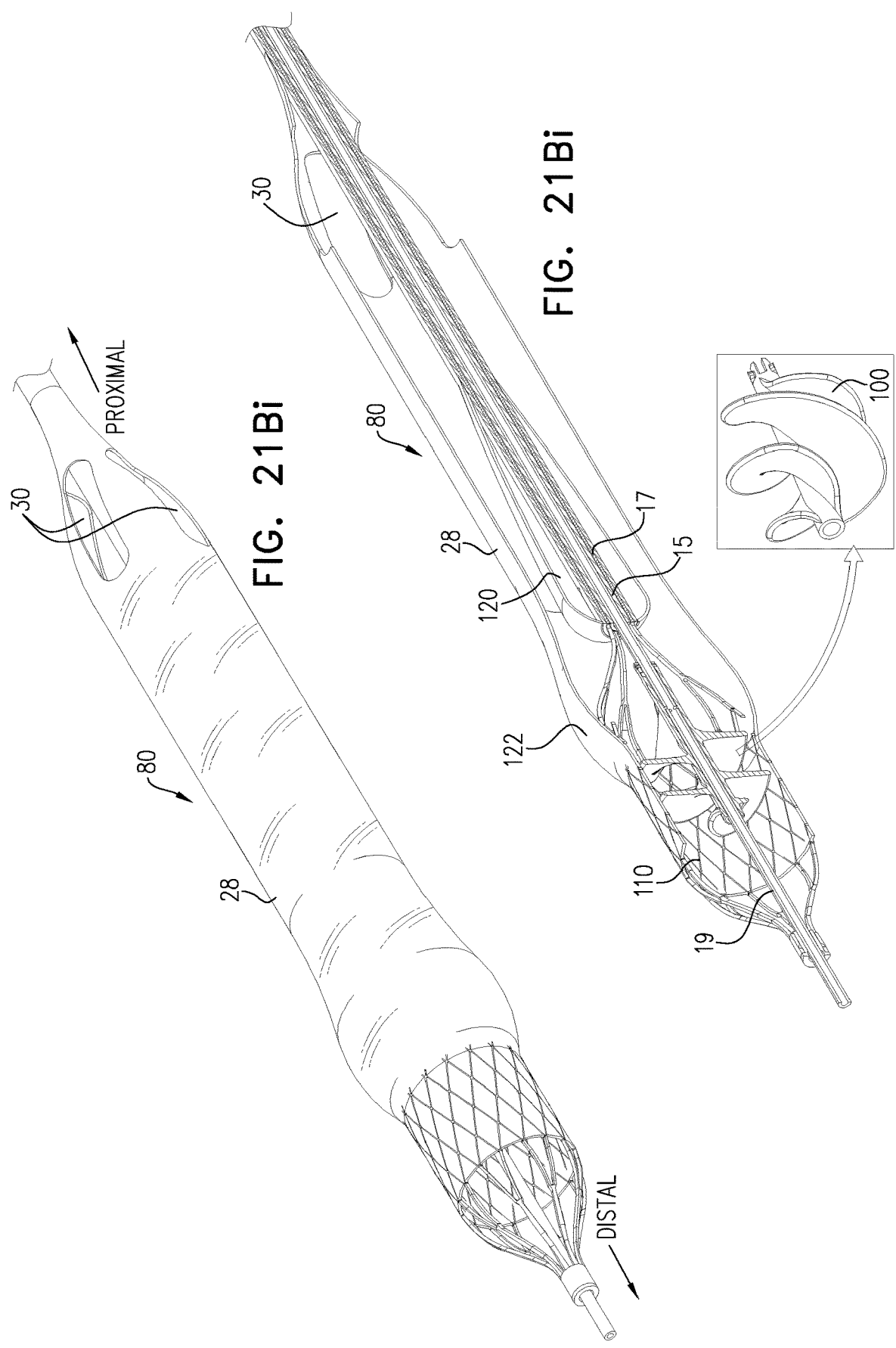
FIGS. 21Bi and 21Bii are schematic illustrations of respective views of a pump-head portion of a ventricular assist device that includes an expandable flow rectifier, in accordance with some alternative applications of the present invention.

Reference is now made to FIGS. 21Ai and 21Aii, which are schematic illustrations of respective views of pump-head portion 80 of ventricular assist device 20, the pump-head portion including an expandable flow rectifier 120, in accordance with some applications of the present invention. For some applications, the general configuration of the pump-head portion is similar to that described in US 2020/0237981 to Tuval, which is incorporated herein by reference, except for differences described hereinbelow. As shown, the impeller is disposed inside frame 110, within a distal portion of pump-outlet tube 28. The distal end of pump-outlet tube defines an axially-facing blood-inlet opening 108, via which blood flow into the pump-outlet tube. In the example shown in FIGS. 21Ai-Aii, the impeller has a configuration as shown and described with reference to FIGS. 20Bi-Bii. As described hereinabove, in addition to imparting axial flow to the blood, the impeller imparts radial flow to the blood. Typically, the flow rectifier is configured to reduce radial and/or rotational components of the blood flow by converting these components to axial flow prior to the blood flowing out of blood-outlet openings 30 at the proximal end of the pump-outlet tube, and into the aorta.

Typically, expandable flow rectifier is disposed along the axis of pump-outlet tube 28. For some applications, the expandable flow rectifier extends radially from around the drive cable (e.g., from around outer tube 17, which surround the drive cable, or from outside an additional outer tube disposed around the drive cable). Typically, in its expanded configuration, the expandable flow rectifier is shaped such that its diameter decreases from its distal end to its proximal end. For example, the expandable flow rectifier may have a conical shape, a frustoconical shape, or a three-dimensional teardrop shape (i.e., with a semispherical distal end, and a conical or frustoconical proximal end). For some applications, the expandable flow rectifier is self-expandable. For example, the expandable flow rectifier may be made of a shape-memory alloy (e.g., nitinol) that is covered with a material (e.g., an elastomeric material, silicone, polyurethane, polyester, polyethylene terephthalate (PET), and/or polyether block amide (e.g., PEBAX®)). Alternatively or additionally, the expandable flow rectifier is inflatable.

As described hereinabove, for some applications, the apparatus includes a purging system 16 and a plurality of purging fluid ports 18 (e.g., purging fluid inlet ports, and/or purging fluid outlet ports), via which a purging fluid (e.g., a glucose-based solution and/or saline) is pumped into the ventricular assist device, in order to purge portions of the ventricular assist device. Typically, the purging fluid is configured to be pumped into the apparatus such that the purging fluid flows between drive cable 15 and outer tube 17, and thereby purges the interface between the drive cable and the outer tube. Further typically, the purging fluid is configured to purge interfaces between axial shaft 19 and radial bearings within which the axial shaft rotates. For some applications, expandable flow rectifier 120 is configured to be inflated by the purging fluid. Typically, in such applications, in order to control the inflation of the expandable flow rectifier, the pressure at which the purging fluid is pumped into the ventricular assist device by the purging system is modulated.

Reference is now made to FIGS. 21Bi and 21Bii, which are schematic illustrations of respective views of pump-head portion 80 of ventricular assist device 20, the pump-head portion including expandable flow rectifier 120, and pump-outlet tube 28 including a widened region 122 in the vicinity of impeller 100, in accordance with some applications of the present invention. As shown in FIGS. 21Bi-21Bii, for some applications, pump-outlet tube 28 includes widened region 122 in the vicinity of impeller 100 (e.g., immediately proximally to, and/or surrounding, the impeller), which is wider than a portion of the pump-outlet tube proximal thereto. The impeller is configured to pump blood entering through blood inlet opening 108 both axially (in the proximal direction) and centrifugally. The centrifugal flow that is imparted to the blood causes the blood to flow into the widened region of the pump-outlet tube, and the blood is then redirected axially by the narrowing of the pump-outlet tube. In the example shown in FIGS. 21Bi-Bii, the impeller is configured as shown in FIGS. 20Ai-Aii. Typically, when deployed within a pump-outlet tube that has a widened portion as shown in FIGS. 21Bi-Bii, such an impeller is configured impeller to pump blood both axially and centrifugally. As shown in FIGS. 21Bi-Bii, for some applications, pump-head portion 80 includes expandable flow rectifier 120, which is generally as described hereinabove with reference to FIGS. 21Ai-Aii.

Figure 21C:
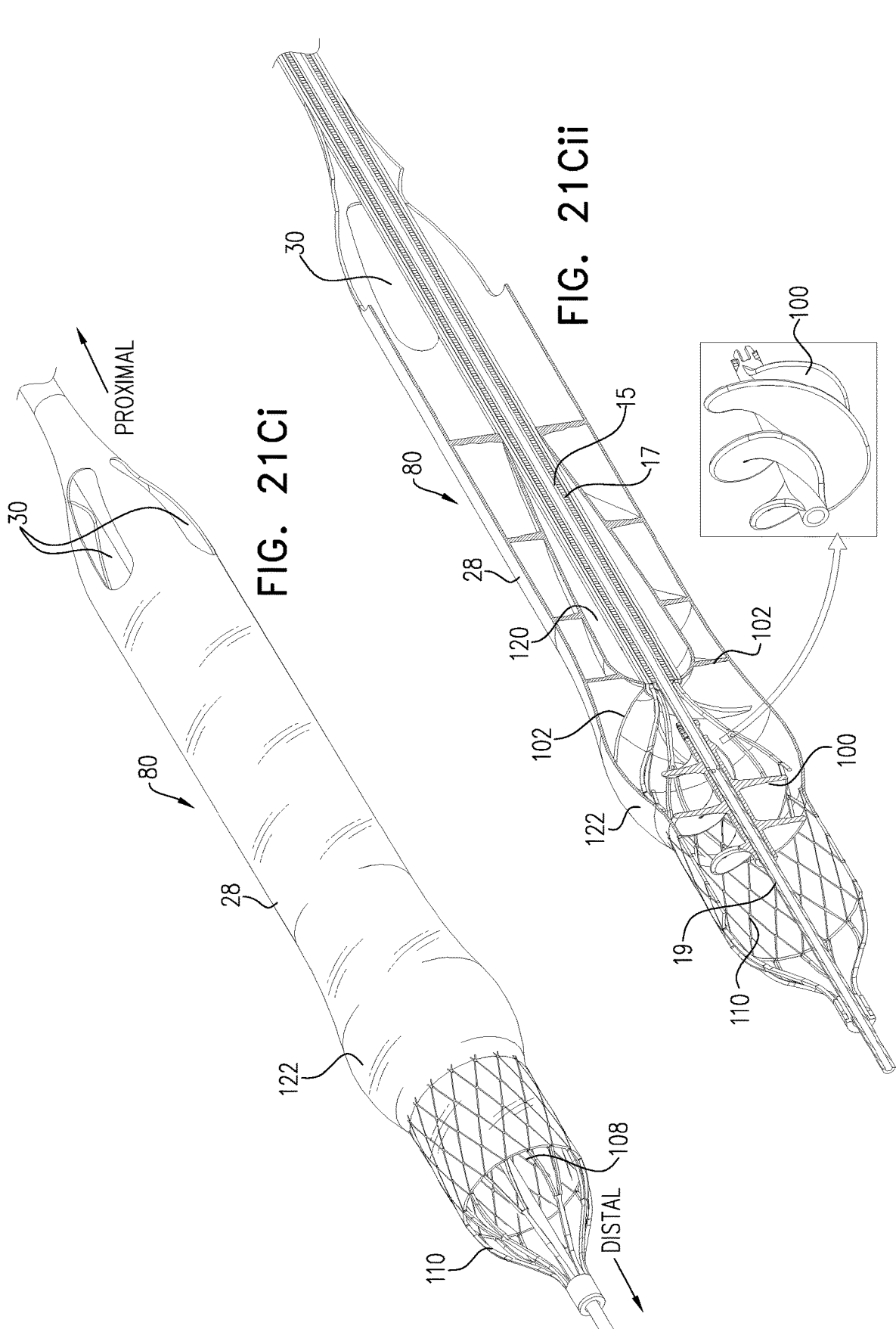
FIGS. 21Ci and 21Cii are schematic illustrations of respective views of a pump-head portion of a ventricular assist device that includes an expandable flow rectifier, in accordance with some further alternative applications of the present invention.
Figure 21D:
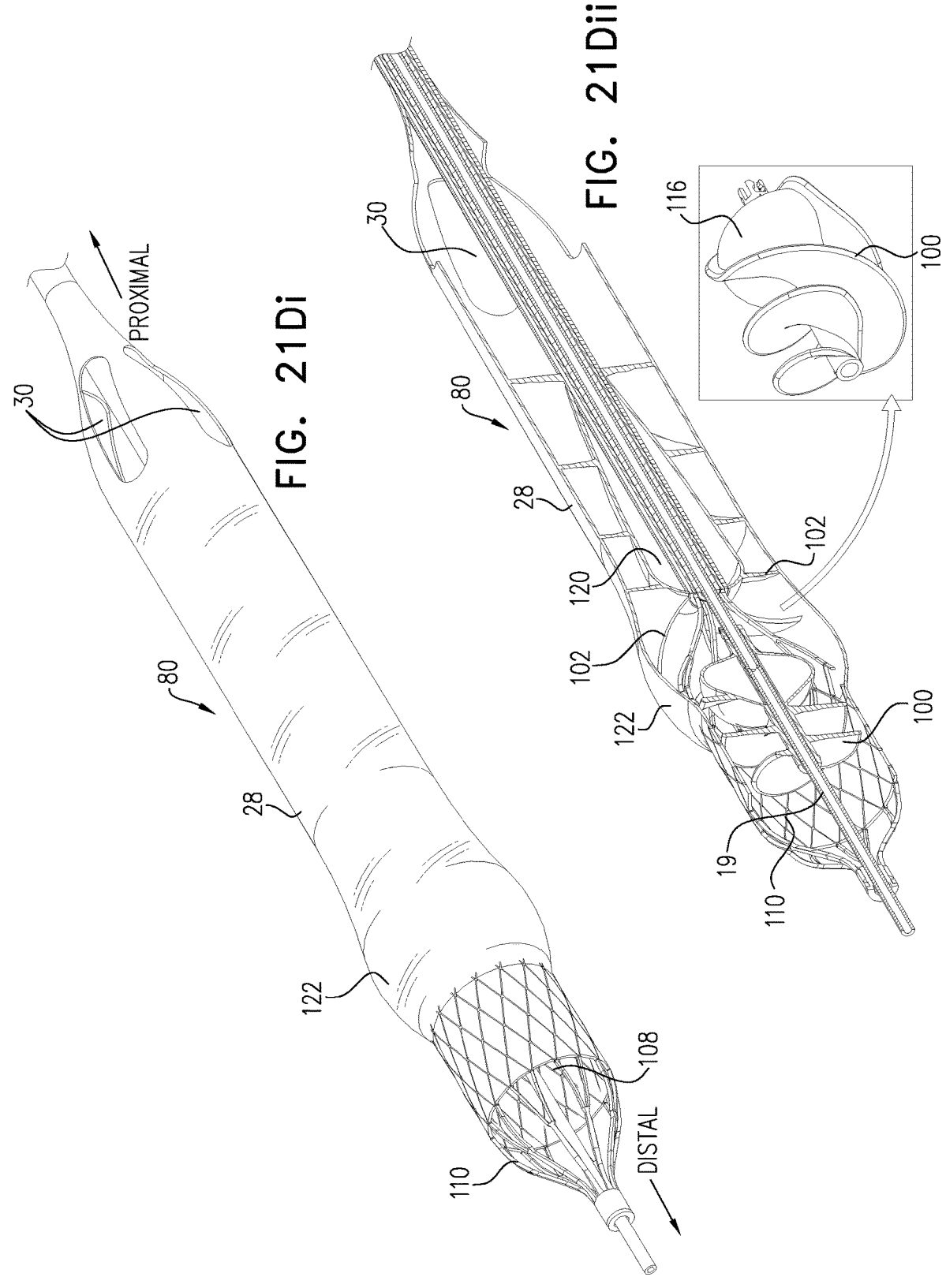
FIGS. 21Di and 21Dii are schematic illustrations of respective views of a pump-head portion of a ventricular assist device that includes an expandable flow rectifier, in accordance with some further alternative applications of the present invention.

Reference is now made to FIGS. 21Ci and 21Cii as well as FIGS. 21Di and 21Dii, which are schematic illustrations of respective views of pump-head portion 80 of ventricular assist device 20, the pump-head portion including expandable flow rectifier 120, and pump-outlet tube 28 including a widened region 122 in the vicinity of impeller 100, in accordance with some alternative applications of the present invention. Pump-head portion 80 as shown in FIGS. 21Ci-Dii is generally as shown and described with reference to FIGS. 21Bi-Bii. However, in addition to expandable flow rectifier 120, spiral flow rectifiers 102 are disposed within pump-outlet tube proximally with respect to impeller, spiral flow rectifiers 102 extending radially from the expandable flow rectifier to the pump-outlet tube. The spiral flow rectifiers are configured to reduce rotational flow components from the blood flow prior to the blood flowing out of the pump-outlet tube. For some applications, the flow rectifiers have spiral shapes with a pitch of the spiral increasing from the distal ends of the flow rectifiers to their proximal ends. By being shaped in this way, the flow rectifiers gradually covert radial flow to axial flow. In accordance with respective applications, the flow rectifiers are made of a flexible material (e.g., an elastomeric material, silicone, polyurethane, polyester, polyethylene terephthalate (PET), and/or polyether block amide (e.g., PEBAX®)), or comprise a structure that is made of a shape memory alloy (such as nitinol) that is covered with a flexible material (e.g., an elastomeric material, silicone, polyurethane, polyester, polyethylene terephthalate (PET), and/or polyether block amide (e.g., PEBAX®)).

As shown in FIGS. 21Ci-Cii, for some applications, a pump-head portion 80 that is configured as described in the above paragraph is used with an impeller as is generally described in FIGS. 20Ai-Aii. Alternatively, as shown in FIGS. 21Di-Dii, a pump-head portion 80 that is configured as described in the above paragraph is used with an impeller as is generally described in FIGS. 20Ci-Cii. Further alternatively (not shown), a pump-head portion 80 that is configured as described in the above paragraph is used with an impeller as is generally described in FIGS. 20Bi-Bii, or any other type of impeller. In general it is noted that the scope of the present application includes combining any of the components of any of the impellers described with reference to FIGS. 20Ai-20Cii and any component of any of the pump-head portions described with reference to FIGS. 21Ai-21Dii with each other. For example, any one of the impellers described herein may be combined with a pump-outlet tube having widened region 122 in the vicinity of the impeller, expandable flow rectifier 120, and/or spiral flow rectifiers 102.

Figure 22A:
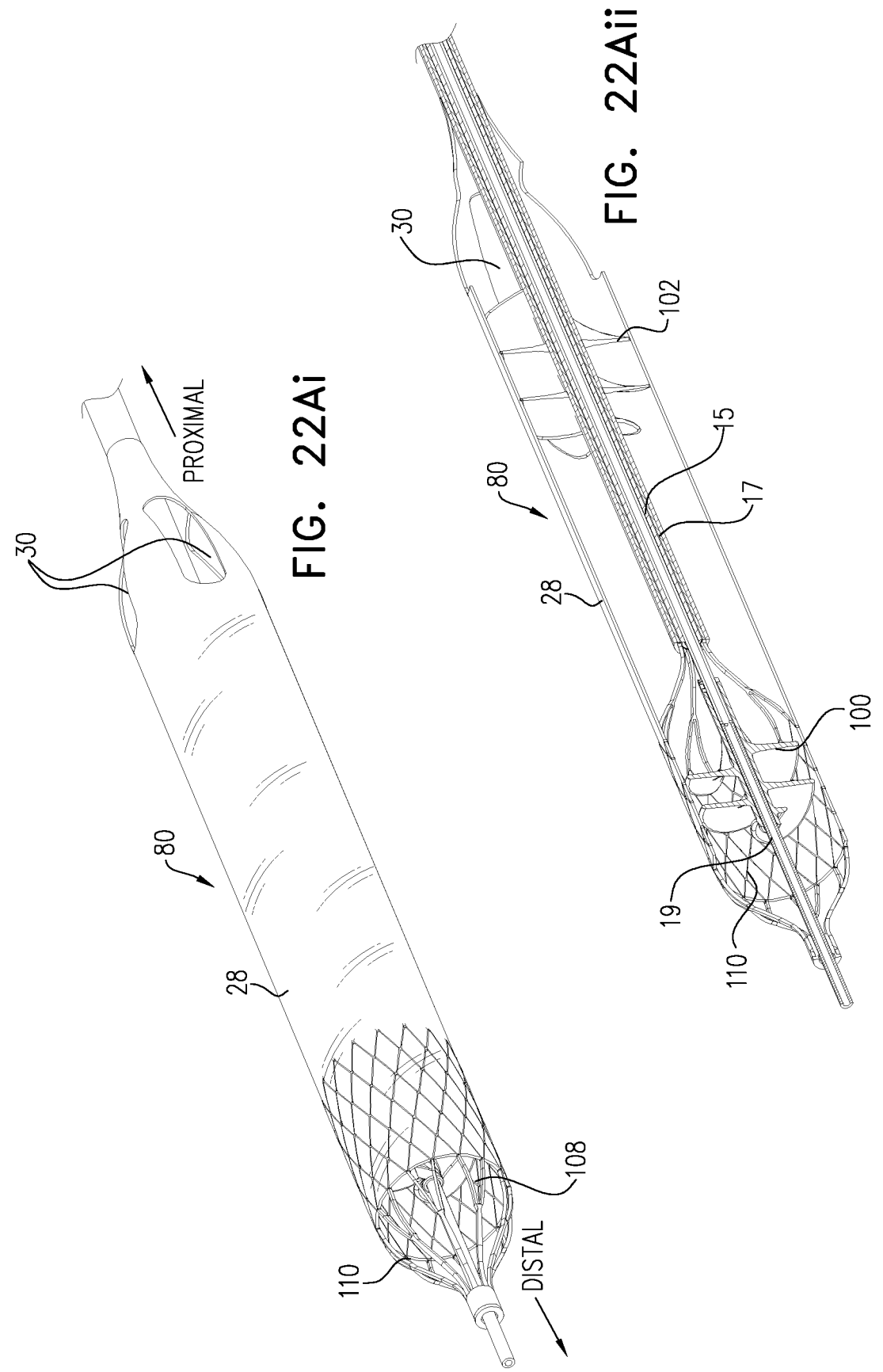
FIGS. 22Ai and 22Aii are schematic illustrations of respective views of a pump-head portion of a ventricular assist device that includes spiral flow rectifiers, in accordance with some applications of the present invention.
Figure 22B:
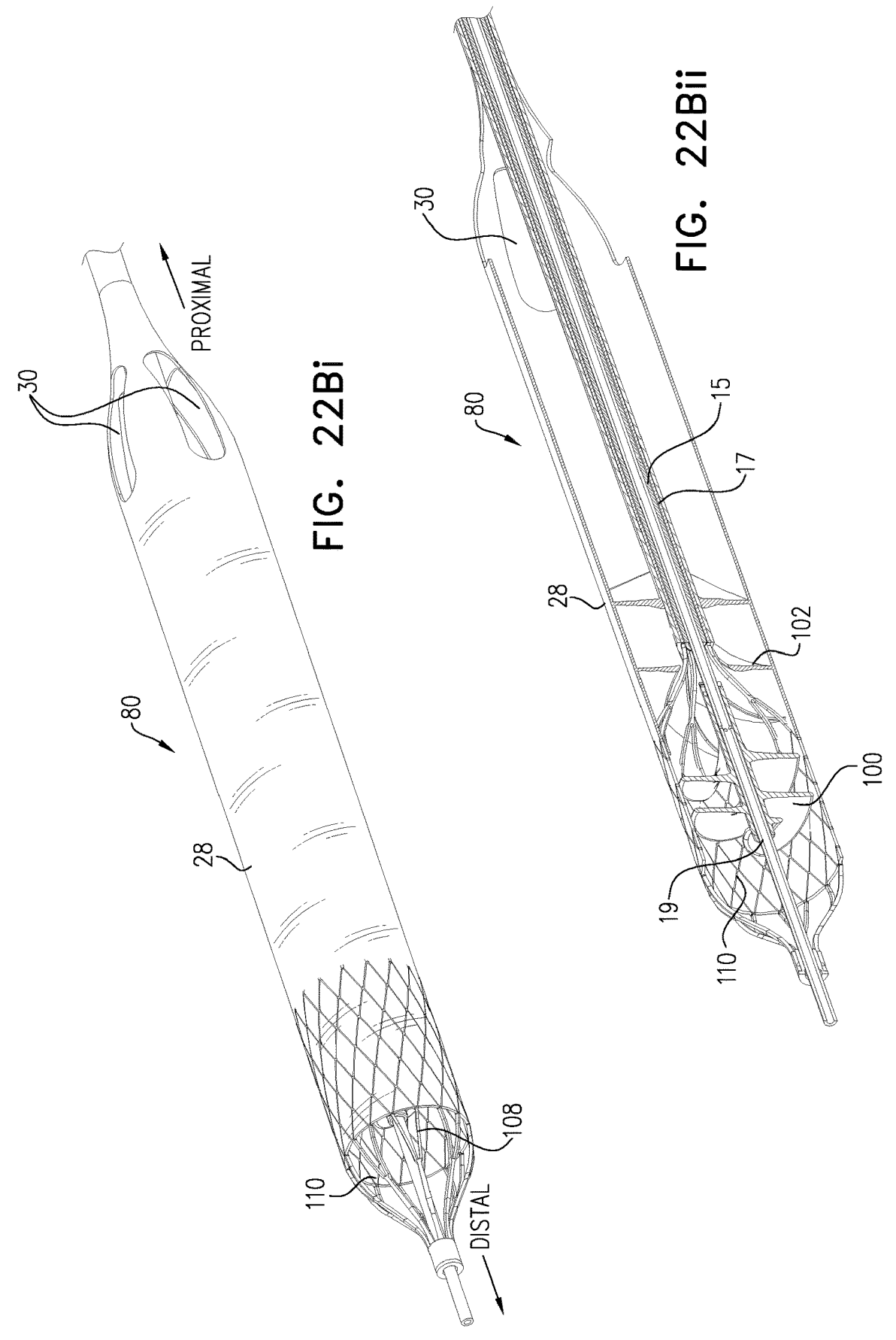
FIGS. 22Bi and 22Bii are schematic illustrations of respective views of a pump-head portion of a ventricular assist device that includes spiral flow rectifiers, in accordance with some applications of the present invention.

Reference is now made to FIGS. 22Ai and 22Aii and to FIGS. 22Bi and 22Bii, which are schematic illustrations of respective views of pump-head portion 80 of ventricular assist device, in accordance with some applications of the present invention. As shown in FIGS. 22Ai-Aii, for some applications, spiral flow rectifiers 102 are disposed within a portion of pump-outlet tube that is immediately distal to blood-outlet openings 30. Alternatively or additionally, for some applications spiral flow rectifiers 102 are disposed within a portion of pump-outlet tube that is immediately proximal to impeller 100, as shown in FIGS. 22Bi-Bii. The spiral flow rectifiers are generally as described hereinabove.

It is noted that in FIGS. 21Ai, 21Bi, 21Ci, 21Di, 22Ai, and 22Bi, the pump-outlet tube is shown inside frame 110 for illustrative purposes, but typically, the pump outlet-tube is disposed outside of frame 110. For some applications (not shown), an additional inner lining lines at least a portion of frame 110, such that blood flow into the frame is exposed to a smooth inner surface.

With regards to all aspects of ventricular assist device 20 described with reference to FIGS. 1A-22Bii, it is noted that, although FIG. 1B show ventricular assist device 20 in the subject's left ventricle, for some applications, device 20 is placed inside the subject's right ventricle, such that the device traverses the subject's pulmonary valve, and techniques described herein are applied, mutatis mutandis. For some applications, components of device 20 are applicable to different types of blood pumps. For example, aspects of the present invention may be applicable to a pump that is used to pump blood from the vena cava and/or the right atrium into the right ventricle, from the vena cava and/or the right atrium into the pulmonary artery, and/or from the renal veins into the vena cava. For example, any one of the impeller configurations, and/or any configuration of volutes, pump-outlet tubes, and/or flow rectifiers described herein, may be used in conjunction with any of the aforementioned pumps, mutatis mutandis.

The scope of the present invention includes combining any of the apparatus and methods described herein with any of the apparatus and methods described in one or more of the following applications, all of which are incorporated herein by reference:

US 2020/0237981 to Tuval, entitled "Distal tip element for a ventricular assist device," filed Jan. 23, 2020, which claims priority from:

U.S. Provisional Patent Application 62/796,138 to Tuval, entitled "Ventricular assist device," filed Jan. 24, 2019;

U.S. Provisional Patent Application 62/851,716 to Tuval, entitled "Ventricular assist device," filed May 23, 2019;

U.S. Provisional Patent Application 62/870,821 to Tuval, entitled "Ventricular assist device," filed Jul. 5, 2019; and U.S. Provisional Patent Application 62/896,026 to Tuval, entitled "Ventricular assist device," filed Sep. 5, 2019.

US 2019/0209758 to Tuval, which is a continuation of International Application No. PCT/IB2019/050186 to Tuval (published as WO 19/138350), entitled "Ventricular assist device," filed Jan. 10, 2019, which claims priority from:

U.S. Provisional Patent Application 62/615,538 to Sohn, entitled "Ventricular assist device," filed Jan. 10, 2018;

U.S. Provisional Patent Application 62/665,718 to Sohn, entitled "Ventricular assist device," filed May 2, 2018;

U.S. Provisional Patent Application 62/681,868 to Tuval, entitled "Ventricular assist device," filed Jun. 7, 2018; and U.S. Provisional Patent Application 62/727,605 to Tuval, entitled "Ventricular assist device," filed Sep. 6, 2018;

US 2019/0269840 to Tuval, which is the US national phase of International Patent Application PCT/IL2017/051273 to Tuval (published as WO 18/096531), filed Nov. 21, 2017, entitled "Blood pumps," which claims priority from U.S. Provisional Patent Application 62/425,814 to Tuval, filed Nov. 23, 2016;

US 2019/0175806 to Tuval, which is a continuation of International Application No. PCT/IL2017/051158 to Tuval (published as WO 18/078615), entitled "Ventricular assist device," filed Oct. 23, 2017, which claims priority from U.S. 62/412,631 to Tuval filed Oct. 25, 2016, and U.S. 62/543,540 to Tuval, filed Aug. 10, 2017;

US 2019/0239998 to Tuval, which is the US national phase of International Patent Application PCT/IL2017/051092 to Tuval (published as WO 18/061002), filed Sep. 28, 2017, entitled "Blood vessel tube," which claims priority from U.S. Provisional Patent Application 62/401,403 to Tuval, filed Sep. 29, 2016;

US 2018/0169313 to Schwammenthal, which is the US national phase of International Patent Application PCT/IL2016/050525 to Schwammenthal (published as WO 16/185473), filed May 18, 2016, entitled "Blood pump," which claims priority from U.S. Provisional Patent Application 62/162,881 to Schwammenthal, filed May 18, 2015, entitled "Blood pump;"

U.S. Pat. No. 10,583,231 to Schwammenthal, which is the US national phase of International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

U.S. Pat. No. 10,039,874 to Schwammenthal, which is the US national phase of International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. Pat. No. 9,764,113 to Tuval, issued Sep. 19, 2017, entitled "Curved catheter," which claims priority from U.S. Provisional Patent Application 61/914,470 to Tuval, filed Dec. 11, 2013, entitled "Curved catheter;" and U.S. Pat. No. 9,597,205 to Tuval, which is the US national phase of International Patent Application PCT/IL2013/050495 to Tuval (published as WO 13/183060), filed Jun. 6, 2013, entitled "Prosthetic renal valve," which claims priority from US Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:

a left-ventricular assist device configured to assist left-ventricular functioning of a subject, the left-ventricular assist device including:

a pump-outlet tube configured such that a proximal portion of the pump-outlet tube traverses an aortic valve of the subject, and a distal portion of the pump-outlet tube is disposed within a left ventricle of the subject, the pump-outlet tube defining at least one blood inlet opening that is configured to be disposed within the left ventricle and at least one blood outlet opening that is configured to be disposed within an aorta of the subject;

a mixed-flow impeller disposed in the pump-outlet tube and configured to pump blood through the pump-outlet tube from the subject's left ventricle to the subject's aorta, the mixed-flow impeller comprising:

a central axial spring, one or more impeller blades defined by elongate elements which wind around the central axial spring and a film of material supported between the central axial spring and the elongate elements, and an inflatable portion disposed along an axis of the impeller and between the edges of the impeller blades and the central axial spring, the inflatable portion being shaped such that, in an expanded configuration of the inflatable portion, a diameter of the inflatable portion increases from a distal end of the inflatable portion to a proximal end of the inflatable portion, the mixed-flow impeller thereby being configured to impart radial flow components to blood as the blood flows from the distal end to the proximal end of the mixed-flow impeller.

2. The apparatus according to claim 1, wherein the pump-outlet tube defines a widened region in the vicinity of the impeller, which is wider than a portion of the pump-outlet tube proximal thereto, and wherein the pump-outlet tube is configured to redirect the radial blood flow components axially, by the pump-outlet tube narrowing within the portion of the pump-outlet tube that is proximal to the widened portion.

3. The apparatus according to claim 1, wherein, in the inflated configuration, the inflatable portion of the impeller has a three-dimensional teardrop shape.

4. The apparatus according to claim 1, wherein the inflatable portion of the impeller comprises a shape memory alloy that is shape set such that the inflatable portion of the impeller is self inflatable.

5. The apparatus according to claim 1, further comprising an expandable flow rectifier that is configured to reduce radial flow components from blood flow through the pump-outlet tube prior to the blood flowing from the at least one blood outlet opening, the expandable flow rectifier being disposed along an axis of the pump-outlet tube and, in the expanded configuration of the flow rectifier, being shaped such that a diameter of the flow rectifier decreases from a distal end of the expandable flow rectifier to a proximal end of the expandable flow rectifier.

6. The apparatus according to claim 1, wherein the left-ventricular assist device is configured for use with a purging fluid, wherein the left-ventricular assist device comprises a purging system configured to purge portions of the left-ventricular assist device by pumping the purging fluid through the left-ventricular assist device, and wherein the inflatable portion of the impeller is configured to be inflated with the purging fluid.

7. The apparatus according to claim 6, wherein the purging system is configured to control the inflation of the inflatable portion of the impeller, by modulating the pressure at which the purging fluid is pumped into the ventricular assist device.

8. The apparatus according to claim 1, wherein the one or more impeller blades are shaped to transition from being spiral shaped within a distal portion of the impeller to being substantially radially-extending within a proximal portion of the impeller.

9. The apparatus according to claim 8, wherein the distal portion of the impeller is configured primarily to impart axial flow to blood that is pumped by the distal portion of the impeller, and the proximal portion of the impeller is configured to impart substantial radial flow to blood that is pumped by the proximal portion of the impeller.

10. The apparatus according to claim 1, further comprising one or more spiral flow rectifiers disposed within the pump-outlet tube, proximally with respect to the impeller, the spiral flow rectifiers being configured to reduce radial flow components from blood flow by converting radial flow components to axial flow prior to the blood flowing out of the at least one blood outlet opening.

11. The apparatus according to claim 10, wherein the one or more spiral flow rectifiers have spiral shapes with a pitch of the spiral shapes increasing from the distal ends of the flow rectifiers to their proximal ends, such that the spiral flow rectifiers are configured to gradually covert radial flow to axial flow.

\* \* \* \* \*